United States Patent [19]
Orlowski et al.

[11] Patent Number: 6,127,519
[45] Date of Patent: Oct. 3, 2000

[54] CALCITONIN DERIVATIVES

[75] Inventors: Ronald C. Orlowski, Belmont, Calif.;
Satoshi Hanamura, Ibaraki, Japan;
Masahiko Marumoto, Ibaraki, Japan;
Kenji Sakamoto, Ibaraki, Japan;
Yoshihiro Waki, Ibaraki, Japan

[73] Assignee: Tsumura & Co., Tokyo, Japan

[21] Appl. No.: 07/401,432

[22] PCT Filed: Apr. 19, 1990

[86] PCT No.: PCT/US90/02143

§ 371 Date: Dec. 21, 1990

§ 102(e) Date: Dec. 21, 1990

[87] PCT Pub. No.: WO90/12809

PCT Pub. Date: Nov. 1, 1990

Related U.S. Application Data

[63] Continuation-in-part of application No. 07/431,350, Nov. 16, 1989, abandoned, which is a continuation-in-part of application No. 07/341,800, Apr. 21, 1989, abandoned.

[51] Int. Cl.⁷ .................................................. C07K 17/00
[52] U.S. Cl. ........................... 530/307; 514/12; 514/808; 530/324; 530/325; 530/318; 530/317
[58] Field of Search .................................. 530/307, 324, 530/325, 318, 317; 514/12, 808; 930/60, DIG. 660, DIG. 661, DIG. 670, DIG. 671, DIG. 800, DIG. 802, DIG. 820, DIG. 821, 10, 20

[56] References Cited

U.S. PATENT DOCUMENTS

| | | | |
|---|---|---|---|
| 3,798,203 | 3/1974 | Brugger et al. | 530/307 |
| 3,910,872 | 10/1975 | Riniker et al. | 530/307 |
| 4,086,221 | 4/1978 | Sakakibara et al. | 530/307 |
| 4,604,237 | 8/1986 | Orlowski et al. | 530/307 |
| 4,606,856 | 8/1986 | Seyler et al. | 530/307 |
| 4,622,386 | 11/1986 | Orlowski et al. | 530/307 |
| 4,644,054 | 2/1987 | Kempe | 530/307 |
| 4,658,014 | 4/1987 | Kempe | 530/307 |
| 4,663,309 | 5/1987 | Kaiser et al. | 530/307 |
| 4,732,969 | 3/1988 | Orlowski et al. | 530/307 |
| 4,746,728 | 5/1988 | Orlowski et al. | 530/307 |
| 4,758,550 | 7/1988 | Cardinaux et al. | 530/307 |
| 4,764,590 | 8/1988 | Orlowski et al. | 530/307 |
| 4,764,591 | 8/1988 | Orlowski et al. | 530/307 |
| 4,820,804 | 4/1989 | Orlowski et al. | 530/307 |

FOREIGN PATENT DOCUMENTS

| | | | |
|---|---|---|---|
| 3300241 | 8/1989 | European Pat. Off. | |
| 550774 | 10/1968 | Switzerland | 530/307 |

OTHER PUBLICATIONS

The Merck Manual of Diagnosis and Therapy, 11$^{th}$ ed., pp. 965–966, (1966).

Ritter et al, Helvetica Chimica Acta, vol. 51, pp. 924–928, (1968).

*Primary Examiner*—Keith D. MacMillan
*Assistant Examiner*—T. D. Wessendorf
*Attorney, Agent, or Firm*—Burns, Doane, Swecker & Mathis, L.L.P.

[57] ABSTRACT

Peptides useful in the regulation of calcium metabolism are disclosed. Also disclosed are pharmaceutical compositions of matter containing such peptides as well as a method for the regulation of calcium metabolism in a patient in need of such treatment. The peptides contain modified or unmodified portions of an amino acid sequence at the 8- to 32-positions of native calcination.

4 Claims, No Drawings

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:1:

Ala Gly Asn Leu Ser Thr Ala Met Leu Gly Lys Leu Ser Gln Glu Leu
1               5                  10                  15

His Lys Leu Gln Thr Tyr Pro Gln Thr Ala Ile Gly Val Gly Ala Pro
            20                  25                  30

(2) INFORMATION FOR SEQ ID NO:2:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:2:

Ala Gly Asn Leu Ser Thr Ala Met Leu Gly Lys Leu Ser Gln Glu Leu
1               5                  10                  15

His Lys Gln Thr Tyr Pro Gln Thr Ala Ile Gly Val Gly Ala Pro
            20                  25                  30

(2) INFORMATION FOR SEQ ID NO:3:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:3:

Ala Gly Asn Leu Ser Thr Ala Met Leu Gly Lys Leu Ser Gln Glu Leu
1               5                  10                  15

His Lys Leu Tyr Pro Gln Thr Ala Ile Gly Val Gly Ala Pro
            20                  25                  30

(2) INFORMATION FOR SEQ ID NO:4:

(i) SEQUENCE CHARACTERISTICS:
        (A) LENGTH: 32 amino acids
        (B) TYPE: amino acid (D) TOPOLOGY: linear (ii) MOLECULE TYPE: peptide (ix) FEATURE:
         (A) NAME/KEY: Disulfide-bond
         (B) LOCATION: 1..7

(xi) SEQUENCE DESCRIPTION: SEQ ID NO:4:

Ala Gly Asn Leu Ser Thr Ala Met Leu Gly Lys Leu Ser Gln Glu Leu
1               5                   10                  15

His Lys Gly Gln Thr Tyr Pro Gln Thr Ala Ile Gly Val Gly Ala Pro
            20                  25                  30

(2) INFORMATION FOR SEQ ID NO:5:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
         (A) NAME/KEY: Disulfide-bond
         (B) LOCATION: 1..7

(xi) SEQUENCE DESCRIPTION: SEQ ID NO:5:

Ala Gly Asn Leu Ser Thr Ala Met Leu Gly Lys Leu Ser Gln Glu Leu
1               5                   10                  15

His Lys Leu Gln Thr Tyr Pro Gln Thr Ala Ile Gly Ser Gly Thr Pro
            20                  25                  30

(2) INFORMATION FOR SEQ ID NO:6:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
         (A) NAME/KEY: Disulfide-bond
         (B) LOCATION: 1..7

(xi) SEQUENCE DESCRIPTION: SEQ ID NO:6:

Ala Gly Asn Leu Ser Thr Ala Met Leu Gly Lys Leu Ser Gln Glu Leu
1               5                   10                  15

His Lys Gln Thr Tyr Pro Gln Thr Ala Ile Gly Ser Gly Thr Pro
            20                  25                  30

(2) INFORMATION FOR SEQ ID NO:7:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
         (A) NAME/KEY: Disulfide-bond
         (B) LOCATION: 1..7

(xi) SEQUENCE DESCRIPTION: SEQ ID NO:7:

Ala Gly Asn Leu Ser Thr Ala Met Leu Gly Lys Leu Ser Gln Glu Leu
1               5                   10                  15

```
His Lys Leu Tyr Pro Gln Thr Ala Ile Gly Ser Gly Thr Pro
            20                  25                  30

(2) INFORMATION FOR SEQ ID NO:8:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:8:

Ala Gly Asn Leu Ser Thr Ala Met Leu Gly Lys Leu Ser Gln Glu Leu
1               5                  10                  15

His Lys Gly Gln Thr Tyr Pro Gln Thr Ala Ile Gly Ser Gly Thr Pro
            20                  25                  30

(2) INFORMATION FOR SEQ ID NO:9:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:9:

Ala Gly Asn Leu Ser Thr Ala Gly Leu Gly Lys Leu Ser Gln Glu Leu
1               5                  10                  15

His Lys Leu Gln Thr Tyr Pro Gln Thr Ala Ile Gly Val Gly Ala Pro
            20                  25                  30

(2) INFORMATION FOR SEQ ID NO:10:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:10:

Ala Gly Asn Leu Ser Thr Ala Ala Leu Gly Lys Leu Ser Gln Glu Leu
1               5                  10                  15

His Lys Leu Gln Thr Tyr Pro Gln Thr Ala Ile Gly Val Gly Ala Pro
            20                  25                  30

(2) INFORMATION FOR SEQ ID NO:11:

(i) SEQUENCE CHARACTERISTICS:
        (A) LENGTH: 32 amino acids
        (B) TYPE: amino acid
        (D) TOPOLOGY: linear (ii) MOLECULE TYPE: peptide
```

(ix) FEATURE:
            (A) NAME/KEY: Disulfide-bond
            (B) LOCATION: 1..7

(xi) SEQUENCE DESCRIPTION: SEQ ID NO:11:

Ala Gly Asn Leu Ser Thr Ala Val Leu Gly Lys Leu Ser Gln Glu Leu
1               5                   10                  15

His Lys Leu Gln Thr Tyr Pro Gln Thr Ala Ile Gly Val Gly Ala Pro
            20                  25                  30

(2) INFORMATION FOR SEQ ID NO:12:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (ix) FEATURE:
            (A) NAME/KEY: Disulfide-bond
            (B) LOCATION: 1..7

(xi) SEQUENCE DESCRIPTION: SEQ ID NO:12:

Ala Gly Asn Leu Ser Thr Ala Pro Leu Gly Lys Leu Ser Gln Glu Leu
1               5                   10                  15

His Lys Leu Gln Thr Tyr Pro Gln Thr Ala Ile Gly Val Gly Ala Pro
            20                  25                  30

(2) INFORMATION FOR SEQ ID NO:13:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (ix) FEATURE:
            (A) NAME/KEY: Disulfide-bond
            (B) LOCATION: 1..7

(xi) SEQUENCE DESCRIPTION: SEQ ID NO:13:

Ala Gly Asn Leu Ser Thr Ala Leu Leu Gly Lys Leu Ser Gln Glu Leu
1               5                   10                  15

His Lys Leu Gln Thr Tyr Pro Gln Thr Ala Ile Gly Val Gly Ala Pro
            20                  25                  30

(2) INFORMATION FOR SEQ ID NO:14:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (xi) SEQUENCE DESCRIPTION: SEQ ID NO:14:

Ala Gly Asn Leu Ser Thr Ala Met Leu Gly Lys Leu Ser Gln Glu Leu
1               5                   10                  15

His Lys Leu Gln Thr Tyr Pro Gln Thr Ala Ile Gly Val Gly Ala Pro
            20                  25                  30

(2) INFORMATION FOR SEQ ID NO:15:

(i) SEQUENCE CHARACTERISTICS:
            (A) LENGTH: 31 amino acids

```
            (B) TYPE: amino acid
            (D) TOPOLOGY: linear (ii) MOLECULE TYPE: peptide (xi) SEQUENCE DESCRIPTION: SEQ ID NO:15:

Ala Gly Asn Leu Ser Thr Ala Met Leu Gly Lys Leu Ser Gln Glu Leu
1               5                   10                  15

His Lys Gln Thr Tyr Pro Gln Thr Ala Ile Gly Val Gly Ala Pro
            20                  25                  30

(2) INFORMATION FOR SEQ ID NO:16:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:16:

Ala Gly Asn Leu Ser Thr Ala Met Leu Gly Lys Leu Ser Gln Glu Leu
1               5                   10                  15

His Lys Leu Thr Pro Gln Thr Ala Ile Gly Val Gly Ala Pro
            20                  25                  30

(2) INFORMATION FOR SEQ ID NO:17:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:17:

Ala Gly Asn Leu Ser Thr Ala Met Leu Gly Lys Leu Ser Gln Glu Leu
1               5                   10                  15

His Lys Gly Gln Thr Tyr Pro Gln Thr Ala Ile Gly Val Gly Ala Pro
            20                  25                  30

(2) INFORMATION FOR SEQ ID NO:18:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:18:

Ala Gly Asn Leu Ser Thr Ala Met Leu Gly Lys Leu Ser Gln Glu Leu
1               5                   10                  15

His Lys Leu Gln Thr Tyr Pro Gln Thr Ala Ile Gly Ser Gly Thr Pro
            20                  25                  30

(2) INFORMATION FOR SEQ ID NO:19:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:19:
```

```
Ala Gly Asn Leu Thr Ser Ala Met Leu Gly Lys Leu Ser Gln Glu Leu
1               5                   10                  15

His Lys Leu Gln Thr Tyr Pro Gln Thr Ala Ile Gly Ser Gly Thr Pro
            20                  25                  30
```

(2) INFORMATION FOR SEQ ID NO:20:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:20:

```
Ala Gly Asn Leu Thr Ser Ala Leu Leu Gly Lys Leu Ser Gln Glu Leu
1               5                   10                  15

His Lys Leu Gln Thr Tyr Pro Gln Thr Ala Ile Gly Val Gly Ala Pro
            20                  25                  30
```

(2) INFORMATION FOR SEQ ID NO:21:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..7
        (D) OTHER INFORMATION: /note= "Cross-linked by ethyl
            linkage."

(xi) SEQUENCE DESCRIPTION: SEQ ID NO:21:

```
Xaa Gly Asn Leu Ser Thr Ala Met Leu Gly Lys Leu Ser Gln Glu Leu
1               5                   10                  15

His Lys Leu Gln Thr Tyr Pro Gln Thr Ala Ile Gly Val Gly Ala Pro
            20                  25                  30
```

(2) INFORMATION FOR SEQ ID NO:22:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..7
        (D) OTHER INFORMATION: /note= "Cross-linked by ethyl
            linkage."

(xi) SEQUENCE DESCRIPTION: SEQ ID NO:22:

```
Xaa Gly Asn Leu Ser Thr Ala Leu Leu Gly Lys Leu Ser Gln Glu Leu
```

```
            1               5              10              15
His Lys Leu Gln Thr Tyr Pro Gln Thr Ala Ile Gly Val Gly Ala Pro
                20                  25                  30
```

(2) INFORMATION FOR SEQ ID NO:23:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:23:

```
Ala Asn Leu Ser Thr Ala Met Leu Gly Lys Leu Ser Gln Glu Leu His
1               5                  10                  15
Lys Leu Gln Thr Tyr Pro Gln Thr Ala Ile Gly Val Gly Ala Pro
                20                  25                  30
```

(2) INFORMATION FOR SEQ ID NO:24:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:24:

```
Ala Asn Leu Ser Thr Ala Leu Leu Gly Lys Leu Ser Gln Glu Leu His
1               5                  10                  15
Lys Leu Gln Thr Tyr Pro Gln Thr Ala Ile Gly Val Gly Ala Pro
                20                  25                  30
```

(2) INFORMATION FOR SEQ ID NO:25:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(ix) FEATURE:
        (A) NAME/KEY: Modified-site
        (B) LOCATION: 1
        (D) OTHER INFORMATION: /note= "Modified by additional
            CHHH-CO- at the amino end."

(xi) SEQUENCE DESCRIPTION: SEQ ID NO:25:

```
Ala Asn Leu Ser Thr Ala Leu Leu Gly Lys Leu Ser Gln Glu Leu His
1               5                  10                  15
```

```
Lys Leu Gln Thr Tyr Pro Gln Thr Ala Ile Gly Val Gly Ala Pro
            20                  25                  30
```

(2) INFORMATION FOR SEQ ID NO:26:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:26:

```
Xaa Asn Leu Ser Thr Ala Leu Leu Gly Lys Leu Ser Gln Glu Leu His
1               5                   10                  15
Lys Leu Gln Thr Tyr Pro Gln Thr Ala Ile Gly Val Gly Ala Pro
            20                  25                  30
```

(2) INFORMATION FOR SEQ ID NO:27:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CHH-CHH-CHH-NH-CO-."

(xi) SEQUENCE DESCRIPTION: SEQ ID NO:27:

```
Ala Asn Leu Ser Thr Ala Met Leu Gly Lys Leu Ser Gln Glu Leu His
1               5                   10                  15
Lys Leu Gln Thr Tyr Pro Gln Thr Ala Ile Gly Val Gly Ala Pro
            20                  25                  30
```

(2) INFORMATION FOR SEQ ID NO:28:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CHH-CHH-CHH-NH-CO-."

(xi) SEQUENCE DESCRIPTION: SEQ ID NO:28:

```
Ala Asn Leu Ser Thr Ala Leu Leu Gly Lys Leu Ser Gln Glu Leu His
1               5                   10                  15
```

```
Lys Leu Gln Thr Tyr Pro Gln Thr Ala Ile Gly Val Gly Ala Pro
        20                  25                  30

(2) INFORMATION FOR SEQ ID NO:29:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CHH-CO-NH-CHH-CHH-."

(xi) SEQUENCE DESCRIPTION: SEQ ID NO:29:

Ala Asn Leu Ser Thr Ala Leu Leu Gly Lys Leu Ser Gln Glu Leu His
1               5                   10                  15

Lys Leu Gln Thr Tyr Pro Gln Thr Ala Ile Gly Val Gly Ala Pro
        20                  25                  30

(2) INFORMATION FOR SEQ ID NO:30:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CHH-CHH-NH-CO-CHH-."

(xi) SEQUENCE DESCRIPTION: SEQ ID NO:30:

Ala Asn Leu Ser Thr Ala Leu Leu Gly Lys Leu Ser Gln Glu Leu His
1               5                   10                  15

Lys Leu Gln Thr Tyr Pro Gln Thr Ala Ile Gly Val Gly Ala Pro
        20                  25                  30

(2) INFORMATION FOR SEQ ID NO:31:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:31:

Ala Asn Leu Ser Thr Ala Leu Leu Gly Lys Leu Ser Gln Asp Leu Asn
1               5                   10                  15

Lys Phe His Thr Tyr Pro Gln Thr Ala Ile Gly Val Gly Ala Pro
        20                  25                  30

(2) INFORMATION FOR SEQ ID NO:32:

(i) SEQUENCE CHARACTERISTICS:
```

(A) LENGTH: 31 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:32:

Xaa Asn Leu Ser Thr Ala Leu Leu Gly Lys Leu Ser Gln Asp Leu Asn
1               5                   10                  15

Lys Phe His Thr Tyr Pro Gln Thr Ala Ile Gly Val Gly Ala Pro
            20                  25                  30

(2) INFORMATION FOR SEQ ID NO:33:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:33:

Xaa Asn Leu Ser Thr Ala Leu Leu Gly Lys Leu Thr Gln Asp Leu Asn
1               5                   10                  15

Lys Phe His Thr Tyr Pro Gln Thr Ala Ile Gly Val Gly Ala Pro
            20                  25                  30

(2) INFORMATION FOR SEQ ID NO:34:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:34:

```
Xaa Asn Leu Ser Thr Ala Met Leu Gly Thr Tyr Thr Gln Asp Phe Asn
1               5                   10                  15

Lys Phe His Thr Phe Pro Gln Thr Ala Ile Gly Val Gly Ala Pro
            20                  25                  30

(2) INFORMATION FOR SEQ ID NO:35:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:35:

Xaa Asn Leu Ser Thr Ala Val Leu Gly Thr Tyr Thr Gln Asp Phe Asn
1               5                   10                  15

Lys Phe His Thr Phe Pro Gln Thr Ala Ile Gly Val Gly Ala Pro
            20                  25                  30

(2) INFORMATION FOR SEQ ID NO:36:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:36:

Xaa Asn Leu Ser Thr Ala Leu Leu Gly Thr Tyr Thr Gln Asp Phe Asn
1               5                   10                  15

Lys Phe His Thr Phe Pro Gln Thr Ala Ile Gly Val Gly Ala Pro
            20                  25                  30

(2) INFORMATION FOR SEQ ID NO:37:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Modified-site
```

(B) LOCATION: 1
            (D) OTHER INFORMATION: /note= "Xaa = -CHH-CHH-CO- bound
                to the amino end of residue 2."

(ix) FEATURE:
            (A) NAME/KEY: Cross-links
            (B) LOCATION: 1..7
            (D) OTHER INFORMATION: /note= "Cross-linked by
                -CO-NH-CHH-CHH-CHH-."

(xi) SEQUENCE DESCRIPTION: SEQ ID NO:37:

Xaa Gly Asn Leu Ser Thr Ala Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

(2) INFORMATION FOR SEQ ID NO:38:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = -CHH-CHH-CO- bound
                to the amino end of residue 2."

(ix) FEATURE:
            (A) NAME/KEY: Cross-links
            (B) LOCATION: 1..7
            (D) OTHER INFORMATION: /note= "Cross-linked by
                -CO-NH-CHH-CHH-CHH-."

(xi) SEQUENCE DESCRIPTION: SEQ ID NO:38:

Xaa Gly Asn Leu Ser Thr Ala Val Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

(2) INFORMATION FOR SEQ ID NO:39:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = -CHH-CHH-CO- bound
                to the amino end of residue 2."

(ix) FEATURE:
            (A) NAME/KEY: Cross-links
            (B) LOCATION: 1..7
            (D) OTHER INFORMATION: /note= "Cross-linked by
                -CO-NH-CHH-CHH-CHH-."

(xi) SEQUENCE DESCRIPTION: SEQ ID NO:39:

Xaa Gly Asn Leu Ser Thr Ala Leu Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

(2) INFORMATION FOR SEQ ID NO:40:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..7
        (D) OTHER INFORMATION: /note= "Cross-linked by -CO-CHH-."

(xi) SEQUENCE DESCRIPTION: SEQ ID NO:40:

Gly Gly Asn Leu Ser Thr Ala Met Leu Gly Thr Tyr Thr Gln Asp Phe
1               5                  10                  15

Asn Lys Phe His Thr Phe Pro Gln Thr Ala Ile Gly Val Gly Ala Pro
            20                  25                  30

(2) INFORMATION FOR SEQ ID NO:41:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..7
        (D) OTHER INFORMATION: /note= "Cross-linked by -CO-CHH-."

(xi) SEQUENCE DESCRIPTION: SEQ ID NO:41:

Gly Gly Asn Leu Ser Thr Ala Val Leu Gly Thr Tyr Thr Gln Asp Phe
1               5                  10                  15

Asn Lys Phe His Thr Phe Pro Gln Thr Ala Ile Gly Val Gly Ala Pro
            20                  25                  30

(2) INFORMATION FOR SEQ ID NO:42:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..7
        (D) OTHER INFORMATION: /note= "Cross-linked by -CO-CHH-."

(xi) SEQUENCE DESCRIPTION: SEQ ID NO:42:

Gly Gly Asn Leu Ser Thr Ala Leu Leu Gly Thr Tyr Thr Gln Asp Phe
1               5                  10                  15

Asn Lys Phe His Thr Phe Pro Gln Thr Ala Ile Gly Val Gly Ala Pro
            20                  25                  30

(2) INFORMATION FOR SEQ ID NO:43:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:

(A) NAME/KEY: Modified-site
            (B) LOCATION: 1
            (D) OTHER INFORMATION: /note= "Xaa = -CHH-CHH-CO- bound
                to the amino end of residue 2."

(ix) FEATURE:
            (A) NAME/KEY: Cross-links
            (B) LOCATION: 1..6
            (D) OTHER INFORMATION: /note= "Cross-linked by
                -CO-NH-CHH-CHH-CHH-."

(xi) SEQUENCE DESCRIPTION: SEQ ID NO:43:

Xaa Asn Leu Ser Thr Ala Val Leu Gly Lys Leu Ser Gln Glu Leu His
1               5                   10                  15

Lys Leu Gln Thr Tyr Pro Arg Thr Asn Thr Gly Ser Gly Thr Pro
            20                  25                  30

(2) INFORMATION FOR SEQ ID NO:44:

(i) SEQUENCE CHARACTERISTICS:
            (A) LENGTH: 30 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = -CHH-CHH-CO- bound
                to the amino end of residue 2."

(ix) FEATURE:
            (A) NAME/KEY: Cross-links
            (B) LOCATION: 1..6
            (D) OTHER INFORMATION: /note= "Cross-linked by
                -CO-NH-CHH-CHH-CHH-."

(xi) SEQUENCE DESCRIPTION: SEQ ID NO:44:

Xaa Asn Leu Ser Thr Ala Val Leu Gly Lys Leu Ser Gln Glu Leu His
1               5                   10                  15

Lys Gln Thr Tyr Pro Arg Thr Asn Thr Gly Ser Gly Thr Pro
            20                  25                  30

(2) INFORMATION FOR SEQ ID NO:45:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (ix) FEATURE:
            (A) NAME/KEY: Cross-links
            (B) LOCATION: 1..7
            (D) OTHER INFORMATION: /note= "Cross-linked by -CO-CHH-."

(xi) SEQUENCE DESCRIPTION: SEQ ID NO:45:

Gly Ser Asn Leu Ser Thr Ala Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

(2) INFORMATION FOR SEQ ID NO:46:

(i) SEQUENCE CHARACTERISTICS:
            (A) LENGTH: 31 amino acids
            (B) TYPE: amino acid
            (D) TOPOLOGY: linear (ii) MOLECULE TYPE: peptide (ix) FEATURE:
    (A) NAME/KEY: Cross-links
    (B) LOCATION: 1..7
    (D) OTHER INFORMATION: /note= "Cross-linked by -CO-CHH-."

(xi) SEQUENCE DESCRIPTION: SEQ ID NO:46:

```
Gly Ser Asn Leu Ser Thr Ala Val Leu Gly Lys Leu Ser Gln Glu Leu
1               5                   10                  15
His Lys Gln Thr Tyr Pro Arg Thr Asn Thr Gly Ser Gly Thr Pro
            20                  25                  30
```

(2) INFORMATION FOR SEQ ID NO:47:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(ix) FEATURE:
        (A) NAME/KEY: Cross-links
        (B) LOCATION: 1..6
        (D) OTHER INFORMATION: /note= "Cross-linked by
            -CO-NH-CHH-CHH-CHH-."

(xi) SEQUENCE DESCRIPTION: SEQ ID NO:47:

```
Xaa Asn Leu Ser Thr Ala Val Leu Gly Lys Leu Ser Gln Glu Leu His
1               5                   10                  15
Lys Leu Gln Thr Tyr Pro Arg Thr Asp Val Gly Ala Gly Thr Pro
            20                  25                  30
```

(2) INFORMATION FOR SEQ ID NO:48:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..7
        (D) OTHER INFORMATION: /note= "Cross-linked by -CO-CHH-."

(xi) SEQUENCE DESCRIPTION: SEQ ID NO:48:

```
Gly Ser Asn Leu Ser Thr Ala Val Leu Gly Lys Leu Ser Gln Glu Leu
1               5                   10                  15
His Lys Leu Gln Thr Tyr Pro Arg Thr Asp Val Gly Ala Gly Thr Pro
            20                  25                  30
```

(2) INFORMATION FOR SEQ ID NO:49:

(i) SEQUENCE CHARACTERISTICS:
        (A) LENGTH: 31 amino acids
        (B) TYPE: amino acid
        (D) TOPOLOGY: linear (ii) MOLECULE TYPE: peptide

```
    (ix) FEATURE:
         (A) NAME/KEY: Modified-site
         (B) LOCATION: 1
         (D) OTHER INFORMATION: /note= "Xaa = -CHH-CHH-CO- bound
             to the amino end of residue 2."

(ix) FEATURE:
         (A) NAME/KEY: Cross-links
         (B) LOCATION: 1..6
         (D) OTHER INFORMATION: /note= "Cross-linked by
             -CO-NH-CHH-CHH-CHH-."

(xi) SEQUENCE DESCRIPTION: SEQ ID NO:49:

Xaa Ser Leu Ser Thr Ala Val Leu Gly Lys Leu Ser Gln Glu Leu His
1               5                   10                  15

Lys Leu Gln Thr Tyr Pro Arg Thr Asp Val Gly Ala Gly Thr Pro
            20                  25                  30

(2) INFORMATION FOR SEQ ID NO:50:

(i) SEQUENCE CHARACTERISTICS:
         (A) LENGTH: 32 amino acids
         (B) TYPE: amino acid
         (D) TOPOLOGY: linear (ii) MOLECULE TYPE: peptide (ix) FEATURE:
         (A) NAME/KEY: Cross-links
         (B) LOCATION: 1..7
         (D) OTHER INFORMATION: /note= "Cross-linked by -CO-CHH-."

(xi) SEQUENCE DESCRIPTION: SEQ ID NO:50:

Gly Ala Ser Leu Ser Thr Ala Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

(2) INFORMATION FOR SEQ ID NO:51:

(i) SEQUENCE CHARACTERISTICS:
         (A) LENGTH: 32 amino acids
         (B) TYPE: amino acid
         (D) TOPOLOGY: linear (ii) MOLECULE TYPE: peptide (ix) FEATURE:
         (A) NAME/KEY: Cross-links
         (B) LOCATION: 1..7
         (D) OTHER INFORMATION: /note= "Cross-linked by -CO-CHH-."

(xi) SEQUENCE DESCRIPTION: SEQ ID NO:51:

Gly Asn Ser Leu Ser Thr Ala Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

(2) INFORMATION FOR SEQ ID NO:52:

(i) SEQUENCE CHARACTERISTICS:
         (A) LENGTH: 31 amino acids
         (B) TYPE: amino acid
         (D) TOPOLOGY: linear (ii) MOLECULE TYPE: peptide (ix) FEATURE:
         (A) NAME/KEY: Cross-links
         (B) LOCATION: 1..6
```

```
        (D) OTHER INFORMATION: /note= "Cross-linked by
            -CO-NH-CHH-CHH-CHH-."

(ix) FEATURE:
        (A) NAME/KEY: Modified-site
        (B) LOCATION: 1
        (D) OTHER INFORMATION: /note= "Xaa = -CHH-CHH-CO- bound
            to the amino end of residue 2."

(xi) SEQUENCE DESCRIPTION: SEQ ID NO:52:

Xaa Asn Leu Ser Thr Ala Val Leu Ser Ala Tyr Trp Arg Asn Leu Asn
1               5                   10                  15

Asn Phe His Arg Phe Ser Gly Met Gly Phe Gly Pro Glu Thr Pro
            20                  25              30

(2) INFORMATION FOR SEQ ID NO:53:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (ix) FEATURE:
        (A) NAME/KEY: Cross-links
        (B) LOCATION: 1..7
        (D) OTHER INFORMATION: /note= "Cross-linked by -CO-CHH-."

(xi) SEQUENCE DESCRIPTION: SEQ ID NO:53:

Gly Ser Asn Leu Ser Thr Ala Val Leu Ser Ala Tyr Trp Arg Asn Leu
        1               5                   10                  15

Asn Asn Phe His Arg Phe Ser Gly Met Gly Phe Gly Pro Glu Thr Pro
                20                  25              30
```

CALCITONIN DERIVATIVES

This application is a continuation in part of application Ser. No. 07/431,350, filed Nov. 16, 1989, abandoned, which in turn is a continuation in part of Ser. No. 07/341,800, filed Apr. 21, 1989, abandoned.

BACKGROUND OF THE INVENTION

1. Field of the Invention

The present invention relates to a novel, physiologically active family of peptides effective for the treatment of diseases caused by abnormal calcium metabolism in the body, such as hypercalcemia, Paget's Disease of bone, and osteoporosis.

2. Description of the Related Art

Estrogens, vitamin D, calcium salts, and calcitonin have been administered for the treatment of hypercalcemia, Paget's Disease of bone, and osteoporosis, but are defective in that the object is limited or the effect is not clear.

Calcitonin is a single-chain polypeptide hormone consisting of 32 amino acids, which occurs in nature and is secreted from the thyroid gland in mammals and from the ultimo-branchial gland in fish, and birds. The amino acid composition or sequence differs to a large extent among the different species, but the physiological activity in blood is substantially the same there among.

SUMMARY OF THE INVENTION

Accordingly, the present inventors carried out research into the development of a calcium metabolism-regulating agent capable of treating hypercalcemia, Paget's Disease of bone, and osteoporosis, and to this end, synthesized novel peptides and examined the physiological activities thereof. As a result, it was found that the novel peptides described below have a very high activity of lowering the level of blood calcium.

More specifically, in accordance with one aspect of the present invention, there is provided a novel physiologically active peptide (hereinafter referred to as "the peptide of the present invention") having the following amino acid sequence (presented in the sequence listing as SEQ ID NO:1 thru SEQ ID NO:53):

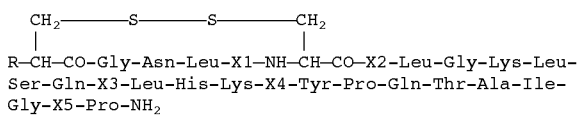

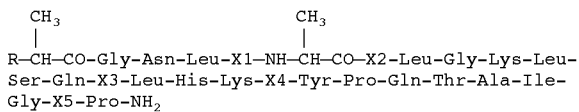

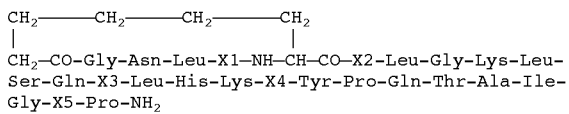

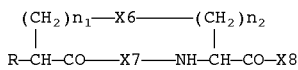

wherein
X1 stands for Ser-Thr or Thr-Ser,
X2 stands for Met, Gly, Ala, Val, n-Val, Pro, Leu, n-Leu, Ile, Phe or α-aminolactic acid,
X3 stands for Asp or Glu,
X4 stands for Leu-Gln-Thr, Gln-Thr, Leu or Gly-Gln-Thr,
X5 stands for Val-Gly-Ala or Ser-Gly-Thr,
R stands for H, $NH_2$, N-acyl or N-alkyl,
X6 stands for CO-NH or NH-CO,
X7 stands for an amino acid sequence at the 2- to 6-positions of native calcitonin, or a substitution, deletion or addition derivative thereof, having 0 to 6 amino acids,
X8 stands for an amino acid sequence at the 8- to 32-positions of native calcitonin, or a substitution, deletion or addition derivative thereof, and
each of $n_1$ and $n_2$ is an integer of 1 to 19 and $n_1+n_2$ is 2 to 20, or a pharmacologically acceptable salt thereof.

In accordance with another aspect of the present invention, there is provided a calcium metabolism-regulating agent comprising the above-mentioned peptide or a pharmacologically acceptable salt thereof as an effective ingredient.

DESCRIPTION OF THE PREFERRED EMBODIMENTS

By the term "calcium metabolism-regulating agent" used in the instant specification and appended claims is meant an agent effective for the remedy of a disease, one considered to be caused by an abnormal metabolism of calcium in the body, such as hypercalcemia or Paget's Disease of bone and osteoporosis In the instant specification and appended claims, amino acids are abbreviated according to the method adopted by the Commission on Biochemical Nomenclature (CBN) of the International Union of Pure and Applied Chemistry and the International Union of Biochemistry (IUPAC-IUB). For example, the following abbreviations are adopted.

Ala: L-alanine, Arg: L-arginine, Asn:
L-asparagine, Asp: L-aspartic acid, Cys:
L-cysteine, Gln: L-glutamine, Glu: L-glutamic acid, Gly: glycine, His: L-histidine, Ile:
L-isoleucine, Leu: L-leucine, Lys: L-lysine, Met:
L-methionine, Phe: L-phenylalanine, Pro:
L-proline, Ser: L-serine, Thr: L-threonine, Tyr:
L-tyrosine, Trp: L-tryptophan, Val: L-valine The peptide of the present invention can be synthesized according to the known liquid phase method or solid phase method customarily adopted for the synthesis of peptides. For example, if the solid phase method is adopted, the synthesis is carried out in the following manner.

More specifically, protected L-amino acids corresponding to the amino acids included in the above-mentioned formula are condensed in sequence from the C-terminal in an organic solvent-insoluble resin and then an acid treatment is carried out, whereby the peptide (free peptide) of the present invention is obtained.

An organic solvent-insoluble resin, which is stable against a solvent, is almost unbreakable, and has a good swelling property is preferably used as the organic solvent-insoluble resin. As specific examples, there can be mentioned a resin formed by introducing a functional group such as a chloromethyl group or hydroxymethyl group into a styrene/divinylbenzene copolymer and a resin formed by converting the above-mentioned copolymer to a benzhydrylamine type.

Since the C-terminal of the peptide of the present invention is an amide, when the above-mentioned two types of resins are used, amidation should be carried out by using ammonia or the like. But side chains of other constituent amino acids are influenced by this amidation, and thus the synthesis cannot be performed efficiently. Accordingly, a benzhydrylamine type resin (BHA resin) of the latter type, which can provide a peptide amide at the C-terminal at the step of the acid treatment, is preferred. Note, any resin capable of providing a peptide having an amide at the C-terminal as efficiently as the above-mentioned benzhydrylamine type resin can be used.

BHA resins having a different crosslinking degree and amount introduced of the amino group are prepared and appropriately selected and used according to the intended object. Furthermore, commercially available resins can be used.

The above-mentioned resin must be activated before the synthesis, and this activation can be accomplished, for example, in the following manner.

A BHA resin is charged in a reaction vessel for the solid phase synthesis of peptides, and methylene chloride and 10% triethylamine (TEA)/methylene chloride are added and the mixture is stirred 1 to 3 times, for 5 to 10 minutes at each stirring, followed by filtration. Similarly, methylene chloride, methanol or ethanol and methylene chloride again are added and stirring is conducted in sequence (1 to 3 times for each solvent and for 1 to 3 minutes at each stirring), followed by filtration and washing.

In this synthesis process, amino acids in which an α-amino group alone or together with a functional group of the side chain is protected by a protecting group are condensed in sequence. A t-butyloxycarbonyl (Boc) group, a 9-fluorenylmethyloxycarbonyl (Fmoc) group or an equivalent group is used as the protecting group for the α-amino group.

In the case of asparagine or glutamine, in general, a Boc-amino acid or Fmoc-amino acid is directly used or is used in the form of a phenyl ester thereof, for example, a p-nitrophenyl ester. Furthermore, the amino acid having the ω-carbamide group protected by a xanthyl (Xan) group, a 4,4-dimethoxybenzhydryl (Mbh) group or an equivalent group can be used.

The ω-carboxyl group of aspartic acid or glutamic acid is protected by a benzyl ester (OBzl) group, a cyclohexyl ester group or an equivalent group.

The guanidino group of arginine or the imidazolyl group of histidine is generally protected by a p-toluene-sulfonyl (Tos) group or a dinitrophenyl (Dnp) group.

The ε-amino group of lysine is protected by a benzyloxycarbonyl (Z) group, a derivative thereof, i.e., an o-chlorobenzyloxycarbonyl (Cl-Z) group, or an equivalent group.

The alcoholic hydroxyl group of serine or threonine is generally protected by a benzyl (Bzl) group or an equivalent group.

The phenolic hydroxyl group of tyrosine is generally protected by a Bzl group, a derivative thereof such as a 2,6-dichlorobenzyl ($Cl_2$-Bzl) group, an o-bromobenzyloxycarbonyl (Br-Z) group or an equivalent group.

Furthermore, proline, alanine, glycine, leucine, isoleucine, methionine, valine, and tryptophan are generally used in the form of a Boc-amino acid or Fmoc-amino acid.

Commercially available products of these protected amino acids can be used.

The synthesis of the peptide of the present invention will now be described in detail.

(1) Introduction of Constituent Amino Acids

A BHA resin is charged in a reaction vessel equipped with an opening for adding a reagent, a solvent and the like, and a filter for recovering the solvent by filtration, and is of the type whereby a reaction is advanced by shaking the vessel as a whole or by stirring and filtration is accomplished under an elevated or reduced pressure. This reaction vessel is preferably formed of glass, Teflon-coated glass or Teflon.

To 1 g of the BHA resin is added about 2 to about 20 ml of a solvent capable of swelling the resin, such as methylene chloride, chloroform, dimethylformamide (DMF) or benzene, and resin is suspended in the solvent and then an amino acid corresponding to the C-terminal and having an α-amino group protected is added to the suspension in an amount of about 1 to about 6 equivalents per equivalent of the amino group of the resin. Stirring or shaking is conducted for about 1 to about 20 minutes, a coupling agent such as dicyclohexylcarbodiimide (DCC) is added in an amount of about 0.5 to 2 equivalents per equivalent of the protected amino acid, and stirring or shaking is carried out again.

As the coupling agent other than DCC, there can be mentioned water-soluble carbodiimide, carbonyldiimidazole, Woodward reagent "K", N-ethyl-2'-hydroxy-benzisoxazolium trifluoroborate, 1-ethoxycarbonyl-2-ethoxy-1,2-dihydroxyquinoline, Bop reagent and diphenylphosphorylazide.

Furthermore, the amino acid having an α-amino group protected can be bonded to the resin by the active ester method or the symmetric anhydride method.

The degree of advance of the coupling reaction can be monitored by the ninhydrin test or the fluororescamine test. If the reaction is not completed, the coupling reaction is repeated.

After termination of the reaction, the amino acid resin is washed 1 to several times by using at least one solvent selected from methylene chloride, chloroform, methanol, ethanol, DMF, benzene and acetic acid in an amount of about 2 to about 50 ml per gram of the BHA resin initially used, and the proline-resin is recovered by filtration.

The unreacted amino group of the washed BHA resin is blocked by the following reaction using a terminating reagent, and the resin is washed again.

As the terminating reagent, there can be used acetic anhydride, TEA/methylene chloride or chloroform, acetylimidazole/DMF, fluorescamine-diisopropylethylamine/methylene chloride and the like. The terminating reagent is used in an amount of about 0.5 to about 5 equivalents per equivalent of the amino group of the resin, and the reaction is carried out for about 10 minutes to about 18 hours.

For the coupling of the next amino acid to the C-terminal amino acid-resin, the α-amino protecting group of the C-terminal amino acid-resin is removed.

Trifluoroacetic acid (TFA) is preferred as the reagent for removing the Boc group, and is used directly (100%) or when diluted by 10% or more with methylene chloride, chloroform or an equivalent thereof.

Preferably, the TFA solution is added in an amount of about 2 to about 50 ml per gram of the initially used BHA resin, and the reaction is carried out for about 5 to about 60 minutes. After the reaction, filtration and washing with the above-mentioned washing solvent are carried out, a solution containing about 5 to about 30% of TEA in methylene chloride, chloroform or an equivalent thereof is added in an amount of about 2 to about 50 ml per gram of the initially used BHA resin to neutralize remaining TFA and washing is carried out with the above-mentioned washing solvent.

Piperidine is preferred as the reagent for removing the Fmoc group, and piperidine is diluted with methylene chloride, DMF, chloroform or an equivalent thereof and is used in the form of a solution having a concentration of 5 to 50%.

The piperidine solution is added in an amount of about 2 to about 100 ml per gram of the initially used BHA resin, and the reaction is preferably carried out for about 5 to about 60 minutes. After the reaction, filtration and washing with the above-mentioned washing solvent are carried out.

Then, another amino acid is introduced in the following manner.

A solvent is added to the obtained C-terminal amino acid-resin to form a suspension, an amino acid having the α-amino group protected is added in an amount of about 1 to about 6 equivalents per equivalent of the amino group of the resin, and then a coupling agent is added.

The degree of advance of the coupling reaction can be monitored by the ninhydrin test or the fluorescamine test.

After termination of the reaction, the resin is washed with the above-mentioned washing solvent. If the reaction is not completed, the coupling reaction is repeated, or blocking is effected by using the above-mentioned terminating reagent by the subsequent reaction.

At subsequence steps, removal of the protecting group, washing, neutralization, washing, coupling and washing are carried out in the same manner as described above except that protecting amino groups corresponding to the respective amino acids are used. Since coupling becomes difficult as the peptide chain is extended, 1-hydroxy-benzotriazole (HOBt) is preferably added to DCC, and the reaction is carried out in DMF, or the reaction is preferably carried out by adding diisopropylethylamine (DIEA) to the Bop reagent.

For the peptide having a cyclic structure formed by a linkage other than the disulfide linkage, the cyclic structure can be formed on the resin, for example, by using a process in which after completion of the coupling of the amino acid at the 1-position, the side chain of the amino acid at the 1-position and the side chain of the corresponding amino acid are bonded by the coupling procedure as mentioned above, or a process in which the corresponding amino acid, to the side chain of which the amino acid at the 1-position is bonded, is bonded to the other corresponding amino acid, to the α-amino acid of which amino acids are successively bonded.

The modification of the N-α-amino group by an acyl, alkyl or the like can be effected by a method known per se, and the peptide having no N-α-amino group can be obtained by introducing the corresponding carboxylic acid or the like into the amino acid at the 1-position.

The peptide-resin obtained by introducing the respective constituent amino acids in the above-mentioned manner is taken out from the reaction vessel and dried.

(2) Isolation of Peptide from Resin and Removal of Protecting Group

The peptide-resin is treated with hydrogen fluoride (HF) to sever the amide bond between the peptide and resin and remove the protecting group, whereby the free peptide is obtained.

A special vessel is necessary for the HF treatment, and a commercially available vessel can be used.

The dry peptide-resin is charged in the vessel, and to control the occurrence of side reactions, anisole is added in an amount of 0.5 to 5 ml per gram of the peptide-resin and the mixture is stirred. Then, liquid HF is added in an amount of 2 to 50 ml per gram of the peptide-resin and the treatment is carried out at −20 to 0° C. for 0.5 to 2 hours.

Preferably, dimethylsulfide or ethane-dithiol is added to the anisole.

After termination of the reaction, HF is removed under vacuum, and residual HF, the protecting group, anisole and other additives are removed by using a solvent such as ethyl acetate, diethyl ether or benzene. The peptide is extracted with an acidic aqueous solution such as an aqueous solution of acetic acid and the resin is recovered by filtration.

In the obtained peptide, amide is present at the C-terminal, and the peptide containing two cysteines is a non-cyclic peptide in which the disulfide linkage is not formed.

(3) Formation of Disulfide Linkage

Formation of the disulfide linkage in the peptide containing two cysteines can be accomplished by the following method.

A highly diluted alkaline aqueous solution of the peptide is oxidized by an oxidizer such as air or potassium ferricyanide to form a disulfide linkage. Furthermore, a disulfide linkage can be formed by the method of Tam [J. P. Tam, Int. J. Peptide and Protein Res., 29, 421–431 (1987)].

(4) Purification of Crude Peptide

The peptide of the present invention obtained through the above-mentioned steps contains modified peptides formed during the synthesis, oligomers formed at the cyclization and other by-products. Accordingly, purification is necessary.

More specifically, the solution extracted from the resin or the solution obtained by the cyclization treatment is concentrated by ultrafiltration and then subjected to an ion exchange treatment and a lyophilization treatment. The dry product is purified by the reversed phase high-speed liquid chromatography and then subjected to an ion exchange treatment and a gel filtration treatment, whereby a purified product is obtained.

The following 53 novel peptides have been obtained by carrying out the synthesis in the above-mentioned manner.

The structures and amino acid sequences of these 53 peptides are described below (each peptide will be indicated by the corresponding number hereinafter).

Peptide No. 1(SEQ ID NO:1):

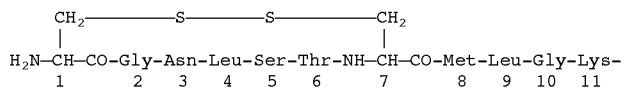
H₂N—CH—CO-Gly-Asn-Leu-Ser-Thr-NH—CH—CO-Met-Leu-Gly-Lys-
      1       2    3    4    5    6       7    8    9   10  11

Leu-Ser-Gln-Glu-Leu-His-Lys-Leu-Gln-Thr-Tyr-Pro-Gln-Thr-
12   13  14  15  16  17  18  19  20  21  22  23  24  25

Ala-Ile-Gly-Val-Gly-Ala-Pro-NH₂
26  27  28  29  30  31  32

Peptide No. 2(SEQ ID NO:2):

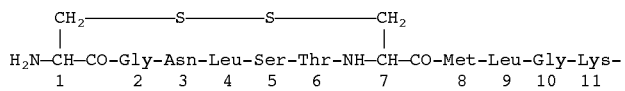
H₂N—CH—CO-Gly-Asn-Leu-Ser-Thr-NH—CH—CO-Met-Leu-Gly-Lys-
      1       2    3    4    5    6       7    8    9   10  11

Leu-Ser-Gln-Glu-Leu-His-Lys-Gln-Thr-Tyr-Pro-Gln-Thr-Ala-
12   13  14  15  16  17  18  19  20  21  22  23  24  25

Ile-Gly-Val-Gly-Ala-Pro-NH₂
26  27  28  29  30  31

Peptide No. 3(SEQ ID NO:3):

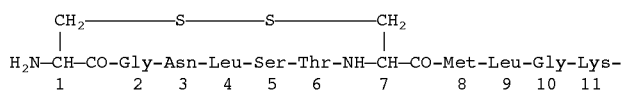
H₂N—CH—CO-Gly-Asn-Leu-Ser-Thr-NH—CH—CO-Met-Leu-Gly-Lys-
      1       2    3    4    5    6       7    8    9   10  11

Leu-Ser-Gln-Glu-Leu-His-Lys-Leu-Tyr-Pro-Gln-Thr-Ala-Ile-
12   13  14  15  16  17  18  19  20  21  22  23  24  25

Gly-Val-Gly-Ala-Pro-NH₂
26  27  28  29  30

Peptide No. 4(SEQ ID NO:4):

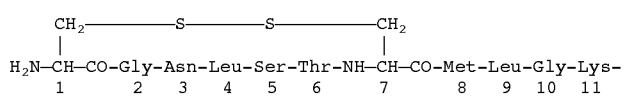
H₂N—CH—CO-Gly-Asn-Leu-Ser-Thr-NH—CH—CO-Met-Leu-Gly-Lys-
      1       2    3    4    5    6       7    8    9   10  11

Leu-Ser-Gln-Glu-Leu-His-Lys-Gly-Gln-Thr-Tyr-Pro-Gln-Thr-
12   13  14  15  16  17  18  19  20  21  22  23  24  25

Ala-Ile-Gly-Val-Gly-Ala-Pro-NH₂
26  27  28  29  30  31  32

Peptide No. 5(SEQ ID NO:5):

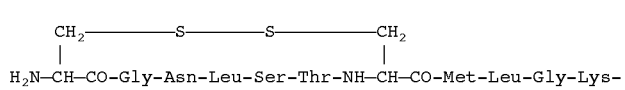
H₂N—CH—CO-Gly-Asn-Leu-Ser-Thr-NH—CH—CO-Met-Leu-Gly-Lys-
      1       2    3    4    5    6       7    8    9   10  11

Leu-Ser-Gln-Glu-Leu-His-Lys-Leu-Gln-Thr-Tyr-Pro-Gln-Thr-
12   13  14  15  16  17  18  19  20  21  22  23  24  25

Ala-Ile-Gly-Ser-Gly-Thr-Pro-NH₂
26  27  28  29  30  31  32

Peptide No. 6(SEQ ID NO:6):

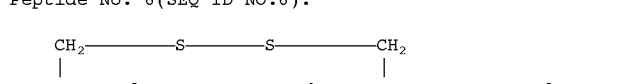
H₂N—CH—CO-Gly-Asn-Leu-Ser-Thr-NH—CH—CO-Met-Leu-Gly-Lys-
      1       2    3    4    5    6       7    8    9   10  11

Leu-Ser-Gln-Glu-Leu-His-Lys-Gln-Thr-Tyr-Pro-Gln-Thr-Ala-
12   13  14  15  16  17  18  19  20  21  22  23  24  25

Ile-Gly-Ser-Gly-Thr-Pro-NH₂
26  27  28  29  30  31

-continued

Peptide No. 7(SEQ ID NO:7):

```
      CH₂————S————S————CH₂
      |                    |
H₂N—CH—CO-Gly-Asn-Leu-Ser-Thr-NH—CH—CO-Met-Leu-Gly-Lys-
      1     2   3   4   5   6       7   8   9  10  11
```

Leu-Ser-Gln-Glu-Leu-His-Lys-Leu-Tyr-Pro-Gln-Thr-Ala-Ile-
12  13  14  15  16  17  18  19  20  21  22  23  24  25

Gly-Ser-Gly-Thr-Pro-NH₂
26  27  28  29  30

Peptide No. 8(SEQ ID NO:8):

```
      CH₂————S————S————CH₂
      |                    |
H₂N—CH—CO-Gly-Asn-Leu-Ser-Thr-NH—CH—CO-Met-Leu-Gly-Lys-
      1     2   3   4   5   6       7   8   9  10  11
```

Leu-Ser-Gln-Glu-Leu-His-Lys-Gly-Gln-Thr-Tyr-Pro-Gln-Thr-
12  13  14  15  16  17  18  19  20  21  22  23  24  25

Ala-Ile-Gly-Ser-Gly-Thr-Pro-NH₂
26  27  28  29  30  31  32

Peptide No. 9(SEQ ID NO:9)

```
      CH₂————S————S————CH₂
      |                    |
H₂N—CH—CO-Gly-Asn-Leu-Ser-Thr-NH—CH—CO-Gly-Leu-Gly-Lys-
      1     2   3   4   5   6       7   8   9  10  11
```

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 10(SEQ ID NO:10)

```
      CH₂————S————S————CH₂
      |                    |
H₂N—CH—CO-Gly-Asn-Leu-Ser-Thr-NH—CH—CO-Ala-Leu-Gly-Lys-
      1     2   3   4   5   6       7   8   9  10  11
```

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 11(SEQ ID NO:11)

```
      CH₂————S————S————CH₂
      |                    |
H₂N—CH—CO-Gly-Asn-Leu-Ser-Thr-NH—CH—CO-Val-Leu-Gly-Lys-
      1     2   3   4   5   6       7   8   9  10  11
```

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 12(SEQ ID NO:12)

```
      CH₂————S————S————CH₂
      |                    |
H₂N—CH—CO-Gly-Asn-Leu-Ser-Thr-NH—CH—CO-Pro-Leu-Gly-Lys-
      1     2   3   4   5   6       7   8   9  10  11
```

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

-continued

Peptide No. 13(SEQ ID NO:13)

```
    CH₂―――――S―――――S―――――CH₂
    |                     |
H₂N-CH-CO-Gly-Asn-Leu-Ser-Thr-NH-CH-CO-Leu-Leu-Gly-Lys-
    1      2   3   4   5   6      7   8   9   10  11
```

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 14(SEQ ID NO:14)

```
    CH₃                   CH₃
    |                     |
H₂N-CH-CO-Gly-Asn-Leu-Ser-Thr-NH-CH-CO-Met-Leu-Gly-Lys-
    1      2   3   4   5   6      7   8   9   10  11
```

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 15(SEQ ID NO:15)

```
    CH₃                   CH₃
    |                     |
H₂N-CH-CO-Gly-Asn-Leu-Ser-Thr-NH-CH-CO-Met-Leu-Gly-Lys-
    1      2   3   4   5   6      7   8   9   10  11
```

Leu-Ser-Gln-Glu-Leu-His-Lys-Gln-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 16(SEQ ID NO:16)

```
    CH₃                   CH₃
    |                     |
H₂N-CH-CO-Gly-Asn-Leu-Ser-Thr-NH-CH-CO-Met-Leu-Gly-Lys-
    1      2   3   4   5   6      7   8   9   10  11
```

Leu-Ser-Gln-Glu-Leu-His-Lys-Leu-Tyr-Pro-Gln-Thr-Ala-Ile-
12  13  14  15  16  17  18  19  20  21  22  23  24  25

Gly-Val-Gly-Ala-Pro-NH₂
26  27  28  29  30

Peptide No. 17(SEQ ID NO:17)

```
    CH₃                   CH₃
    |                     |
H₂N-CH-CO-Gly-Asn-Leu-Ser-Thr-NH-CH-CO-Met-Leu-Gly-Lys-
    1      2   3   4   5   6      7   8   9   10  11
```

Leu-Ser-Gln-Glu-Leu-His-Lys-Gly-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 18(SEQ ID NO:18)

```
    CH₃                   CH₃
    |                     |
H₂N-CH-CO-Gly-Asn-Leu-Ser-Thr-NH-CH-CO-Met-Leu-Gly-Lys-
    1      2   3   4   5   6      7   8   9   10  11
```

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Ser-Gly-Thr-Pro-NH₂
26  27  28  29  30  31  32

-continued

Peptide No. 19(SEQ ID NO:19)

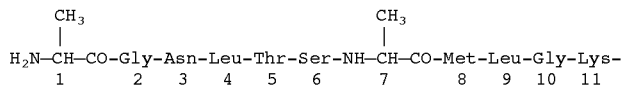
H₂N—CH—CO-Gly-Asn-Leu-Thr-Ser-NH—CH—CO-Met-Leu-Gly-Lys-
    1      2   3   4   5   6       7      8   9   10  11

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Ser-Gly-Thr-Pro-NH₂
26  27  28  29  30  31  32

Peptide No. 20(SEQ ID NO:20)

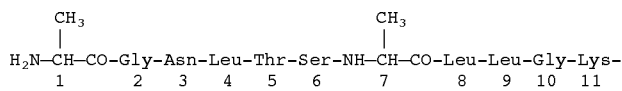
H₂N—CH—CO-Gly-Asn-Leu-Thr-Ser-NH—CH—CO-Leu-Leu-Gly-Lys-
    1      2   3   4   5   6       7      8   9   10  11

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 21(SEQ ID NO:21)

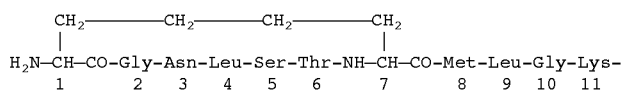
H₂N—CH—CO-Gly-Asn-Leu-Ser-Thr-NH—CH—CO-Met-Leu-Gly-Lys-
    1      2   3   4   5   6       7      8   9   10  11

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 22(SEQ ID NO:22)

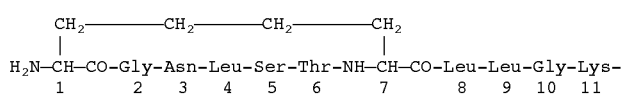
H₂N—CH—CO-Gly-Asn-Leu-Ser-Thr-NH—CH—CO-Leu-Leu-Gly-Lys-
    1      2   3   4   5   6       7      8   9   10  11

Leu-Ser-Gln-Glu-Leu-His-Lys-Leu-Gln-Thr-Tyr-Pro-Gln-Thr-
12  13  14  15  16  17  18  19  20  21  22  23  24  25

Ala-Ile-Gly-Val-Gly-Ala-Pro-NH₂
26  27  28  29  30  31  32

Peptide No. 23(SEQ ID NO:23)

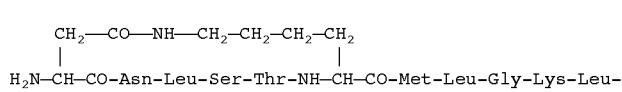
H₂N—CH—CO-Asn-Leu-Ser-Thr-NH—CH—CO-Met-Leu-Gly-Lys-Leu-
    1      2   3   4   5       6      7   8   9   10  11

Ser-Gln-Glu-Leu-His-Lys-Leu-Gln-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 24(SEQ ID NO:24)

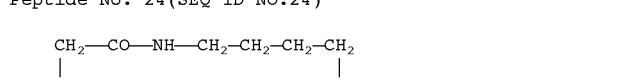
H₂N—CH—CO-Asn-Leu-Ser-Thr-NH—CH—CO-Leu-Leu-Gly-Lys-Leu-
    1      2   3   4   5       6      7   8   9   10  11

Ser-Gln-Glu-Leu-His-Lys-Leu-Gln-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 25(SEQ ID NO:25)

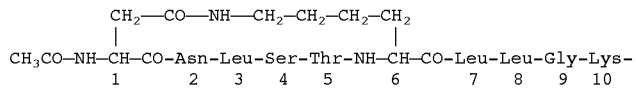
CH₃CO—NH—CH—CO-Asn-Leu-Ser-Thr-NH—CH—CO-Leu-Leu-Gly-Lys-
             1    2    3    4    5     6    7    8    9   10

Leu-Ser-Gln-Glu-Leu-His-Lys-Leu-Gln-Thr-Tyr-Pro-Gln-Thr-
11  12  13  14  15  16  17  18  19  20  21  22  23  24

Ala-Ile-Gly-Val-Gly-Ala-Pro-NH₂
25  26  27  28  29  30  31

Peptide No. 26(SEQ ID NO:26)

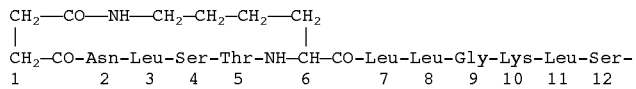
CH₂—CO-Asn-Leu-Ser-Thr-NH—CH—CO-Leu-Leu-Gly-Lys-Leu-Ser-
1      2    3    4    5     6    7    8    9   10  11  12

Gln-Glu-Leu-His-Lys-Leu-Gln-Thr-Tyr-Pro-Gln-Thr-Ala-Ile-
13  14  15  16  17  18  19  20  21  22  23  24  25  26

Gly-Val-Gly-Ala-Pro-NH₂
27  28  29  30  31

Peptide No. 27(SEQ ID NO:27)

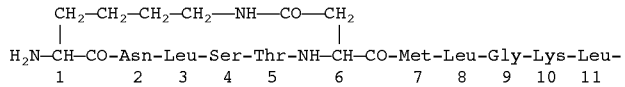
H₂N—CH—CO-Asn-Leu-Ser-Thr-NH—CH—CO-Met-Leu-Gly-Lys-Leu-
       1    2    3    4    5     6    7    8    9   10  11

Ser-Gln-Glu-Leu-His-Lys-Leu-Gln-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 28(SEQ ID NO:28)

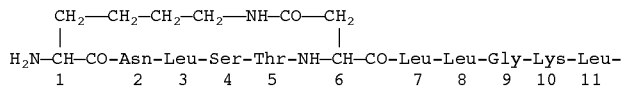
H₂N—CH—CO-Asn-Leu-Ser-Thr-NH—CH—CO-Leu-Leu-Gly-Lys-Leu-
       1    2    3    4    5     6    7    8    9   10  11

Ser-Gln-Glu-Leu-His-Lys-Leu-Gln-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 29(SEQ ID NO:29)

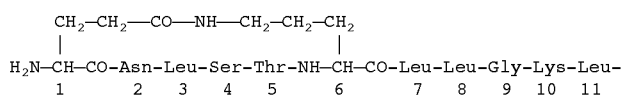
H₂N—CH—CO-Asn-Leu-Ser-Thr-NH—CH—CO-Leu-Leu-Gly-Lys-Leu-
       1    2    3    4    5     6    7    8    9   10  11

Ser-Gln-Glu-Leu-His-Lys-Leu-Gln-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 30(SEQ ID NO:30)

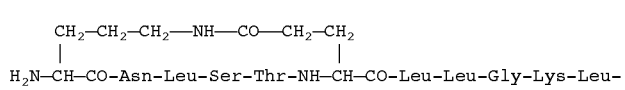
H₂N—CH—CO-Asn-Leu-Ser-Thr-NH—CH—CO-Leu-Leu-Gly-Lys-Leu-
       1    2    3    4    5     6    7    8    9   10  11

Ser-Gln-Glu-Leu-His-Lys-Leu-Gln-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 31(SEQ ID NO:31)

```
       CH₂—CO—NH—CH₂-CH₂-CH₂-CH₂
       |                        |
H₂N—CH—CO-Asn-Leu-Ser-Thr-NH—CH—CO-Leu-Leu-Gly-Lys-Leu-
   1      2   3   4   5      6   7   8   9   10  11
```

Ser-Gln-Asp-Leu-Asn-Lys-Phe-His-Thr-Tyr-Pro-Gln-Thr-Ala-
12  13  14  15  16  17  18  19  20  21  22  23  24  25

Ile-Gly-Val-Gly-Ala-Pro-NH₂
26  27  28  29  30  31

Peptide No. 32(SEQ ID NO:32)

```
CH₂—CO—NH—CH₂-CH₂-CH₂-CH₂
|                        |
CH₂—CO-Asn-Leu-Ser-Thr-NH—CH—CO-Leu-Leu-Gly-Lys-Leu-Ser-
1     2   3   4   5      6   7   8   9   10  11  12
```

Gln-Asp-Leu-Asn-Lys-Phe-His-Thr-Tyr-Pro-Gln-Thr-Ala-Ile-
13  14  15  16  17  18  19  20  21  22  23  24  25  26

Gly-Val-Gly-Ala-Pro-NH₂
27  28  29  30  31

Peptide No. 33(SEQ ID NO:33)

```
CH₂—CO—NH—CH₂-CH₂-CH₂-CH₂
|                        |
CH₂—CO-Asn-Leu-Ser-Thr-NH—CH—CO-Leu-Leu-Gly-Lys-Leu-Thr-
1     2   3   4   5      6   7   8   9   10  11  12
```

Gln-Asp-Leu-Asn-Lys-Phe-His-Thr-Tyr-Pro-Gln-Thr-Ala-Ile-
13  14  15  16  17  18  19  20  21  22  23  24  25  26

Gly-Val-Gly-Ala-Pro-NH₂
27  28  29  30  31

Peptide No. 34(SEQ ID NO:34)

```
CH₂—CO—NH—CH₂-CH₂-CH₂-CH₂
|                        |
CH₂—CO-Asn-Leu-Ser-Thr-NH—CH—CO-Met-Leu-Gly-Thr-Tyr-Thr-
1     2   3   4   5      6   7   8   9   10  11  12
```

Gln-Asp-Phe-Asn-Lys-Phe-His-Thr-Phe-Pro-Gln-Thr-Ala-Ile-
13  14  15  16  17  18  19  20  21  22  23  24  25  26

Gly-Val-Gly-Ala-Pro-NH₂
27  28  29  30  31

Peptide No. 35(SEQ ID NO:35)

```
CH₂—CO—NH—CH₂-CH₂-CH₂-CH₂
|                        |
CH₂—CO-Asn-Leu-Ser-Thr-NH—CH—CO-Val-Leu-Gly-Thr-Tyr-Thr-
1     2   3   4   5      6   7   8   9   10  11  12
```

Gln-Asp-Phe-Asn-Lys-Phe-His-Thr-Phe-Pro-Gln-Thr-Ala-Ile-
13  14  15  16  17  18  19  20  21  22  23  24  25  26

Gly-Val-Gly-Ala-Pro-NH₂
27  28  29  30  31

Peptide No. 36(SEQ ID NO:36)

```
CH₂—CO—NH—CH₂-CH₂-CH₂-CH₂
|                        |
CH₂—CO-Asn-Leu-Ser-Thr-NH—CH—CO-Leu-Leu-Gly-Thr-Tyr-Thr-
1     2   3   4   5      6   7   8   9   10  11  12
```

Gln-Asp-Phe-Asn-Lys-Phe-His-Thr-Phe-Pro-Gln-Thr-Ala-Ile-
13  14  15  16  17  18  19  20  21  22  23  24  25  26

Gly-Val-Gly-Ala-Pro-NH₂
27  28  29  30  31

Peptide No. 37(SEQ ID NO:37)

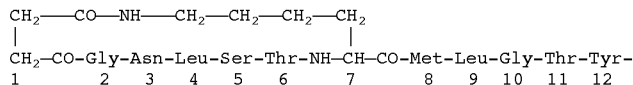
CH₂—CO-Gly-Asn-Leu-Ser-Thr-NH—CH—CO-Met-Leu-Gly-Thr-Tyr-
1      2   3   4   5   6      7      8   9   10  11  12

Thr-Gln-Asp-Phe-Asn-Lys-Phe-His-Thr-Phe-Pro-Gln-Thr-Ala-
13  14  15  16  17  18  19  20  21  22  23  24  25  26

Ile-Gly-Val-Gly-Ala-Pro-NH₂
27  28  29  30  31  32

Peptide No. 38(SEQ ID NO:38)

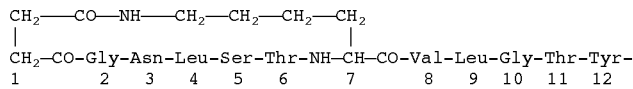
CH₂—CO-Gly-Asn-Leu-Ser-Thr-NH—CH—CO-Val-Leu-Gly-Thr-Tyr-
1      2   3   4   5   6      7      8   9   10  11  12

Thr-Gln-Asp-Phe-Asn-Lys-Phe-His-Thr-Phe-Pro-Gln-Thr-Ala-
13  14  15  16  17  18  19  20  21  22  23  24  25  26

Ile-Gly-Val-Gly-Ala-Pro-NH₂
27  28  29  30  31  32

Peptide No. 39(SEQ ID NO:39)

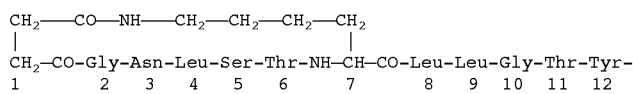
CH₂—CO-Gly-Asn-Leu-Ser-Thr-NH—CH—CO-Leu-Leu-Gly-Thr-Tyr-
1      2   3   4   5   6      7      8   9   10  11  12

Thr-Gln-Asp-Phe-Asn-Lys-Phe-His-Thr-Phe-Pro-Gln-Thr-Ala-
13  14  15  16  17  18  19  20  21  22  23  24  25  26

Ile-Gly-Val-Gly-Ala-Pro-NH₂
27  28  29  30  31  32

Peptide No. 40(SEQ ID NO:40)

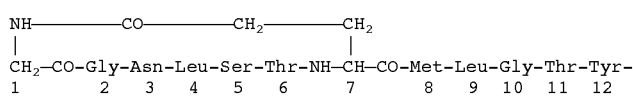
CH₂—CO-Gly-Asn-Leu-Ser-Thr-NH—CH—CO-Met-Leu-Gly-Thr-Tyr-
1      2   3   4   5   6      7      8   9   10  11  12

Thr-Gln-Asp-Phe-Asn-Lys-Phe-His-Thr-Phe-Pro-Gln-Thr-Ala-
13  14  15  16  17  18  19  20  21  22  23  24  25  26

Ile-Gly-Val-Gly-Ala-Pro-NH₂
27  28  29  30  31  32

Peptide No. 41(SEQ ID NO:41)

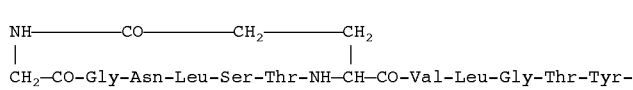
CH₂—CO-Gly-Asn-Leu-Ser-Thr-NH—CH—CO-Val-Leu-Gly-Thr-Tyr-
1      2   3   4   5   6      7      8   9   10  11  12

Thr-Gln-Asp-Phe-Asn-Lys-Phe-His-Thr-Phe-Pro-Gln-Thr-Ala-
13  14  15  16  17  18  19  20  21  22  23  24  25  26

Ile-Gly-Val-Gly-Ala-Pro-NH₂
27  28  29  30  31  32

Peptide No. 42(SEQ ID NO:42)

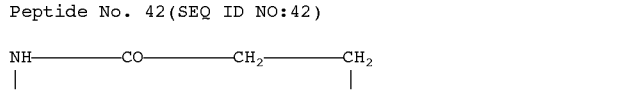
CH₂—CO-Gly-Asn-Leu-Ser-Thr-NH—CH—CO-Leu-Leu-Gly-Thr-Tyr-
1      2   3   4   5   6      7      8   9   10  11  12

Thr-Gln-Asp-Phe-Asn-Lys-Phe-His-Thr-Phe-Pro-Gln-Thr-Ala-
13  14  15  16  17  18  19  20  21  22  23  24  25  26

Ile-Gly-Val-Gly-Ala-Pro-NH₂
27  28  29  30  31  32

Peptide No. 43(SEQ ID NO:43)

```
CH₂—CO—NH—CH₂—CH₂—CH₂—CH₂
 |                          |
CH₂-CO-Asn-Leu-Ser-Thr-NH-CH-CO-Val-Leu-Gly-Lys-Leu-Ser-
 1      2   3   4   5      6     7   8   9   10  11  12
```

Gln-Glu-Leu-His-Lys-Leu-Gln-Thr-Tyr-Pro-Arg-Thr-Asn-Thr-
13  14  15  16  17  18  19  20  21  22  23  24  25  26

Gly-Ser-Gly-Thr-Pro-NH₂
27  28  29  30  31

Peptide No. 44(SEQ ID NO:44)

```
CH₂—CO—NH—CH₂—CH₂—CH₂—CH₂
 |                          |
CH₂-CO-Asn-Leu-Ser-Thr-NH-CH-CO-Val-Leu-Gly-Lys-Leu-Ser-
 1      2   3   4   5      6     7   8   9   10  11  12
```

Gln-Glu-Leu-His-Lys-Gln-Thr-Tyr-Pro-Arg-Thr-Asn-Thr-Gly-
13  14  15  16  17  18  19  20  21  22  23  24  25  26

Ser-Gly-Thr-Pro-NH₂
27  28  29  30

Peptide No. 45(SEQ ID NO:45)

```
NH————CO————CH₂————CH₂
 |                     |
CH₂-CO-Ser-Asn-Leu-Ser-Thr-NH-CH-CO-Val-Leu-Gly-Lys-Leu-
 1     2   3   4   5   6      7     8   9   10  11  12
```

Ser-Gln-Glu-Leu-His-Lys-Leu-Gln-Thr-Tyr-Pro-Arg-Thr-Asn-
13  14  15  16  17  18  19  20  21  22  23  24  25  26

Thr-Gly-Ser-Gly-Thr-Pro-NH₂
27  28  29  30  31  32

Peptide No. 46(SEQ ID NO:46)

```
NH————CO————CH₂————CH₂
 |                     |
CH₂-CO-Ser-Asn-Leu-Ser-Thr-NH-CH-CO-Val-Leu-Gly-Lys-Leu-
 1     2   3   4   5   6      7     8   9   10  11  12
```

Ser-Gln-Glu-Leu-His-Lys-Gln-Thr-Tyr-Pro-Arg-Thr-Asn-Thr-
13  14  15  16  17  18  19  20  21  22  23  24  25  26

Gly-Ser-Gly-Thr-Pro-NH₂
27  28  29  30  31

Peptide No. 47(SEQ ID NO:47)

```
CH₂—CO—NH—CH₂—CH₂—CH₂—CH₂
 |                          |
CH₂-CO-Asn-Leu-Ser-Thr-NH-CH-CO-Val-Leu-Gly-Lys-Leu-Ser-
 1      2   3   4   5      6     7   8   9   10  11  12
```

Gln-Glu-Leu-His-Lys-Leu-Gln-Thr-Tyr-Pro-Arg-Thr-Asp-Val-
13  14  15  16  17  18  19  20  21  22  23  24  25  26

Gly-Ala-Gly-Thr-Pro-NH₂
27  28  29  30  31

Peptide No. 48(SEQ ID NO:48)

```
NH————CO————CH₂————CH₂
 |                     |
CH₂-CO-Ser-Asn-Leu-Ser-Thr-NH-CH-CO-Val-Leu-Gly-Lys-Leu-
 1     2   3   4   5   6      7     8   9   10  11  12
```

Ser-Gln-Glu-Leu-His-Lys-Leu-Gln-Thr-Tyr-Pro-Arg-Thr-Asp-
13  14  15  16  17  18  19  20  21  22  23  24  25  26

Val-Gly-Ala-Gly-Thr-Pro-NH₂
27  28  29  30  31  32

-continued

Peptide No. 49(SEQ ID NO:49)

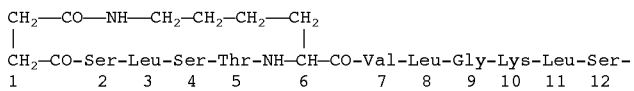
```
CH₂—CO—NH—CH₂—CH₂—CH₂—CH₂
 |                          |
CH₂-CO-Ser-Leu-Ser-Thr-NH—CH—CO-Val-Leu-Gly-Lys-Leu-Ser-
1      2   3   4   5       6    7   8   9   10  11  12
```

Gln-Glu-Leu-His-Lys-Leu-Gln-Thr-Tyr-Pro-Arg-Thr-Asp-Val-
13  14  15  16  17  18  19  20  21  22  23  24  25  26

Gly-Ala-Gly-Thr-Pro-NH₂
27  28  29  30  31

Peptide No. 50(SEQ ID NO:50)

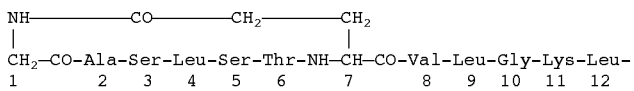
```
NH————CO————CH₂————CH₂
 |                    |
CH₂-CO-Ala-Ser-Leu-Ser-Thr-NH—CH—CO-Val-Leu-Gly-Lys-Leu-
1      2   3   4   5   6       7    8   9   10  11  12
```

Ser-Gln-Glu-Leu-His-Lys-Leu-Gln-Thr-Tyr-Pro-Arg-Thr-Asp-
13  14  15  16  17  18  19  20  21  22  23  24  25  26

Val-Gly-Ala-Gly-Thr-Pro-NH₂
27  28  29  30  31  32

Peptide No. 51(SEQ ID NO:51)

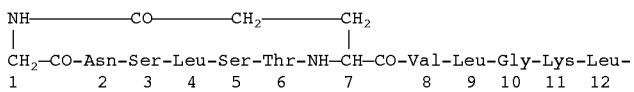
```
NH————CO————CH₂————CH₂
 |                    |
CH₂-CO-Asn-Ser-Leu-Ser-Thr-NH—CH—CO-Val-Leu-Gly-Lys-Leu-
1      2   3   4   5   6       7    8   9   10  11  12
```

Ser-Gln-Glu-Leu-His-Lys-Leu-Gln-Thr-Tyr-Pro-Arg-Thr-Asp-
13  14  15  16  17  18  19  20  21  22  23  24  25  26

Val-Gly-Ala-Gly-Thr-Pro-NH₂
27  28  29  30  31  32

Peptide No. 52(SEQ ID NO:52)

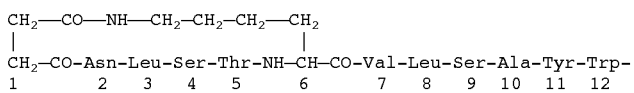
```
CH₂—CO—NH—CH₂-CH₂-CH₂—CH₂
 |                       |
CH₂-CO-Asn-Leu-Ser-Thr-NH—CH—CO-Val-Leu-Ser-Ala-Tyr-Trp-
1      2   3   4   5      6    7   8   9   10  11  12
```

Arg-Asn-Leu-Asn-Asn-Phe-His-Arg-Phe-Ser-Gly-Met-Gly-Phe-
13  14  15  16  17  18  19  20  21  22  23  24  25  26

Gly-Pro-Glu-Thr-Pro-NH₂
27  28  29  30  31

Peptide No. 53(SEQ ID NO:53)

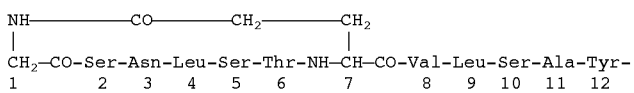
```
NH————CO————CH₂————CH₂
 |                    |
CH₂-CO-Ser-Asn-Leu-Ser-Thr-NH—CH—CO-Val-Leu-Ser-Ala-Tyr-
1      2   3   4   5   6       7    8   9   10  11  12
```

Tyr-Arg-Asn-Leu-Asn-Asn-Phe-His-Arg-Phe-Ser-Gly-Met-Gly-
13  14  15  16  17  18  19  20  21  22  23  24  25  26

Phe-Gly-Pro-Glu-Thr-Pro-NH₂
27  28  29  30  31  32

The results of the amino acid analysis of the peptide of the present invention obtained by the above-mentioned synthesis process are shown in Table 1.

In Table 1, each upper value is a found value, and each lower parenthesized value is a theoretical value.

TABLE 1

|     | 1 | 2 | 3 | 4 | 5 | 6 | 7 | 8 | 9 |
| --- | --- | --- | --- | --- | --- | --- | --- | --- | --- |
| Asp | 1.00 | 1.00 | 1.01 | 1.07 | 1.02 | 1.00 | 0.99 | 1.00 | 1.02 |
|     | (1) | (1) | (1) | (1) | (1) | (1) | (1) | (1) | (1) |

TABLE 1-continued

| Thr | 2.80 | 2.64 | 1.89 | 2.69 | 3.56 | 3.64 | 2.75 | 3.57 | 2.62 |
| --- | --- | --- | --- | --- | --- | --- | --- | --- | --- |
|     | (3) | (3) | (2) | (3) | (4) | (4) | (3) | (4) | (3) |
| Ser | 1.82 | 1.59 | 1.80 | 1.72 | 2.53 | 2.74 | 2.64 | 2.64 | 1.70 |
|     | (2) | (2) | (2) | (2) | (3) | (3) | (3) | (3) | (2) |
| Glu | 4.05 | 4.00 | 3.08 | 3.97 | 4.08 | 4.14 | 3.11 | 4.10 | 4.03 |
|     | (4) | (4) | (3) | (4) | (4) | (4) | (3) | (4) | (4) |
| Pro | 1.98 | 2.12 | 2.17 | 2.03 | 1.90 | 2.01 | 2.02 | 2.08 | 2.09 |
|     | (2) | (2) | (2) | (2) | (2) | (2) | (2) | (2) | (2) |
| Gly | 3.94 | 3.90 | 3.93 | 4.96 | 3.91 | 3.85 | 3.90 | 4.89 | 4.90 |
|     | (4) | (4) | (4) | (5) | (4) | (4) | (4) | (5) | (5) |

TABLE 1-continued

|  |  |  |  |  |  |  |  |  |  |
|---|---|---|---|---|---|---|---|---|---|
| Ala | 2.00 (2) | 2.01 (2) | 2.02 (2) | 2.01 (2) | 0.98 (1) | 1.00 (1) | 0.99 (1) | 1.00 (1) | 2.02 (2) |
| Cys | 1.65 (2) | 1.62 (2) | 1.65 (2) | 1.64 (2) | 1.64 (2) | 1.50 (2) | 1.61 (2) | 1.52 (2) | 1.74 (2) |
| Met | 1.01 (1) | 1.00 (1) | 0.96 (1) | 0.91 (1) | 1.05 (1) | 0.90 (1) | 0.99 (1) | 0.99 (1) | — |
| Ile | 1.02 (1) | 1.05 (1) | 0.98 (1) | 0.91 (1) | 1.13 (1) | 1.10 (1) | 1.10 (1) | 1.10 (1) | 1.01 (1) |
| Leu | 4.99 (5) | 4.12 (4) | 4.95 (5) | 3.92 (4) | 5.16 (5) | 4.16 (4) | 5.17 (5) | 4.14 (4) | 5.20 (5) |
| Tyr | 0.97 (1) | 1.10 (1) | 0.93 (1) | 1.06 (1) | 1.22 (1) | 1.15 (1) | 1.14 (1) | 0.98 (1) | 1.08 (1) |
| Lys | 2.00 (2) | 1.97 (2) | 1.96 (2) | 1.96 (2) | 2.01 (2) | 2.00 (2) | 2.02 (2) | 2.01 (2) | 2.03 (2) |
| His | 1.04 (1) | 1.03 (1) | 1.00 (1) | 0.96 (1) | 0.97 (1) | 1.03 (1) | 0.99 (1) | 0.98 (1) | 0.99 (1) |
| Val | 1.01 (1) | 0.99 (1) | 1.01 (1) | 1.10 (1) | — | — | — | — | 1.08 (1) |
| Asu | — | — | — | — | — | — | — | — | — |
| Ornithine | — | — | — | — | — | — | — | — | — |
| Phe | — | — | — | — | — | — | — | — | — |
| Arg | — | — | — | — | — | — | — | — | — |
| Trp | — | — | — | — | — | — | — | — | - |

|  | 10 | 11 | 12 | 13 | 14 | 15 | 16 | 17 | 18 |
|---|---|---|---|---|---|---|---|---|---|
| Asp | 1.01 (1) | 0.99 (1) | 1.02 (1) | 1.02 (1) | 1.03 (1) | 1.00 (1) | 1.02 (1) | 1.00 (1) | 1.02 (1) |
| Thr | 2.59 (3) | 2.66 (3) | 2.62 (3) | 2.62 (3) | 2.74 (3) | 2.78 (3) | 1.92 (2) | 2.74 (3) | 3.60 (4) |
| Ser | 1.72 (2) | 1.79 (2) | 1.68 (2) | 1.72 (2) | 1.64 (2) | 1.69 (2) | 1.82 (2) | 1.64 (2) | 2.73 (3) |
| Glu | 3.96 (4) | 4.03 (4) | 4.00 (4) | 3.99 (4) | 4.08 (4) | 4.09 (4) | 3.05 (3) | 4.12 (4) | 4.03 (4) |
| Pro | 2.05 (2) | 2.10 (2) | 3.19 (3) | 2.09 (2) | 2.02 (2) | 2.00 (2) | 2.04 (2) | 2.00 (2) | 2.04 (2) |
| Gly | 3.99 (4) | 3.94 (4) | 3.93 (4) | 3.90 (4) | 4.00 (4) | 3.99 (4) | 4.01 (4) | 4.95 (5) | 3.96 (4) |
| Ala | 3.03 (3) | 2.04 (2) | 2.04 (2) | 2.09 (2) | 3.84 (4) | 3.89 (4) | 3.87 (4) | 3.90 (4) | 2.98 (3) |
| Cys | 1.62 (2) | 1.75 (2) | 1.80 (2) | 1.73 (2) | — | — | — | — | — |
| Met | — | — | — | — | 1.17 (1) | 1.08 (1) | 1.10 (1) | 1.13 (1) | 0.99 (1) |
| Ile | 1.02 (1) | 0.94 (1) | 0.97 (1) | 0.96 (1) | 1.12 (1) | 1.07 (1) | 1.04 (1) | 1.11 (1) | 0.93 (1) |
| Leu | 4.94 (5) | 5.10 (5) | 5.14 (5) | 6.05 (6) | 5.33 (5) | 4.23 (4) | 5.25 (5) | 4.32 (4) | 5.16 (5) |
| Tyr | 0.95 (1) | 0.74 (1) | 0.94 (1) | 0.89 (1) | 1.33 (1) | 1.17 (1) | 1.01 (1) | 1.22 (1) | 0.74 (1) |
| Lys | 2.01 (2) | 2.01 (2) | 2.01 (2) | 2.00 (2) | 2.02 (2) | 2.03 (2) | 2.01 (2) | 2.03 (2) | 2.01 (2) |
| His | 1.05 (1) | 1.05 (1) | 0.99 (1) | 1.08 (1) | 1.08 (1) | 1.07 (1) | 1.07 (1) | 1.09 (1) | 0.96 (1) |
| Val | 1.06 (1) | 2.06 (2) | 1.10 (1) | 1.09 (1) | 1.01 (1) | 1.06 (1) | 1.05 (1) | 1.01 (1) | — |
| Asu | — | — | — | — | — | — | — | — | — |
| Ornithine | — | — | — | — | — | — | — | — | — |
| Phe | — | — | — | — | — | — | — | — | — |
| Arg | — | — | — | — | — | — | — | — | — |
| Trp | — | — | — | — | — | — | — | — | - |

|  | 19 | 20 | 21 | 22 | 23 | 24 | 25 | 26 | 27 |
|---|---|---|---|---|---|---|---|---|---|
| Asp | 1.01 (1) | 1.03 (1) | 1.02 (1) | 1.02 (1) | 1.94 (2) | 1.94 (2) | 1.88 (2) | 1.00 (1) | 1.98 (2) |
| Thr | 3.60 (4) | 2.78 (3) | 2.62 (3) | 2.65 (3) | 2.77 (3) | 2.80 (3) | 2.81 (3) | 2.67 (3) | 2.78 (3) |
| Ser | 2.76 (3) | 1.76 (2) | 1.71 (2) | 1.99 (2) | 1.71 (2) | 1.70 (2) | 1.97 (2) | 1.90 (2) | 1.71 (2) |
| Glu | 4.02 (4) | 4.06 (4) | 4.06 (4) | 4.03 (4) | 4.13 (4) | 4.08 (4) | 4.16 (4) | 4.08 (4) | 4.13 (4) |
| Pro | 2.02 (2) | 2.02 (2) | 2.02 (2) | 1.79 (2) | 2.05 (2) | 2.06 (2) | 1.93 (2) | 1.81 (2) | 2.04 (2) |
| Gly | 3.95 (4) | 3.98 (4) | 3.96 (4) | 3.97 (4) | 3.02 (3) | 3.06 (3) | 3.10 (3) | 2.98 (3) | 2.98 (3) |

|  | 28 | 29 | 30 | 31 | 32 | 33 | 34 | 35 | 36 |
|---|---|---|---|---|---|---|---|---|---|
| Ala | 2.97 (3) | 3.96 (4) | 1.98 (2) | 1.94 (2) | 2.01 (2) | 2.01 (2) | 1.97 (2) | 1.94 (2) | 1.99 (2) |
| Cys | — | — | — | — | — | — | — | — | — |
| Met | 1.02 (1) | 1.02 (1) | 1.10 (1) | — | 1.03 (1) | — | — | — | 1.10 (1) |
| Ile | 0.93 (1) | 0.99 (1) | 1.03 (1) | 0.98 (1) | 1.07 (1) | 0.98 (1) | 1.04 (1) | 1.01 (1) | 1.16 (1) |
| Leu | 5.08 (5) | 6.09 (6) | 5.43 (5) | 6.26 (6) | 5.19 (5) | 6.09 (6) | 6.44 (6) | 6.29 (6) | 5.25 (5) |
| Tyr | 0.76 (1) | 0.96 (1) | 1.12 (1) | 0.96 (1) | 0.98 (1) | 0.97 (1) | 0.96 (1) | 0.97 (1) | 1.04 (1) |
| Lys | 2.03 (2) | 1.96 (2) | 1.96 (2) | 2.04 (2) | 2.91 (3) | 2.91 (3) | 2.96 (3) | 2.99 (3) | 2.92 (3) |
| His | 0.96 (1) | 1.09 (1) | 1.10 (1) | 1.02 (1) | 1.03 (1) | 1.17 (1) | 1.01 (1) | 1.04 (1) | 1.13 (1) |
| Val | — | — | 0.97 (1) | 1.04 (1) | 1.01 (1) | 1.19 (1) | 1.12 (1) | 1.03 (1) | 1.09 (1) |
| Asu | — | — | 1.63 (2) | 1.62 (2) | — | — | — | — | — |
| Ornithine | — | — | — | — | — | — | — | — | — |
| Phe | — | — | — | — | — | — | — | — | — |
| Arg | — | — | — | — | — | — | — | — | — |
| Trp | — | — | — | — | — | — | — | — | - |

|  | 28 | 29 | 30 | 31 | 32 | 33 | 34 | 35 | 36 |
|---|---|---|---|---|---|---|---|---|---|
| Asp | 1.94 (2) | 0.99 (1) | 0.97 (1) | 3.85 (4) | 3.01 (3) | 2.97 (3) | 2.99 (3) | 2.96 (3) | 2.91 (3) |
| Thr | 2.77 (3) | 2.75 (3) | 2.64 (3) | 2.67 (3) | 2.87 (3) | 3.62 (4) | 4.75 (5) | 4.65 (5) | 4.52 (5) |
| Ser | 1.73 (2) | 1.88 (2) | 1.73 (2) | 1.94 (2) | 1.78 (2) | 0.89 (1) | 0.90 (1) | 0.93 (1) | 0.84 (1) |
| Glu | 4.09 (4) | 5.16 (5) | 5.15 (5) | 2.07 (2) | 2.01 (2) | 2.00 (2) | 2.04 (2) | 2.02 (2) | 2.06 (2) |
| Pro | 1.99 (2) | 1.92 (2) | 1.92 (2) | 2.00 (2) | 1.97 (2) | 2.08 (2) | 1.95 (2) | 2.01 (2) | 2.02 (2) |
| Gly | 2.96 (3) | 3.01 (3) | 3.05 (3) | 3.03 (3) | 3.02 (3) | 3.07 (3) | 2.97 (3) | 2.99 (3) | 3.02 (3) |
| Ala | 2.14 (2) | 2.00 (2) | 2.01 (2) | 1.99 (2) | 1.99 (2) | 1.98 (2) | 1.96 (2) | 2.02 (2) | 2.01 (2) |
| Cys | — | — | — | — | — | — | — | — | — |
| Met | — | — | — | — | — | — | 1.08 (1) | — | — |
| Ile | 0.99 (1) | 0.99 (1) | 1.09 (1) | 1.02 (1) | 1.01 (1) | 0.99 (1) | 1.02 (1) | 1.01 (1) | 1.03 (1) |
| Leu | 6.07 (6) | 6.33 (6) | 6.42 (6) | 5.36 (5) | 5.19 (5) | 5.14 (5) | 2.02 (2) | 2.06 (2) | 3.15 (3) |
| Tyr | 0.95 (1) | 0.97 (1) | 0.94 (1) | 0.99 (1) | 1.01 (1) | 1.14 (1) | 1.11 (1) | 0.90 (1) | 0.98 (1) |
| Lys | 2.87 (3) | 1.91 (2) | 1.89 (2) | 3.05 (3) | 3.00 (3) | 2.95 (3) | 2.02 (2) | 2.03 (2) | 1.98 (2) |
| His | 1.09 (1) | 1.02 (1) | 1.02 (1) | 1.03 (1) | 1.12 (1) | 0.98 (1) | 1.03 (1) | 0.99 (1) | 1.07 (1) |
| Val | 1.01 (1) | 1.05 (1) | 1.04 (1) | 1.10 (1) | 1.06 (1) | 1.05 (1) | 1.00 (1) | 2.10 (1) | 1.01 (1) |
| Asu | — | — | — | — | — | — | — | — | — |
| Ornithine | — | 1.22 (1) | 1.21 (1) | — | — | — | — | — | — |
| Phe | — | — | — | 1.06 (1) | 1.02 (1) | 1.00 (1) | 3.11 (3) | 2.85 (3) | 2.99 (3) |
| Arg | — | — | — | — | — | — | — | — | — |
| Trp | — | — | — | — | — | — | — | — | - |

|  | 37 | 38 | 39 | 40 | 41 | 42 | 43 | 44 | 45 |
|---|---|---|---|---|---|---|---|---|---|
| Asp | 3.02 (3) | 3.01 (3) | 2.98 (3) | 3.02 (3) | 2.94 (3) | 2.96 (3) | 1.94 (2) | 1.94 (2) | 1.98 (2) |
| Thr | 4.58 (5) | 4.66 (5) | 4.72 (5) | 4.64 (5) | 4.65 (5) | 4.56 (5) | 4.62 (5) | 4.54 (5) | 4.70 (5) |
| Ser | 0.88 (1) | 0.86 (1) | 0.92 (1) | 0.87 (1) | 0.89 (1) | 0.89 (1) | 2.67 (3) | 2.74 (3) | 3.64 (4) |
| Glu | 2.04 (2) | 2.03 (2) | 2.06 (2) | 3.10 (3) | 3.07 (3) | 3.01 (3) | 3.00 (3) | 3.05 (3) | 4.08 (4) |
| Pro | 2.09 (2) | 2.06 (2) | 2.00 (2) | 1.92 (2) | 1.99 (2) | 2.01 (2) | 2.05 (2) | 2.06 (2) | 2.00 (2) |
| Gly | 3.99 (4) | 3.90 (4) | 3.95 (4) | 4.85 (5) | 4.93 (5) | 4.96 (5) | 3.02 (3) | 2.98 (3) | 3.01 (3) |

TABLE 1-continued

|     | | | | | | | | | |
|-----|---|---|---|---|---|---|---|---|---|
| Ala | 2.00 (2) | 2.06 (2) | 1.99 (2) | 2.03 (2) | 2.04 (2) | 2.01 (2) | — | — | — |
| Cys | — | — | — | — | — | — | — | — | — |
| Met | 1.00 (1) | — | — | 1.03 (1) | — | — | — | — | — |
| Ile | 1.08 (1) | 0.96 (1) | 0.99 (1) | 1.00 (1) | 1.07 (1) | 1.06 (1) | — | — | — |
| Leu | 2.10 (2) | 2.08 (2) | 3.08 (3) | 2.12 (2) | 2.07 (2) | 3.17 (3) | 5.00 (5) | 4.05 (4) | 5.20 (5) |
| Tyr | 0.86 (1) | 1.01 (1) | 1.12 (1) | 1.05 (1) | 1.01 (1) | 0.95 (1) | 0.99 (1) | 0.93 (1) | 1.04 (1) |
| Lys | 1.97 (2) | 2.00 (2) | 2.01 (2) | 1.00 (1) | 0.99 (1) | 0.98 (1) | 2.93 (3) | 2.90 (3) | 2.01 (2) |
| His | 1.09 (1) | 0.99 (1) | 1.04 (1) | 1.06 (1) | 1.07 (1) | 1.05 (1) | 1.00 (1) | 1.09 (1) | 1.09 (1) |
| Val | 1.08 (1) | 2.08 (2) | 1.09 (1) | 1.10 (1) | 2.12 (2) | 1.04 (1) | 1.05 (1) | 1.02 (1) | 1.01 (1) |
| Asu | — | — | — | — | — | — | — | — | — |
| Orni-thine | — | — | — | — | — | — | — | — | — |
| Phe | 3.08 (3) | 3.12 (3) | 3.01 (3) | 2.89 (3) | 2.95 (3) | 2.99 (3) | — | — | — |
| Arg | — | — | — | — | — | — | 1.01 (1) | 0.94 (1) | 1.05 (1) |
| Trp | — | — | — | — | — | — | — | — | — |

|     | 46 | 47 | 48 | 49 | 50 | 51 | 52 | 53 |
|-----|----|----|----|----|----|----|----|-----|
| Asp | 1.90 (2) | 1.92 (2) | 1.94 (2) | 1.00 (1) | 1.01 (1) | 1.94 (2) | 3.96 (4) | 4.01 (4) |
| Thr | 4.66 (5) | 3.56 (4) | 3.60 (4) | 3.64 (4) | 3.62 (4) | 3.54 (4) | 1.87 (2) | 1.85 (2) |
| Ser | 3.58 (4) | 1.76 (2) | 2.72 (3) | 2.58 (3) | 2.64 (3) | 2.70 (3) | 2.68 (3) | 3.70 (4) |
| Glu | 4.06 (4) | 3.06 (3) | 4.11 (4) | 3.05 (3) | 4.09 (4) | 4.06 (4) | 1.02 (1) | 2.03 (2) |
| Pro | 1.97 (2) | 2.02 (2) | 2.02 (2) | 1.93 (2) | 1.99 (2) | 2.01 (2) | 2.03 (2) | 1.99 (2) |
| Gly | 3.07 (3) | 3.05 (3) | 3.93 (4) | 2.99 (3) | 3.97 (4) | 3.91 (4) | 3.03 (3) | 3.92 (4) |
| Ala | — | 0.98 (1) | 1.01 (1) | 1.00 (1) | 2.01 (2) | 0.99 (1) | 1.00 (1) | 0.99 (1) |
| Cys | — | — | — | — | — | — | — | — |
| Met | — | — | — | — | — | — | 0.96 (1) | 1.09 (1) |
| Ile | — | — | — | — | — | — | — | — |
| Leu | 4.02 (4) | 5.25 (5) | 5.16 (5) | 5.28 (5) | 5.08 (5) | 5.19 (5) | 3.09 (3) | 3.02 (3) |
| Tyr | 0.89 (1) | 1.07 (1) | 1.05 (1) | 0.99 (1) | 0.94 (1) | 1.00 (1) | 1.02 (1) | 1.04 (1) |
| Lys | 1.98 (2) | 2.95 (3) | 1.95 (2) | 2.88 (3) | 2.00 (2) | 2.03 (2) | 1.02 (1) | — |
| His | 1.02 (1) | 1.03 (1) | 0.99 (1) | 1.04 (1) | 1.05 (1) | 1.07 (1) | 0.99 (1) | 1.04 (1) |
| Val | 1.09 (1) | 2.18 (2) | 2.02 (2) | 2.04 (2) | 2.14 (2) | 2.09 (2) | 1.05 (1) | 1.07 (1) |
| Asu | — | — | — | — | — | — | — | — |
| Orni-thine | — | — | — | — | — | — | — | — |
| Phe | — | — | — | — | — | — | 2.99 (3) | 3.01 (3) |
| Arg | 1.02 (1) | 0.99 (1) | 0.98 (1) | 1.03 (1) | 1.00 (1) | 1.02 (1) | 1.99 (2) | 2.05 (2) |
| Trp | — | — | — | — | — | — | 0.85 (1) | 0.88 (1) |

The peptide of the present invention has an excellent function of reducing the level of calcium in serum, and the peptide of the present invention is effective for the remedy of diseases caused by abnormal calcium metabolism in the body, such as hypercalcemia and osteoporosis. This will now be described with the following test.

Test 1

Six-weeks-old female rats of the Wistar strain (each group consisting of 4 rats) were used as the test animal, and the peptides of the present invention obtained in the examples given hereinafter were tested at concentrations adjusted with a 1% aqueous solution of sodium acetate (pH 4,0) to which 0.1% bovine serum albumin (BSA) was added.

The solution was adjusted to a concentration of 166 μg/ml 830 ng/ml or 83 ng/ml and administered with the tail vein in an amount of 1 ml/kg.

The back of the rat was fixed and blood was collected just before the administration, and at predetermined intervals after the administration, from the neck vein. The amount of blood collected each time was 0.3 ml. The sampled blood was subjected to centrifugal separation at 3500 rpm for 20 minutes to separate serum and the calcium content in the separated serum was measured by TBA-380 (supplied by Toshiba) using a Wako calcium-measuring kit (o-cpc method), and the ratio of reduction of the calcium concentration in the serum was determined.

The results are shown in Tables 2–10.

TABLE 2

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 89.0 | 93.7 | 95.2 | 87.5 |
| 1 | 830 | 100.0 | 85.6 | 81.6 | 76.8 | 88.5 |
| 2 | 830 | 100.0 | 86.7 | 87.7 | 92.8 | 90.1 |
| 3 | 830 | 100.0 | 97.0 | 94.9 | 86.4 | 89.9 |
| 4 | 830 | 100.0 | 90.5 | 92.0 | 95.5 | 86.7 |

TABLE 3

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 100.0 | 100.0 | 91.8 | 88.1 |
| 14 | 166 | 100.0 | 76.0 | 70.0 | 74.3 | 73.7 |
| 15 | 166 | 100.0 | 75.5 | 67.5 | 80.6 | 75.3 |
| 16 | 166 | 100.0 | 80.0 | 86.5 | 84.8 | 85.7 |
| 17 | 166 | 100.0 | 77.6 | 71.5 | 79.7 | 83.2 |

TABLE 4

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 100.0 | 98.3 | 100.0 | 97.6 |
| 1 | 830 | 100.0 | 74.3 | 68.4 | 68.0 | 84.8 |
| 5 | 830 | 100.0 | 76.4 | 74.2 | 70.7 | 76.4 |
| 6 | 830 | 100.0 | 73.1 | 68.1 | 74.6 | 92.1 |
| 7 | 830 | 100.0 | 81.9 | 91.7 | 97.4 | 100.0 |
| 8 | 830 | 100.0 | 76.6 | 78.2 | 99.7 | 96.3 |

TABLE 5

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 93.7 | 88.1 | 85.5 | 82.5 |
| 9 | 83 | 100.0 | 81.0 | 87.5 | 84.0 | 83.2 |
| | 830 | 100.0 | 72.8 | 78.4 | 86.8 | 82.4 |
| 10 | 83 | 100.0 | 68.7 | 77.9 | 90.6 | 81.6 |
| | 830 | 100.0 | 70.2 | 65.4 | 76.1 | 84.2 |
| 11 | 83 | 100.0 | 69.7 | 82.8 | 83.9 | 81.0 |
| | 830 | 100.0 | 69.1 | 62.7 | 77.2 | 86.2 |

TABLE 5-continued

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| 12 | 83 | 100.0 | 88.0 | 92.4 | 83.4 | 84.0 |
| | 830 | 109.0 | 77.0 | 86.8 | 85.8 | 88.0 |
| 13 | 83 | 100.0 | 68.9 | 70.5 | 84.4 | 86.8 |
| | 830 | 100.0 | 71.3 | 62.7 | 58.3 | 61.8 |

TABLE 6

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 100.0 | 98.3 | 100.0 | 97.6 |
| 21 | 83 | 100.0 | 78.4 | 71.7 | 62.6 | 67.1 |
| | 830 | 100.0 | 78.4 | 71.7 | 62.6 | 67.1 |

TABLE 7

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 88.7 | 85.0 | 81.5 | 77.2 |
| 1 | 83 | 100.0 | 74.3 | 81.1 | 86.9 | 83.5 |
| | 830 | 100.0 | 70.2 | 64.4 | 60.6 | 78.3 |
| 20 | 83 | 100.0 | 86.6 | 88.4 | 83.9 | 87.5 |
| | 830 | 100.0 | 80.6 | 87.8 | 82.9 | 84.5 |
| 24 | 83 | 100.0 | 71.1 | 70.7 | 85.6 | 80.1 |
| | 830 | 100.0 | 69.1 | 61.9 | 54.4 | 53.0 |
| 28 | 83 | 100.0 | 83.7 | 87.7 | 82.6 | 80.8 |
| | 830 | 100.0 | 73.5 | 87.2 | 83.8 | 81.6 |
| 23 | 83 | 100.0 | 73.6 | 72.2 | 83.3 | 82.4 |
| | 830 | 100.0 | 68.5 | 61.6 | 56.9 | 71.1 |
| 27 | 83 | 100.0 | 93.5 | 94.3 | 86.4 | 82.7 |
| | 830 | 100.0 | 79.5 | 94.1 | 87.0 | 82.9 |

TABLE 8

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 100.0 | 88.2 | 85.9 | 78.9 |
| 22 | 83 | 100.0 | 76.1 | 70.7 | 70.7 | 75.9 |
| | 830 | 100.0 | 77.2 | 70.7 | 55.8 | 48.5 |
| 29 | 83 | 100.0 | 84.6 | 91.7 | 83.2 | 76.6 |
| | 830 | 100.0 | 75.0 | 84.7 | 78.0 | 73.1 |
| 30 | 83 | 100.0 | 77.2 | 80.7 | 83.2 | 77.7 |
| | 830 | 100.0 | 74.0 | 63.8 | 65.4 | 73.9 |
| 31 | 83 | 100.0 | 79.1 | 72.7 | 77.5 | 74.3 |
| | 830 | 100.0 | 74.3 | 65.6 | 57.3 | 49.6 |
| 25 | 83 | 100.0 | 76.9 | 67.6 | 66.7 | 71.3 |
| | 830 | 100.0 | 73.4 | 64.3 | 51.8 | 44.3 |
| 26 | 83 | 100.0 | 78.9 | 67.6 | 70.4 | 75.2 |
| | 830 | 100.0 | 73.9 | 62.9 | 52.1 | 48.2 |

TABLE 9

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 96.5 | 94.1 | 87.3 | 83.8 |
| 32 | 83 | 100.0 | 82.4 | 76.1 | 79.1 | 84.1 |
| | 830 | 100.0 | 84.5 | 73.6 | 65.9 | 64.2 |

TABLE 10

| Peptide No. | Concentration (ng/ml) | Ratio (%) of Reduction of Level in Serum | | | | |
|---|---|---|---|---|---|---|
| | | 0 hour | 1 hour | 2 hours | 4 hours | 6 hours |
| none | — | 100.0 | 98.4 | 96.5 | 92.4 | 86.0 |
| 33 | 83 | 100.0 | 78.2 | 70.0 | 92.4 | 86.0 |
| | 830 | 100.0 | 80.8 | 71.8 | 63.5 | 55.1 |

From the foregoing results, it was confirmed that the peptide of the present invention has an action of reducing the calcium level in serum.

The acute toxicity ($LD_{50}$) of the peptide of the present invention is 10,000 I.U./kg or more in mice upon either oral administration or intravenous injection, or 5,000 I.U./kg or more in rats upon either oral administration or intravenous injection. Namely, the peptide of the present invention has a high safety factor.

Accordingly, the peptide of the present invention is a safe medicine having no substantial adverse effect and is effective for remedying hypercalcemia, Paget's disease of the bone, and osteoporosis.

The amount administered of the peptide of the present invention and the method of preparing a medicine of the present invention will now be described.

The peptide of the present invention can be administered to animals and human directly or together with a customary pharmaceutical carrier. The administration form is appropriately selected, i.e., there can be mentioned non-oral medicines such as an injection, a suppository and a medicine to be administered to a mucous membrane.

For the non-oral medicine to exert an intended effect, preferably the peptide of the present invention is administered at a titer of 10 to 200 I.U. per day for an adult by intravenous injection, intravenous instillation, hypodermic injection or intramuscular injection or in the form of a suppository or a medicine to be administered to a mucous membrane, although the amount administered of the peptide depends upon the age and body weight of a patient and the severity of the disease.

These non-oral medicines are prepared by customary procedures. In general, as the diluent, there can be used distilled water for injection, physiological saline solution, an aqueous solution of glucose, a vegetable oil for injection, sesame oil, peanut oil, soybean oil, corn oil, propylene glycol and polyethylene glycol. A fungicide, an antiseptic agent and a stabilizer can be added. From the viewpoint of safety, there can be adopted a method in which the non-oral medicine is filled in a vial or the like and is then frozen, water is removed by a conventional freeze-drying technique, and the dry product is formed into a liquid again just before administration. Furthermore, an isotonic agent, a preservative, an antiseptic agent, an analgesic agent, a dispersant, an antioxidant and the like can be added according to need.

As another non-oral medicine, there can be mentioned a suppository for administration into the rectum, a medicine for administration to a mucous membrane, an ointment and the like, which can be prepared by customary procedures.

The present invention will now be described in detail with reference to the following examples that by no means limit the scope of the invention.

EXAMPLE 1

(1) Activation of Resin

A reaction vessel (supplied by Peninsula Laboratory) for the solid phase synthesis of peptides was charged with 150 g of a BEA resin (supplied by Peninsula Laboratory, divinylbenzene content=1%, 100–120 mesh, amino group content=0.86 mM/g), and the resin was stirred with the following solvents in sequence two times for each solvent for 5 minutes at each stirring, followed by filtration.

(i) 1 l of methylene chloride (ii) 420 ml of 10% TEA/methylene chloride

Then, washing was carried out with 1.5 l each of methylene chloride, methanol and methylene chloride in sequence. Washing was conducted two times with each solvent and stirring was conducted for 2 minutes at each washing, and filtration was carried out after each stirring. (This washing operation will be referred to as "washing operation I" hereinafter.)

(2) Step 1

All of the resin obtained at the above procedure (1) was stirred with the following solvents in sequence and filtered.

Coupling:

1.5 l of methylene chloride +25.8 g (0.12 mole) of Boc-Pro +120 ml of 1 M DCC/methylene chloride (2.5 hours)

Then the washing operation I was carried out.

Acetylation:

1.5 l of methylene chloride +10 ml of acetic anhydride +100 ml of 10% TEA/methylene chloride (30 minutes)

Then the washing operation I was carried out.

When the treated resin was subjected to the ninhydrin test, the result was negative.

(3) Step 2

All of the resin obtained by the above procedure (2) was stirred with the following solvents in sequence and filtered.

Removal of Protecting Group:

50% TFA/methylene chloride (5 minutes and 25 minutes, 1.8 l each)

Then, washing was carried out by stirring the resin with 1.5 l each of methylene chloride, methanol and chloroform two times for each solvent for 2 minutes at each stirring, followed by filtration. (This washing operation will be referred to as "washing operation II" hereinafter).

Neutralization:

1.5 l of chloroform +400 ml of 10% TEA/methylene chloride (5 minutes and 15 minutes)

Then the washing operation I was carried out.

Coupling:

1.5 l of methylene chloride +56.7 g (0.30 mole) of Boc-Ala +300 ml of 1 M DCC/methylene chloride (2 hours)

Then the washing operation I was carried out.

When the treated resin was subjected to the ninhydrin test, the result was negative.

(4) Steps 3–11

All of the resin obtained by the above procedure (3) was subjected to removal of the protecting group, neutralization and washing in the same manner as the above procedure (3) except that protected amino groups shown in Table 11 were coupled in sequence.

In Table 11, $CH_2Cl_2$ represents methylene chloride, DMF represents dimethylformamide, and HOBt represents 1-hydroxybenzotriazole.

TABLE 11

| | | Amount used | | Coupling Conditions | |
|---|---|---|---|---|---|
| Step | Protected Amino Acid | (g) | Solvent | Time (hours) | Coupling agent |
| 3 | Boc-Gly | 52.5 | $CH_2Cl_2$ | 14.0 | DCC |
| 4 | Boc-Val | 65.1 | $CH_2Cl_2$ | 2.0 | DCC |
| 5 | Boc-Gly | 52.5 | $CH_2Cl_2$ | 14.5 | DCC |
| 6 | Boc-Ile · ½$H_2O$ | 72.0 | $CH_2Cl_2$ | 2.0 | DCC |
| 7 | Boc-Ala | 56.7 | $CH_2Cl_2$ | 15.0 | DCC |
| 8 | Boc-Thr(Bzl) | 92.7 | $CH_2Cl_2$ | 2.0 | DCC |
| | | 57.3 | $CH_2Cl_2$ | 16.0 | DCC + HOBt |
| | | 25.0 | DMF | 3.0 | DCC + HOBt |
| 9 | Boc-Gln-ONp | 135.0 | DMF | 14.5 | — |
| | | 50.0 | DMF | 5.0 | — |
| 10 | Boc-Pro | 64.5 | DMF | 13.5 | DCC + HOBt |
| | | 25.0 | $CH_2Cl_2$ | 3.0 | DCC |
| 11 | Boc-Tyr(Br-Z) | 237.2 | $CH_2Cl_2$ | 17.0 | DCC |
| | | 100.0 | DMF | 44.0 | DCC + HOBt |

After coupling of tyrosine at step 11 and washing, the peptide-resin was taken out from the reaction vessel and dried.

(5) Steps 12–13

By using 100 g of the peptide-resin obtained by the above procedure (4), removal of the protecting group, neutralization and washing were carried out in the same manner as the above procedure (3) except that protected amino acids shown in Table 12 were coupled in sequence and the amount of the solvent was adjusted to ⅔ of the amount used in procedure (3).

TABLE 12

| | | Amount used | | Coupling Conditions | |
|---|---|---|---|---|---|
| Step | Protected Amino Acid | (g) | Solvent | Time (hours) | Coupling agent |
| 12 | Boc-Thr(Bzl) | 27.8 | DMF | 20.5 | DCC + HOBt |
| 13 | Boc-Gln-ONp | 46.3 | DMF | 20.5 | — |
| | | 25.0 | DMF | 24.0 | — |

After coupling glutamine at step 13 and washing, the peptide-resin was taken out from the reaction vessel and dried.

(6) Steps 14–17

By using 30 g of the peptide-resin obtained by procedure (5), removal of the protecting group, neutralization and washing were carried out in the same manner as in procedure (3) except that protected amino acids shown in Table 13 were coupled in sequence and the amount of the solvent was adjusted to ⅙ of the amount used in procedure (3).

TABLE 13

| | | Amount used | | Coupling Conditions | |
|---|---|---|---|---|---|
| Step | Protected Amino Acid | (g) | Solvent | Time (hours) | Coupling agent |
| 14 | Boc-Leu · $H_2O$ | 6.7 | DMF | 18.3 | DCC + HOBt |
| 15 | Boc-Lys(Cl-Z) | 8.5 | DMF | 20.3 | DCC + HOBt |
| 16 | Boc-His(Tos) | 11.1 | $CH_2Cl_2$ | 18.0 | DCC |
| | | 4.1 | $CH_2Cl_2$ | 4.0 | DCC |
| 17 | Boc-Leu · $H_2O$ | 6.7 | DMF | 14.5 | DCC + HOBt |

After coupling of leucine at step 17 and washing, the peptide-resin was taken out from the reaction vessel and dried.

(7) Steps 18–25

By using 18 g of the peptide-resin obtained by procedure (6), removal of the protecting group, neutralization and washing were carried out in the same manner as in procedure (3) except that protected amino acids shown in Table 14 were coupled in sequence and the amount of the solvent was adjusted to ⅙ of the amount used in procedure (3).

TABLE 14

| Step | Protected Amino Acid | Amount used (g) | Solvent | Coupling Conditions | |
|---|---|---|---|---|---|
| | | | | Time (hours) | Coupling agent |
| 18 | Boc-Glu(OBzl) | 4.6 | DMF | 14.5 | DCC + HOBt |
| 19 | Boc-Gln | 3.3 | DMF | 19.7 | DCC + HOBt |
| 20 | Boc-Ser(Bzl) | 4.0 | DMF | 16.8 | DCC + HOBt |
| 21 | Boc-Leu · H$_2$O | 3.4 | DMF | 17.0 | DCC + HOBt |
| 22 | Boc-Lys(Cl-Z) | 4.3 | DMF | 21.2 | DCC + HOBt |
| 23 | Boc-Gly | 2.4 | DMF | 19.5 | DCC + HOBt |
| 24 | Boc-Leu · H$_2$O | 3.4 | DMF | 20.0 | DCC + HOBt |
| 25 | Boc-Met | 3.4 | DMF | 19.8 | DCC + HOBt |

After coupling methionine at step 25 and washing, the peptide-resin was taken out from the reaction vessel and dried.

(8) Steps 26–32

By using 11 g of the peptide-resin obtained by procedure (7), removal of the protecting group, neutralization and washing were carried out in the same manner as in procedure (3) except that protected amino acids shown in Table 15 were coupled in sequence and the amount of the solvent was adjusted to ⅙ of the amount used in procedure (3).

TABLE 15

| Step | Protected Amino Acid | Amount used (g) | Solvent | Coupling Conditions | |
|---|---|---|---|---|---|
| | | | | Time (hours) | Coupling agent |
| 26 | Boc-Cys (4-Me-Bzl) | 2.2 0.7 | DMF DMF | 20.0 2.5 | DCC + HOBt DCC + HOBt |
| 27 | Boc-Thr(Bzl) | 2.1 1.4 2.2 | DMF DMF CH$_2$Cl$_2$ | 14.0 21.0 3.0 | DCC + HOBt DCC + HOBt DCC |
| 28 | Boc-Ser(Bzl) | 2.0 | DMF | 15.7 | DCC + HOBt |
| 29 | Boc-Leu · H$_2$O | 1.7 | DMF | 20.2 | DCC + HOBt |
| 30 | Boc-Asn Boc-Asn(Xan) | 3.1 1.7 | DMF DMF | 20.2 4.0 | DCC + HOBt DCC |
| 31 | Boc-Gly | 5.1 | DMF | 21.2 | DCC + HOBt |
| 32 | Boc-Cys (4-Me-Bzl) | 2.7 | DMF | 3.7 | DCC + HOBt |

After coupling cysteine at step 32 and washing, the peptide-resin was taken out from the reaction vessel and dried.

(9) Isolation of Peptide from Resin and Removal of Protecting Groups

An HF reaction vessel was charged with 4 g of the peptide-resin obtained by procedure (8), and 4 ml of anisole and 1 ml of methyl sulfide were added and the mixture was stirred. The reaction vessel was set to an HF reaction apparatus (supplied by Peptide Laboratory) and cooled in a dry ice/acetone bath, and about 35 ml of HF was introduced. Then, in an ice water bath, the reaction mixture was stirred for 45 minutes to effect reaction, and HF was removed by distillation for 15 minutes by using a vacuum pump. Then, in a water bath, evacuation was further conducted for 15 minutes.

Then, ether was added and the mixture was thoroughly stirred and filtered by using a glass filter. The residue on the filter was washed with ether again (about 300 ml of ether was used as a whole). The peptide was extracted by a 0.1N aqueous solution of acetic acid (4×100 ml).

(10) Cyclization

To the aqueous solution of acetic acid obtained by procedure (9) were added 150 mg of reduction type glutathione and 300 mg of oxidation type glutathione, and an aqueous acetic acid solution was added to the mixture so that the total volume was about 800 ml, and the pH value was adjusted to 9.0 by aqueous ammonia. The mixture was stirred for 30 minutes and the pH value was adjusted to 8.0 by acetic anhydride. The mixture was stirred overnight while bubbling with nitrogen gas.

(11) Purification

The pH value of the solution obtained by procedure (10) was adjusted to 5.0 by acetic anhydride and the solution was subjected to a concentration treatment using an ultrafiltration apparatus provided with an ultrafiltration membrane having a molecular weight of 1000 and was then subjected to a dialysis treatment using an ammonium acetate buffer solution. The obtained liquid was eluted in a column packed with a cation-exchange resin (CM52 supplied by Wattman) by using an ammonium acetate buffer solution as the moving phase. The eluate was freeze-dried.

The dry product was purified by the separating reversed phase high-speed liquid chromatography. The column used was ODP-90 (supplied by Asahi Kasei), and the gradient elution was carried out by using a phosphate buffer/acetonitrile system. The fraction of the main peak was concentrated by the above-mentioned ultrafiltration apparatus. The concentrate was eluted in a column packed with a cation-exchange resin (SP-Sephadex supplied by Pharmacia) by using an aqueous solution of sodium chloride as the moving phase, and the eluate was further eluted in a column packed with Sephadex G-25 (supplied by Pharmacia) by using an aqueous solution of acetic acid as the moving phase. The eluate was freeze-dried.

The results of the amino acid analysis of the obtained purified product are shown below. Each parenthesized value is a theoretical value.

Asp; 1.00 (1), Thr; 2.80 (3), Ser; 1.82 (2),

Glu; 4.05 (4), Pro; 1.98 (2), Gly; 3.94 (4),

Ala; 2.00 (2), Cys; 1.65 (2), Val; 1.01 (1),

Met; 1.01 (1), Ile; 1.02 (1), Leu; 4.99 (5),

Tyr; 0.97 (1), Lys; 2.00 (2), His; 1.04 (1)

The above results of the amino acid analysis support the conclusion that the purified product obtained by the above-mentioned process is peptide No. 1 having the amino acid composition shown in Table 1.

EXAMPLE 2

A purified product was obtained by subjecting 30 g of the peptide-resin obtained in procedure (5) of Example 1 to the operations of procedure (6) and subsequent steps in the same manner as described in Example 1 except that the coupling of leucine at step 14 and the second coupling of cysteine at step 26 were not carried out.

The results of the amino acid analysis of the purified product are shown below. Each parenthesized value is a theoretical value.

Asp; 1.00 (1), Thr; 2.64 (3), Ser; 1.59 (2),

Glu; 4.00 (4), Pro; 2.12 (2), Gly; 3.90 (4),

Ala; 2.01 (2), Cys; 1.62 (2), Val; 0.99 (1),

Met; 1.00 (1), Ile; 1.05 (1), Leu; 4.12 (4),

Tyr; 1.10 (1), Lys; 1.97 (2), His; 1.03 (1)

The results of the amino acid analysis support the conclusion that the purified product obtained by the above-mentioned process is peptide No. 2 having the amino acid composition shown in Table 1.

EXAMPLE 3

A purified product was obtained by subjecting 30 g of the peptide-resin obtained in procedure (4) of Example 1 to the operations of procedure (6) and subsequent steps in the same manner as described in Example 1 except that the coupling in procedure (5) was not carried out and the coupling conditions for the amino acid shown in Table 16 were changed as shown in Table 16.

TABLE 16

| Step | Protected Amino Acid | Amount used (g) | Solvent | Coupling Conditions Time (hours) | Coupling agent |
|---|---|---|---|---|---|
| 15 | Boc-Lys(Cl-Z) | 3.8 | DMF | 4.0 | DCC + HOBt |
| 16 | Boc-His(Tos) | 11.1 | $CH_2Cl_2$ | 15.5 | DCC |
| 22 | Boc-Lys(Cl-Z) | 4.3 | DMF | 21.2 | DCC + HOBt |
| 27 | Boc-Thr(Bzl) | 2.1 | DMF | 14.0 | DCC + HOBt |
| 30 | Boc-Asn | 3.1 | DMF | 20.2 | DCC + HOBt |
| 32 | Boc-Cys (4-Me-Bzl) | 2.7 | DMF | 20.8 | DCC + HOBt |

The results of the amino acid analysis of the purified product are shown below. Each parenthesized value is a theoretical value.

Asp; 1.01 (1), Thr; 1.89 (2), Ser; 1.80 (2),

Glu; 3.08 (3), Pro; 2.17 (2), Gly; 3.93 (4),

Ala; 2.02 (2), Cys; 1.65 (2), Val; 1.01 (1),

Met; 0.96 (1), Ile; 0.98 (1), Leu; 4.95 (5),

Tyr; 0.93 (1), Lys; 1.96(2), His; 1.00 (1)

The above results of the amino acid analysis support the conclusion that the purified product obtained by the above-mentioned process is peptide No. 3 having the amino acid composition shown in Table 1.

EXAMPLE 4

A purified product was obtained by subjecting 30 g of the peptide-resin obtained at procedure (5) of Example 1 to the operations of procedure (6) and subsequent steps in the same manner as described in Example 1 except that instead of coupling leucine at step 14 at procedure (6) of Example 1, the coupling of glycine at the same position was carried out and the second coupling of cysteine at step 26 at procedure (8) was not carried out. Further, the coupling of threonine at step 27 was carried out two times and acetylation was carried out.

The results of the amino acid analysis of the obtained purified product are shown below. Each parenthesized value is a theoretical value.

Asp; 1.07 (1), Thr; 2.69 (3), Ser; 1.72 (2),

Glu; 3.97 (4), Pro; 2.03 (2), Gly; 4.96 (5),

Ala; 2.01 (2), Cys; 1.64 (2), Val; 1.10 (1),

Met; 0.91 (1), Ile; 0.91 (1), Leu; 3.92 (4),

Tyr; 1.06 (1), Lys; 1.96 (2), His; 0.96 (1)

The above results of the amino acid analysis support the conclusion that the purified product obtained by the above-mentioned process is peptide No. 4 having the amino acid composition shown in Table 1.

EXAMPLE 5

(1) Activation of Resin

A reaction vessel (supplied by Peninsula Laboratory) for the solid phase synthesis of peptides was charged with 75 g of a BHA resin (supplied by Peninsula Laboratory, divinylbenzene content=1%, 100–120 mesh, amino group content= 0.86 mM/g), and the resin was stirred with 900 ml of methylene chloride two times for 2 minutes at each stirring, followed by filtration. Then, the resin was stirred with the following solvents in sequence two times for each solvent for 5 minutes at each stirring, followed by filtration.

(i) 900 ml of methylene chloride (ii) 300 ml of 10% TEA/methylene chloride

Then, washing was carried out with 900 ml each of methylene chloride, ethanol and methylene chloride in sequence. Washing was conducted two times with each solvent and stirring was conducted for 2 minutes at each washing, and filtration was carried out after each stirring. (This washing operation will be referred to as "washing operation III" hereinafter.)

(2) Step 1

All of the resin obtained at procedure (1) was stirred with the following solvents in sequence and filtered.

Coupling:

900 ml of methylene chloride +25 g (0.12 mole) of Boc-Pro +117 ml of 1 M DCC/methylene chloride (16 hours)

Then the washing operation III was carried out.

Acetylation:

900 ml of methylene chloride +10 ml of acetic anhydride +100 ml of 10% TEA/methylene chloride (1 hour)

Then the washing operation III was carried out.

When the treated resin was subjected to the ninhydrin test, the result was negative.

(3) Step 2

All of the resin obtained at procedure (2) was stirred with the following solvents in sequence and filtered.

Removal of Protecting Group:

50% TFA/methylene chloride (5 minutes and 25 minutes, 1 l each)

Then, washing was carried out by stirring the resin with 900 ml each of methylene chloride, methanol and chloroform two times for each solvent for 2 minutes at each stirring, followed by filtration. (This washing operation will be referred to as "washing operation II" hereinafter).

Neutralization:

800 ml of chloroform +200 ml of 10%

TEA/methylene chloride (5 minutes and 15 minutes)

Then the washing operation I was carried out.

Coupling:

1 l of methylene chloride +45 g (0.15 mole) of Boc-Thr (Bzl) +146 ml of 1 M DCC/methylene chloride (16 hours)

Then the washing operation III was carried out.

When the treated resin was subjected to the ninhydrin test, the result was negative.

(4) Steps 3–11

All of the resin obtained at procedure (3) was subjected to removal of the protecting group, neutralization and washing in the same manner as at procedure (3) except that protected amino groups shown in Table 17 were coupled in sequence.

In Table 17, $CH_2Cl_2$ represents methylene chloride, DMF represents dimethylformamide, and HOBt represents 1-hydroxybenzotriazole.

TABLE 17

| Step | Protected Amino Acid | Amount used (g) | Solvent | Time (hours) | Coupling agent |
|---|---|---|---|---|---|
| 3 | Boc-Gly | 27.2 | $CH_2Cl_2$ | 4.0 | DCC |
| 4 | Boc-Ser(Bzl) | 45.7 | $CH_2Cl_2$ | 16.0 | DCC |
| 5 | Boc-Gly | 27.2 | $CH_2Cl_2$ | 16.0 | DCC |
| 6 | Boc-Ile · ½$H_2O$ | 37.2 | $CH_2Cl_2$ | 16.0 | DCC |
| 7 | Boc-Ala | 29.3 | $CH_2Cl_2$ | 16.0 | DCC |
| 8 | Boc-Thr(Bzl) | 47.9 | DMF | 16.0 | DCC + HOBt |
| 9 | Boc-Gln | 38.2 | DMF | 16.0 | DCC + HOBt |
| 10 | Boc-Pro | 33.3 | DMF | 16.0 | DCC + HOBt |
| 11 | Boc-Tyr(Br-Z) | 148.5 | $CH_2Cl_2$ | 16.0 | DCC |
|  |  | 54.5 | DMF | 16.0 | DCC + HOBt |
|  |  | 54.5 | DMF | 16.0 | DCC + HOBt |

After coupling of tyrosine at step 11 and washing, peptide-resin was taken out from the reaction vessel and dried.

(5) Steps 12–13

By using 35 g of the peptide-resin obtained at procedure (4), removal of the protecting group, neutralization and washing were carried out in the same manner as at procedure (3) except that protected amino acids shown in Table 18 were coupled in sequence and the amount of the solvent was adjusted to ¼ of the amount used at procedure (3).

TABLE 18

| Step | Protected Amino Acid | Amount used (g) | Solvent | Time (hours) | Coupling agent |
|---|---|---|---|---|---|
| 12 | Boc-Thr(Bzl) | 11.1 | DMF | 16.0 | DCC + HOBt |
| 13 | Boc-Gln | 8.9 | DMF | 16.0 | DCC + HOBt |

After coupling glutamine at step 13 and washing, the peptide-resin was taken out from the reaction vessel and dried.

(6) Steps 14–32

By using 11 g of the peptide-resin obtained at procedure (5), removal of the protecting group, neutralization and washing were carried out in the same manner as at procedure (3) except that protected amino acids shown in Table 19 were coupled in sequence and the amount of the solvent was adjusted to ¼ of the amount used at procedure (3).

TABLE 19

| Step | Protected Amino Acid | Amount used (g) | Solvent | Time (hours) | Coupling agent |
|---|---|---|---|---|---|
| 14 | Boc-Leu · $H_2O$ | 2.8 | DMF | 16.0 | DCC + HOBt |
| 15 | Boc-Lys(Cl-Z) | 3.6 | DMF | 16.0 | DCC + HOBt |
| 16 | Boc-His(Tos) | 4.6 | $CH_2Cl_2$ | 16.0 | DCC |
| 17 | Boc-Leu · $H_2O$ | 2.8 | DMF | 16.0 | DCC + HOBt |
| 18 | Boc-Glu(OBzl) | 3.8 | DMF | 16.0 | DCC + HOBt |
| 19 | Boc-Gln | 2.8 | DMF | 16.0 | DCC + HOBt |
| 20 | Boc-Ser(Bzl) | 3.3 | DMF | 16.0 | DCC + HOBt |
| 21 | Boc-Leu · $H_2O$ | 2.8 | DMF | 16.0 | DCC + HOBt |
| 22 | Boc-Lys(Cl-Z) | 3.6 | DMF | 16.0 | DCC + HOBt |
| 23 | Boc-Gly | 2.0 | DMF | 16.0 | DCC + HOBt |
| 24 | Boc-Leu · $H_2O$ | 2.8 | DMF | 16.0 | DCC + HOBt |
| 25 | Boc-Met | 2.8 | DMF | 16.0 | DCC + HOBt |
| 26 | Boc-Cys (4-Me-Bzl) | 3.7 | DMF | 16.0 | DCC + HOBt |

TABLE 19-continued

| Step | Protected Amino Acid | Amount used (g) | Solvent | Time (hours) | Coupling agent |
|---|---|---|---|---|---|
| 27 | Boc-Thr(Bzl) | 3.5 | DMF | 16.0 | DCC + HOBt |
| 28 | Boc-Ser(Bzl) | 3.3 | DMF | 16.0 | DCC + HOBt |
| 29 | Boc-Leu · $H_2O$ | 2.8 | DMF | 16.0 | DCC + HOBt |
| 30 | Boc-Asn | 4.2 | DMF | 16.0 | DCC + HOBt |
|  | Boc-Asn(Xan) | 2.1 | DMF | 16.0 | DCC |
| 31 | Boc-Gly | 2.0 | DMF | 8.0 | DCC + HOBt |
| 32 | Boc-Cys (4-Me-Bzl) | 3.7 | DMF | 16.0 | DCC + HOBt |

After coupling cysteine at step 32 and washing, the peptide-resin was taken out from the reaction vessel and dried. Then, the peptide-resin was subjected to the operations of procedure (9) and subsequent steps in the same manner as described in Example 1.

The results of the amino acid analysis of the obtained purified product are shown below. Each parenthesized value is a theoretical value.

Asp; 1.02 (1), Thr; 3.56 (4), Ser; 2.53 (3),
Glu; 4.08 (4), Pro; 1.90 (2), Gly; 3.91 (4),
Ala; 0.98 (1), Cys; 1.64 (2), Met; 1.05 (1),
Ile; 1.13 (1), Leu; 5.16 (5), Tyr; 1.22 (1),
Lys; 2.01 (2), His; 0.97 (1)

The above results of the amino acid analysis support the conclusion that the purified product obtained by the above-mentioned process is peptide No. 5 having the amino acid composition shown in Table 1.

EXAMPLE 6

A purified product was obtained by subjecting 11 g of the peptide-resin obtained at procedure (5) of Example 5 to the operations of procedure (6) and subsequent steps in the same manner as described in Example 5 except that the coupling of leucine at step 14 was not carried out and the coupling conditions for the amino acid shown in Table 20 were changed as shown in Table 20.

TABLE 20

| Step | Protected Amino Acid | Amount used (g) | Solvent | Time (hours) | Coupling agent |
|---|---|---|---|---|---|
| 29 | Boc-Leu · $H_2O$ | 2.8 | DMF | 16.0 | DCC + HOBt |
|  |  | 2.5 | $CH_2Cl_2$ | 4.0 | DCC |

The results of the amino acid analysis of the purified product are shown below. Each parenthesized value is a theoretical value.

Asp; 1.00 (1), Thr; 3.64 (4), Ser; 2.74 (3),
Glu; 4.14 (4), Pro; 2.01 (2), Gly; 3.85 (4),
Ala; 1.00 (1), Cys; 1.50 (2), Met; 0.90 (1),
Ile; 1.10 (1), Leu; 4.16 (4), Tyr; 1.15 (1),
Lys; 2.00 (2), His; 1.03 (1)

The results of the amino acid analysis support the conclusion that the purified product obtained by the above-mentioned process is peptide No. 6 having the amino acid composition shown in Table 1.

EXAMPLE 7

A purified product was obtained by subjecting 11 g of the peptide-resin obtained at procedure (4) of Example 5 to the operations of procedure (6) and subsequent steps in the same manner as described in Example 5 except that coupling at procedure (5) of Example 5 was not carried out.

The results of the amino acid analysis of the obtained purified product are shown below. Each parenthesized value is a theoretical value.

Asp; 0.99 (1), Thr; 2.75 (3), Ser; 2.64 (3),

Glu; 3.11 (3), Pro; 2.02 (2), Gly; 3.90 (4),

Ala; 0.99 (1), Cys; 1.61 (2), Met; 0.99 (1),

Ile; 1.10 (1), Leu; 5.17 (5), Tyr; 1.14 (1),

Lys; 2.02 (2), His; 0.99 (1)

The above results of the amino acid analysis support the conclusion that the purified product obtained by the above-mentioned process is peptide No. 7 having the amino acid composition shown in Table 1.

EXAMPLE 8

A purified product was obtained by subjecting 11 g of the peptide-resin obtained at procedure (5) of Example 5 to the operations of procedure (6) and subsequent steps in the same manner as described in Example 5 except that instead of coupling leucine at step 14 at procedure (6) of Example 5, the coupling of glycine at the same position was carried out under the conditions shown in Table 21.

TABLE 21

| Step | Protected Amino Acid | Amount used (g) | Solvent | Time (hours) | Coupling agent |
|---|---|---|---|---|---|
| 14 | Boc-Gly | 2.0 | DMF | 16.0 | DCC + HOBt |

The results of the amino acid analysis of the obtained purified product are shown below. Each parenthesized value is a theoretical value.

Asp; 1.00 (1), Thr; 3.57 (4), Ser; 2.64 (3),

Glu; 4.10 (4), Pro; 2.08 (2), Gly; 4.89 (5),

Ala; 1.00 (1), Cys; 1.52 (2), Met; 0.99 (1),

Ile; 1.10 (1), Leu; 4.14 (4), Tyr; 0.98 (1),

Lys; 2.01 (2), His; 0.98 (1)

The above results of the amino acid analysis support the conclusion that the purified product obtained by the above-mentioned process is peptide No. 8 having the amino acid composition shown in Table 1.

EXAMPLE 9

(1) By using 75 g of the resin-peptide obtained at procedure (4) of Example 1 removal of the protecting group, neutralization and washing were carried out in the same manner as at procedure (3) of Example 1 except that protected amino acids shown in Table 22 were coupled in sequence, the amount of the solvent was adjusted to ⅔ of the amount used at procedure (3) of Example 1, and ethanol was used instead of methanol at the washing operations I and II.

TABLE 22

| Step | Protected Amino Acid | Amount used (g) | Solvent | Time (hours) | Coupling agent |
|---|---|---|---|---|---|
| 12 | Boc-Thr(Bzl) | 21.0 | DMF | 16.0 | DCC + HOBt |
| 13 | Boc-Gln | 17.0 | DMF | 16.0 | DCC + HOBt |
| 14 | Boc-Leu · H$_2$O | 17.0 | DMF | 16.0 | DCC + HOBt |
| 15 | Boc-Lys(Cl-Z) | 21.5 | DMF | 16.0 | DCC + HOBt |
| 16 | Boc-His(Tos) | 28.0 | CH$_2$Cl$_2$ | 16.0 | DCC |
| 17 | Boc-Leu · H$_2$O | 17.0 | DMF | 16.0 | DCC + HOBt |
| 18 | Boc-Glu(Bzl) | 23.0 | DMF | 16.0 | DCC + HOBt |
| 19 | Boc-Gln | 17.0 | DMF | 16.0 | DCC + HOBt |
| 20 | Boc-Ser(Bzl) | 20.0 | DMF | 16.0 | DCC + HOBt |
| 21 | Boc-Leu · H$_2$O | 17.0 | DMF | 16.0 | DCC + HOBt |
| 22 | Boc-Lys(Cl-Z) | 21.5 | DMF | 16.0 | DCC + HOBt |
| 23 | Boc-Gly | 12.0 | DMF | 16.0 | DCC + HOBt |
| 24 | Boc-Leu · H$_2$O | 17.0 | DMF | 16.0 | DCC + HOBt |

After coupling leucine at step 24 and washing, the peptide-resin was taken out from the reaction vessel and dried.

(2) By using 15 g of the peptide-resin obtained at procedure (1), protected amino acids shown in Table 23 were coupled in sequence.

TABLE 23

| Step | Protected Amino Acid | Amount used (g) | Solvent | Time (hours) | Coupling agent |
|---|---|---|---|---|---|
| 25 | Boc-Gly | 1.8 | DMF | 16.0 | DCC + HOBt |
| 26 | Boc-Cys (4-Me-Bzl) | 3.3 | DMF | 16.0 | DCC + HOBt |
| 27 | Boc-Thr(Bzl) | 3.1 | DMF | 16.0 | DCC + HOBt |
| 28 | Boc-Ser(Bzl) | 3.0 | DMF | 16.0 | DCC + HOBt |
| 29 | Boc-Leu · H$_2$O | 2.5 | DMF | 16.0 | DCC + HOBt |
| 30 | Boc-Asn | 3.5 | DMF | 16.0 | DCC + HOBt |
| 31 | Boc-Gly | 1.8 | DMF | 16.0 | DCC + HOBt |
| 32 | Boc-Cys (4-Me-Bzl) | 3.3 | DMF | 16.0 | DCC + HOBt |

After coupling cysteine at step 32 and washing, the peptide-resin was taken out from the reaction vessel and dried. Then, the peptide-resin was subjected to the operations of procedure (9) and subsequent steps in the same manner as described in Example 1.

The results of the amino acid analysis of the obtained purified product are shown below. Each parenthesized value is a theoretical value.

Asp; 1.02 (1), Thr; 2.62 (3), Ser; 1.70 (2),

Glu; 4.03 (4), Pro; 2.09 (2), Gly; 4.90 (5),

Ala; 2.02 (2), Cys; 1.74 (2), Val; 1.08 (1),

Ile; 1.01 (1), Leu; 5.20 (5), Tyr; 1.08 (1),

Lys; 2.03 (2), His; 0.99 (1)

The above results of the amino acid analysis support the conclusion that the purified product obtained by the above-mentioned process is peptide No. 9 having the amino acid concentration shown in Table 1.

EXAMPLE 10

A purified product was obtained by subjecting 15 g of the peptide-resin obtained at procedure (1) of Example 9 to the operations of procedure (2) and subsequent steps in the same manner as described in Example 9 except that the coupling of alanine at the same position was carried out instead of the coupling of glycine at step 25 at procedure (2) of Example 9 and the coupling of asparagine at step 30 was carried out two times, as shown in Table 24.

TABLE 24

| Step | Protected Amino Acid | Amount used (g) | Coupling Conditions | | |
|---|---|---|---|---|---|
| | | | Solvent | Time (hours) | Coupling agent |
| 29 | Boc-Ala | 1.9 | DMF | 16.0 | DCC + HOBt |
| 30 | Boc-Asn | 3.5 | DMF | 16.0 | DCC + HOBt |
| | Boc-Asn(Xan) | 4.1 | DMF | 16.0 | DCC |

The results of the amino acid analysis of the obtained purified product are shown below. Each parenthesized value is a theoretical value.

Asp; 1.01 (1), Thr; 2.59 (3), Ser; 1.72 (2),
Glu; 3.96 (4), Pro; 2.05 (2), Gly; 3.99 (4),
Ala; 3.03 (3), Cys; 1.62 (2), Val; 1.06 (1),
Ile; 1.02 (1), Leu; 4.94 (5), Tyr; 0.95 (1),
Lys; 2.01 (2), His; 1.05 (1)

The above results of the amino acid analysis support the conclusion that the purified product obtained by the above-mentioned process is peptide No. 10 having the amino acid composition shown in Table 1.

EXAMPLE 11

By using 15 g of the peptide-resin obtained at procedure (1) of Example 9, a purified product was obtained by carrying out the operations of procedure (2) and subsequent steps in the same manner as described in Example 9 except that the coupling of valine at the same position was carried out instead of the coupling of glycine at step 25 at procedure (2) of Example 9, as shown in Table 25.

TABLE 25

| Step | Protected Amino Acid | Coupling Conditions | | | |
|---|---|---|---|---|---|
| | | Amount used (g) | Solvent | Time (hours) | Coupling agent |
| 25 | Boc-Val | 2.2 | DMF | 16.0 | DCC + HOBt |

The results of the amino acid analysis of the obtained purified product are shown below. Each parenthesized value is a theoretical value.

Asp; 0.99 (1), Thr; 2.66 (3), Ser; 1.79 (2),
Glu; 4.03 (4), Pro; 2.10 (2), Gly; 3.94 (4),
Ala; 2.04 (2), Cys; 1.75 (2), Val; 2.06 (2),
Ile; 0.94 (1), Leu; 5.10 (5), Tyr; 0.74 (1),
Lys; 2.01 (2), His; 1.05 (1)

The above results of the amino acid analysis support the conclusion that the purified product obtained by the above-mentioned process is peptide No. 11 having the amino acid composition shown in Table 1.

EXAMPLE 12

A purified product was obtained by subjecting 15 g of the peptide-resin obtained at procedure (1) of Example 9 to the operations of procedure (2) and subsequent steps in the same manner as described in Example 9 except that the coupling of proline at the same position was carried out instead of the coupling of glycine at step 25 at procedure (2) of Example 9, as shown in Table 26.

TABLE 26

| Step | Protected Amino Acid | Coupling Conditions | | | |
|---|---|---|---|---|---|
| | | Amount used (g) | Solvent | Time (hours) | Coupling agent |
| 25 | Boc-Pro | 2.2 | DMF | 16.0 | DCC + HOBt |

The results of the amino acid analysis of the obtained purified product are shown below. Each parenthesized value is a theoretical value.

Asp; 1.02 (1), Thr; 2.62 (3), Ser; 1.68 (2),
Glu; 4.00 (4), Pro; 3.19 (3), Gly; 3.93 (4),
Ala; 2.04 (2), Cys; 1.80 (2), Val; 1.10 (1),
Ile; 0.97 (1), Leu; 5.14 (5), Tyr; 0.94 (1),
Lys; 2.01 (2), His; 0.99 (1)

The above results of the amino acid analysis support the conclusion that the purified product obtained according to the above-mentioned process is peptide No. 12 having the amino acid composition shown in Table 1.

EXAMPLE 13

A purified product was obtained by subjecting 15 g of the peptide-resin obtained at procedure (1) of Example 9 to the operations of procedure (2) and subsequent steps in the same manner as described in Example 9 except that the coupling of leucine at the same position was carried out instead of the coupling of glycine at step 25 at procedure (2) of Example 9 and the coupling of asparagine at step 30 was carried out two times, as shown in Table 27.

TABLE 27

| Step | Protected Amino Acid | Coupling Conditions | | | |
|---|---|---|---|---|---|
| | | Amount used (g) | Solvent | Time (hours) | Coupling agent |
| 25 | Boc-Leu · H$_2$O | 2.5 | DMF | 16.0 | DCC + HOBt |
| 30 | Boc-Asn | 3.5 | DMF | 16.0 | DCC + HOBt |
| | Boc-Asn(Xan) | 4.1 | DMF | 16.0 | DCC |

The results of the amino acid analysis of the obtained purified product are shown below. Each parenthesized value is a theoretical value.

Asp; 1.02 (1), Thr; 2.62 (3), Ser; 1.72 (2),
Glu; 3.99 (4), Pro; 2.09 (2), Gly; 3.90 (4),
Ala; 2.09 (2), Cys; 1.73 (2), Val; 1.09 (1),
Ile; 0.96 (1), Leu; 6.05 (6), Tyr; 0.89 (1),
Lys; 2.00 (2), His; 1.08 (1)

The above results of the amino acid analysis support the conclusion that the purified product obtained according to the above-mentioned process is peptide No. 13 having the amino acid composition shown in Table 1.

EXAMPLE 14

Protected amino acids shown in Table 28 were coupled in sequence to 11 g of the peptide-resin obtained at procedure (7) of Example 1. Removal of the protecting groups, neutralizations washing, drying and isolation of the peptide were carried out in the same manner as at procedures (8) and (9) of Example 1. The pH value of the obtained solution was adjusted to 9 and the solution was stirred for 30 minutes. Then, the purification was carried out in the same manner as at procedure (11) of Example 1.

TABLE 28

| Step | Protected Amino Acid | Coupling Conditions | | | |
|------|----------------------|---------------------|---|---|---|
| | | Amount used (g) | Solvent | Time Time (hours) | Coupling agent |
| 26 | Boc-Ala | 2.6 | DMF | 22.0 | DCC + HOBt |
| 27 | Boc-Thr(Bzl) | 4.2 | DMF | 21.3 | DCC + HOBt |
| 28 | Boc-Ser(Bzl) | 4.0 | DMF | 19.4 | DCC + HOBt |
| 2g | Boc-Leu · H$_2$O | 3.4 | DMF | 21.8 | DCC + HOBt |
| 30 | Boc-Asn | 3.2 | DMF | 19.1 | DCC + HOBt |
| 31 | Boc-Gly | 2.4 | DMF | 20.0 | DCC + HOBt |
| 32 | Boc-Ala | 2.6 | DMF | 20.0 | DCC + HOBt |

The results of the amino acid analysis of the obtained purified product are shown below. Note, each parenthesized value is a theoretical value.

Asp; 1.03 (1), Thr; 2.74 (3), Ser; 1.64 (2),
Glu; 4.08 (4), Pro; 2.02 (2), Gly; 4.00 (4),
Ala; 3.84 (4), Val; 1.01 (1), Met; 1.17 (1),
Ile; 1.12 (1), Leu; 5.33 (5), Tyr; 1.33 (1),
Lys; 2.02 (2), His; 1.08 (1)

The above results of the amino acid analysis support the determination that the purified product obtained according to the above-mentioned process is peptide No. 14 having the amino acid composition shown in Table 1.

EXAMPLE 15

A purified product was obtained by using 11 g of the peptide-resin obtained in Example 2 by carrying out the same treatments as at procedures (6) and (7) of Example 1 and treating this peptide-resin in the same manner as described in Example 14, except that the coupling of asparagine at step 30 of Example 14 was carried out two times as shown in Table 29.

TABLE 29

| Step | Protected Amino Acid | Coupling Conditions | | | |
|------|----------------------|---------------------|---|---|---|
| | | Amount used (g) | Solvent | Time Time (hours) | Coupling agent |
| 30 | Boc-ASN (Xan) | 1.7 | DMF | 24.0 | DCC |

The results of the amino acid analysis of the purified product are shown below. Note, each parenthesized value is a theoretical value.

Asp; 1.00 (1), Thr; 2.78 (3), Ser; 1.69 (2),
Glu; 4.09 (4), Pro; 2.00 (2), Gly; 3.99 (4),
Ala; 3.89 (4), Val; 1.06 (1), Met; 1.08 (1),
Ile; 1.07 (1), Leu; 4.23 (4), Tyr; 1.17 (1),
Lys; 2.03 (2), His; 1.07 (1)

The above results of the amino acid analysis support the determination that the purified product obtained according to the above-mentioned process is peptide No. 15 having the amino acid composition shown in Table 1.

EXAMPLE 16

A purified product was obtained by using 11 g of the peptide-resin obtained in Example 3 by carrying out the same treatments as at procedures (6) and (7) of Example 1 and treating this peptide-resin in the same manner as described in Example 14, except that the coupling of leucine at step 29 of Example 14 and the coupling of asparagine at step 30 of Example 14 were changed as shown in Table 30.

TABLE 30

| Step | Protected Amino Acid | Coupling Conditions | | | |
|------|----------------------|---------------------|---|---|---|
| | | Amount used (g) | Solvent | Time Time (hours) | Coupling agent |
| 29 | Boc-Leu · H$_2$O | 3.4 | DMF | 21.8 | DCC + HOBt |
| 30 | Boc-Asn (Xan) | 1.7 | DMF | 24.0 | DCC |

The results of the amino acid analysis of the above purified product are shown below. Note, each parenthesized value is a theoretical value.

Asp; 1.02 (1), Thr; 1.92 (2), Ser; 1.82 (2),
Glu; 3.05 (3), Pro; 2.04 (2), Gly; 4.01 (4),
Ala; 3.87 (4), Val; 1.05 (1), Met; 1.10 (1),
Ile; 1.04 (1), Leu; 5.25 (5), Tyr; 1.01 (1),
Lys; 2.01 (2), His; 1.07 (1)

The above results of the amino acid analysis support the determination that the purified product obtained according to the above-mentioned process is peptide No. 16 having the amino acid composition shown in Table 1.

EXAMPLE 17

A purified product was prepared by using 11 g of the peptide-resin obtained in Example 4 by carrying out the same treatments as at procedures (6) and (7) of Example 1 and treating this peptide-resin in the same manner as described in Example 14, except that the coupling of threonine at step 27 of Example 14 and the coupling of asparagine at step 30 of Example 14 were changed as shown in Table 31.

TABLE 31

| Step | Protected Amino Acid | Coupling Conditions | | | |
|------|----------------------|---------------------|---|---|---|
| | | Amount used (g) | Solvent | Time Time (hours) | Coupling agent |
| 27 | Boc-Thr (Bzl) | 4.2 | DMF | 21.3 | DCC + HOBt |
| 30 | Bo&-Asn (Xan) | 1.7 | DMF | 24.0 | DCC |

The results of the amino acid analysis of the above purified product are shown below. Note, each parenthesized value is a theoretical value.

Asp; 1.00 (1), Thr; 2.74 (3), Ser; 1.64 (2),
Glu; 4.12 (4), Pro; 2.00 (2), Gly; 4.95 (5),
Ala; 3.90 (4), Val; 1.01 (1), Met; 1.13 (1),
Ile; 1.11 (1), Leu; 4.32 (4), Tyr; 1.22 (1),
Lys; 2.03 (2), His; 1.09 (1)

The above results of the amino acid analysis support the determination that the purified product prepared according to the above-mentioned process is peptide No. 17 having the composition shown in Table 1.

EXAMPLE 18

Protected amino acids shown in Table 32 were coupled in sequence to 15 g of the peptide-resin obtained at procedure (4) of Example 5.

After coupling glycine at step 31 and washing, the peptide-resin was taken out from the reaction vessel and dried, and alanine was coupled at step 32 by using 8.7 g of the obtained peptide-resin.

After coupling alanine at step 32 and washing, the peptide-resin was taken out from the reaction vessel and dried, and treated in the same manner as in Example 14 to obtain a purified product.

In Table 32, Bop represents Bop reagent and DIEA represents diisopropylethylamine.

TABLE 32

| | | Coupling Conditions | | | |
|---|---|---|---|---|---|
| Step | Protected Amino Acid | Amount used (g) | Solvent | Time Time (hours) | Coupling agent |
| 12 | Boc-Thr(Bzl) | 4.8 | DMF | 15.0 | DCC + HOBt |
| 13 | Boc-Gln | 4.9 | DMF | 15.0 | DCC + HOBt |
| 14 | Boc-Leu · $H_2O$ | 3.8 | DMF | 5.0 | DCC + HOBt |
| 15 | Boc-Lys(Cl-Z) | 4.8 | DMF | 15.0 | DCC + HOBt |
| 16 | Boc-His(Tos) | 7.5 | DMF | 3.0 | Bop-DIEA |
| 17 | Boc-Leu · $H_2O$ | 3.8 | DMF | 15.0 | DCC + HOBt |
| 18 | Boc-Glu(OBzl) | 6.2 | DMF | 3.0 | Bop + DIEA |
| 19 | Boc-Gln | 4.5 | DMF | 4.0 | Bop + DIEA |
| 20 | Boc-Ser(Bzl) | 5.4 | DMF | 9.0 | Bop + DIEA |
| 21 | Boc-Leu · $H_2O$ | 3.8 | DMF | 8.0 | DCC + HOBt |
| 22 | Boc-Lys(Cl-Z) | 4.8 | DMF | 10.0 | DCC + HOBt |
| 23 | Boc-Gly | 2.7 | DMF | 4.0 | DCC + HOBt |
| 24 | Boc-Leu · $H_2O$ | 4.6 | DMF | 3.0 | Bop + DIEA |
| 25 | Boc-Met | 4.6 | DMF | 3.0 | Bop + DIEA |
| 26 | Boc-Ala | 2.9 | DMF | 11.0 | DCC + HOBt |
| 27 | Boc-Thr(Bzl) | 5.7 | DMF | 4.0 | Bop + DIEA |
| | | 1.9 | DMF | 16.0 | Bop + DIEA |
| 28 | Boc-Ser(Bzl) | 4.6 | DMF | 12.0 | DCC + H6Bt |
| 29 | Boc-Leu · $H_2O$ | 4.6 | DMF | 3.0 | Bop + DIEA |
| 30 | Boc-Asn | 4.6 | DMF | 36.0 | DCC + HOBt |
| 31 | Boc-Gly | 3.2 | DMF | 4.0 | Bop + DIEA |
| 32 | Boc-Ala | 1.9 | DMF | 15.0 | Bop + DIEA |

The results of the amino acid analysis of the obtained purified product are shown below. Each parenthesized value is a theoretical value.

Asp; 1.02 (1), Thr; 3.60 (4), Ser; 2.73 (3),

Glu; 4.03 (4), Pro; 2.04 (2), Gly; 3.96 (4),

Ala; 2.98 (3), Met; 0.99 (1), Ile; 0.93 (1),

Leu; 5.16 (5), Tyr; 0.74 (1), Lys; 2.01 (2),

His; 0.96 (1)

The above results of the amino acid analysis support the conclusion that the purified product obtained by the above-mentioned process is peptide No. 18 having the amino acid composition shown in Table 1.

EXAMPLE 19

Protected amino acids shown in Table 33 are coupled in sequence to 8.5 g of the peptide-resin obtained at procedure (4) of Example 5.

After coupling glycine at step 31 and washing, the peptide-resin was taken out from the reaction vessel and dried. Alanine was coupled at step 32 by using 9.5 g of the dry peptide-resin.

After coupling alanine at step 32 and washing, the peptide-resin was treated in the same manner as in Example 14.

TABLE 33

| | | Coupling Conditions | | | |
|---|---|---|---|---|---|
| Step | Protected Amino Acid | Amount used (g) | Solvent | Time Time (hours) | Coupling agent |
| 12 | Boc-Thr(Bzl) | 2.7 | DMF | 15.0 | DCC + HOBt |
| 13 | Boc-Gln | 2.5 | DMF | 15.0 | DCC + HOBt |
| 14 | Boc-Leu · $H_2O$ | 3.2 | DMF | 15.0 | DCC + HOBt |
| 15 | Boc-Lys(Cl-Z) | 4.1 | DMF | 15.0 | DCC + HOBt |
| 16 | Boc-His(Tos) | 5.3 | $CH_2Cl_2$ | 15.0 | DCC |
| 17 | Boc-Leu · $H_2O$ | 3.2 | DMF | 15.0 | DCC + HOBt |
| 18 | Boc-Glu(OBzl) | 4.4 | DMF | 15.O | DCC + HOBt |
| 19 | Boc-Gln | 3.7 | DMF | 15.0 | DCC + HOBt |
| 20 | Boc-Ser(Bzl) | 3.8 | DMF | 15.0 | DCC + HOBt |
| 21 | Boc-Leu · $H_2O$ | 3.2 | DMF | 15.0 | DCC + HOBt |
| 22 | Boc-Lys(Cl-Z) | 4.1 | DMF | 15.0 | DCC + HOBt |
| 23 | Boc-Gly | 2.3 | DMF | 15.0 | DCC + HOBt |
| 24 | Boc-Leu · $H_2O$ | 3.2 | DMF | 15.0 | DCC + HOBt |
| 25 | Boc-Met | 3.2 | DMF | 15.0 | DCC + HOBt |
| 26 | Boc-Ala | 2.5 | DMF | 15.0 | DCC + HOBt |
| 27 | Boc-Ser(Bzl) | 3.8 | DMF | 15.0 | DCC + HOBt |
| 28 | Eoc-Thr(Bzl) | 4.1 | DMF | 15.0 | DCC + HOBt |
| 29 | Boc-Leu · $H_2O$ | 3.2 | DMF | 15.0 | DCC + HOBt |
| 30 | Boc-ABn | 3.5 | DMF | 15.0 | DCC + HOBt |
| | Boc-Asn(Xan) | 6.2 | DMF | 15.0 | DCC |
| 31 | Boc-Gly | 2.2 | DMF | 15.O | DCC + HOBt |
| 32 | Boc-Ala | 1.1 | DMF | 15.0 | DCC + HOBt |

The results of the amino acid analysis of the obtained purified product are shown below. Each parenthesized value is a theoretical value.

Asp; 1.01 (1), Thr; 3.60 (4), Ser; 2.76 (3),

Glu; 4.02 (4), Pro; 2.02 (2), Gly; 3.95 (4),

Ala; 2.97 (3), Met; 1.02 (1), Ile; 0.93 (1),

Leu; 5.08 (5), Tyr; 0.76 (1), Lys; 2.03 (2),

His; 0.96 (1)

The above results of the amino acid analysis support the conclusion that the purified product obtained by the above-mentioned process is peptide No. 19 having the amino acid composition shown in Table 1.

EXAMPLE 20

(1) By using 75 g of the peptide-resin obtained at procedure (4) of Example 1, protected amino acids shown in Table 34 were coupled in sequence.

TABLE 34

| | | Coupling Conditions | | | |
|---|---|---|---|---|---|
| Step | Protected Amino Acid | Amount used (g) | Solvent | Time Time (hours) | Coupling agent |
| 12 | Boc-Thr(Bzl) | 25.0 | DMF | 4.5 | BOP + DIEA |
| 13 | Boc-Gln | 20.0 | DMF | 15.0 | BOP + DIEA |
| 14 | Boc-Leu · $H_2O$ | 20.2 | DMF | 3.0 | BOP + DIEA |
| 15 | Boc-Lys(Cl-Z) | 25.5 | DMF | 4.0 | BOP + DIBA |
| 16 | Boc-His(Tos) | 33.2 | DMF | 4.0 | BOP + DIEA |
| 17 | Boc-Leu · $H_2O$ | 20.2 | DMF | 15.0 | BOP + DIEA |
| 18 | Boc-Glu(OBzl) | 27.3 | DMF | 3.0 | BOP + DIEA |
| 19 | Boc-Gln | 20.0 | DMF | 15.0 | BOP + DIEA |
| 20 | Boc-Ser(Bzl) | 20.9 | DMF | 15.0 | BOP + DIEA |
| 21 | Boc-Leu · $H_2O$ | 20.2 | DMF | 3.0 | BOP + DIEA |

After coupling leucine at step 21 and washing, the peptide-resin was taken out from the reaction vessel and dried.

(2) By using 15 g of the peptide-resin obtained at procedure (1), protected amino acids shown in Table 35 were coupled in sequence.

TABLE 35

| | | Coupling Conditions | | | |
|---|---|---|---|---|---|
| Step | Protected Amino Acid | Amount used (g) | Solvent | Time Time (hours) | Coupling agent |
| 22 | Boc-Lys(Cl-Z) | 2.7 | DMF | 10.0 | BOP + DIEA |
| 23 | Boc-Gly | 1.5 | DMF | 8.0 | BOP + DIKA |
| 24 | Boc-Leu · H$_2$O | 2.2 | DMF | 4.0 | BOP + DIEA |
| 25 | Boc-Leu · H$_2$O | 2.2 | DMF | 4.0 | BOP + DIEA |
| 26 | Boc-Ala | 1.6 | DMF | 9.0 | BOP + DIEA |
| 27 | Boc-Thr(Bzl) | 2.7 | DMF | 8.0 | BOP + DIEA |
| 28 | Boc-Ser(Bzl) | 2.6 | DMF | 12.0 | BOP + DIEA |
| 29 | Boc-Leu · H$_2$O | 2.2 | DMF | 3.0 | BOP + DIEA |
| 30 | Boc-Asn | 2.7 | CH$_2$CL$_2$ | 41.0 | DCC + HOBt |
| 31 | Boc-Gly | 1.5 | DMF | 5.0 | BOP + DIEA |
| 32 | Boc-Ala | 1.6 | DMF | 14.0 | BOP + DIEA |

After coupling alanine at step 32 and washing, the peptide-resin was taken out from the reaction vessel and dried. Then, the peptide-resin was treated in the same manner as in Example 14.

The results of the amino acid analysis of the obtained purified product are shown below. Each parenthesized value is a theoretical value.

Asp; 1.03 (1), Thr; 2.78 (3), Ser; 1.76 (2),
Glu; 4.06 (4), Pro; 2.02 (2), Gly; 3.98 (4),
Ala; 3.96 (4), Met; 1.02 (1), Ile; 0.99 (1),
Leu; 6.09 (6), Tyr; 0.96 (1), Lys; 1.96 (2),
His; 1.09 (1)

The above results of the amino acid analysis support the conclusion that the purified product obtained by the above-mentioned process is peptide No. 20 having the amino acid concentration shown in Table 1.

EXAMPLE 21

By using 5 g of the peptide-resin obtained at procedure (1) of Example 9, protected amino acids shown in Table 36 were coupled in sequence.

In Table 36, Asu (OBu$^t$) represents L-α-aminosuberic acid-ω-tertiary-butyl ester and OPf$_p$ represents pentafluorophenyl ester.

TABLE 36

| | | Coupling Conditions | | | |
|---|---|---|---|---|---|
| Step | Protected Amino Acid | Amount used (g) | Solvent | Time Time (hours) | Coupling agent |
| 25 | Boc-Met | 0.8 | DMF | 4.0 | BOP + DIEA |
| 26 | Fmoc-Asu(OBu$^t$) | 1.5 | DMF | 8.0 | BOP + DIEA |
| 27 | Fmoc-Thr(Bzl) | 1.4 | DMF | 16.0 | BOP + DIEA |
| 28 | Fmoc-Ser(Bzl) | 1.4 | DMF | 16.0 | BOB + DIEA |
| 29 | Fmoc-Leu | 1.2 | DMF | 4.0 | BOP + DIEA |
| 30 | Fmoc-Asn-OPfp | 2.2 | DMF | 16.0 | HOBt |
| 31 | Fmoc-Cly | 1.0 | DMF | 4.0 | BOP + DIEA |

After coupling glycine at step 31 and washing, the peptide-resin was stirred in the following solvents in sequence and filtered.

100 ml of 75% TEA/methylene chloride +0.5 g of phenol (30 minutes)

Methylene chloride, ethanol and chloroform (75 ml each, two times)

10 ml of TEA +65 ml of chloroform 75 ml of DMF (two times)

100 ml of 20% piperidine/DMF (20 minutes)

Methylene chloride, ethanol and chloroform (75 ml each, two times)

75 ml of 2 g Bop/DMF (16 hours, three times)

After washing, the peptide-resin was taken out from the reaction vessel and dried, and treated in the same manner as in Example 14 to obtain a purified product.

The results of the amino acid analysis of the obtained purified product are shown below. Each parenthesized value is a theoretical value.

Asp; 1.02 (1), Thr; 2.62 (3), Ser; 1.71 (2),
Glu; 4.06 (4), Pro; 2.02 (2), Gly; 3.96 (4),
Ala; 1.98 (2), Val; 0.97 (1), Met; 1.10 (1),
Ile; 1.03 (1), Leu; 5.43 (5), Tyr; 1.12 (1),
Lys; 1.96 (2), His; 1.10 (1), Asu; 1.63 (2)

The above-results of the amino acid analysis support the conclusion that the purified product obtained by the above-mentioned process is peptide No. 21 having the amino acid composition shown in Table 1.

EXAMPLE 22

By using 12 g of the peptide-resin obtained at procedure (1) of Example 20, protected amino acids shown in Table 37 were coupled in sequence.

TABLE 37

| | | Coupling Conditions | | | |
|---|---|---|---|---|---|
| Step | Protected Amino Acid | Amount used (g) | Solvent | Time Time (hours) | Coupling agent |
| 22 | Boc-Lys(Cl-Z) | 2.7 | DMF | 15.0 | BOP + DIEA |
| 23 | Boc-Gly | 1.5 | DMF | 15.0 | BOP + DIEA |
| 24 | Boc-Leu · H$_2$O | 2.2 | DMF | 4.0 | BOP + DIEA |
| 25 | Boc-Leu · H$_2$O | 2.2 | DMF | 5.5 | BOP + DIEA |
| 26 | Fmoc-Asu(OBu$^t$) | 4.0 | DMF | 19.0 | BOP + DIEA |
| 27 | Fmoc-Thr(Bzl) | 3.7 | DMF | 21.0 | BOP + DIEA |
| 28 | Fmoc-Ser(Bzl) | 3.6 | DMF | 20.0 | BOP + DIEA |
| 29 | Fmoc-Leu | 3.1 | DMF | 5.0 | BOP + DIEA |
| 30 | Fmoc-Asn-OPfp | 2.2 | DMF | 20.0 | HOBt |
| 31 | Boc-Gly | 1.5 | DMF | 4.0 | BOP + DIEA |

After coupling glycine at step 31 and washing, the peptide-resin was stirred in the following solvents in sequence and filtered.

125 ml of 75% TEA/methylene chloride +0.5 g of phenol (5 minutes and 25 minutes)

Methylene chloride, ethanol and chloroform (75 ml each, two times)

10 ml of TEA +65 ml of chloroform Methylene chloride, ethanol and chloroform (75 ml each, two times)

75 ml of 2 g Bop/DMF (24 hours)

After washing, the peptide-resin was taken out from the reaction vessel and dried, and treated in the same manner as in Example 14 to obtain a purified product.

The results of the amino acid analysis of the obtained purified product are shown below. Each parenthesized value is a theoretical value.

Asp; 1.02 (1), Thr; 2.65 (3), Ser; 1.99 (2),
Glu; 4.03 (4), Pro; 1.79 (2), Gly; 3.97 (4),

Ala; 1.94 (2), Val; 1.04 (1), Ile; 0.98 (1),

Leu; 6.26 (6), Tyr; 0.96 (1), Lys; 2.04 (2),

His; 1.02 (1), Asu; 1.62 (2)

The above-results of the amino acid analysis support the conclusion that the purified product obtained by the above-mentioned process is peptide No. 22 having the amino acid composition shown in Table 1.

EXAMPLE 23

By using 12 g of the peptide-resin obtained at procedure (1) of Example 20, protected amino acids shown in Table 38 were coupled in sequence.

TABLE 38

| | | Coupling Conditions | | | |
|---|---|---|---|---|---|
| Step | Protected Amino Acid | Amount used (g) | Solvent | Time (hours) | Coupling agent |
| 22 | Boc-Lys(Cl-Z) | 3.0 | DMF | 3.0 | BOP + DIEA |
| | | 1.0 | DMF | 2.0 | BOP + DIEA |
| 23 | Boc-Gly | 1.7 | DMF | 15.0 | BOP + DIEA |
| 24 | Boc-Leu · $H_2O$ | 2.4 | DMF | 3.5 | BOP + DIEA |
| 25 | Boc-Met | 2.4 | DMF | 4.0 | BOP + DIEA |
| 26 | Fmoc-Lys(Boc) | 4.5 | DMF | 16.0 | BOP + DIEA |
| 27 | Fmoc-Thr(OBu$^t$) | 3.8 | DMF | 10.0 | BOP + DIEA |
| | | 1.2 | DMF | 16.0 | BOP + DIEA |
| 28 | Fmoc-Ser(OBu$^t$) | 3.6 | DMF | 5.0 | BOP + DIEA |
| 29 | Fmoc-Leu | 3.4 | DMF | 3.5 | BOP + DIEA |
| 30 | Fmoc-Asn-OPfp | 5.6 | DMF | 15.0 | HOBt + BOP + DIEA |
| | | 2.8 | DMF | 15.0 | BOP + DIEA |
| 31 | Fmoc-Asp(OBu$^t$) | 3.9 | DMF | 16.0 | BOP + DIEA |

After coupling asparagine at step 31 and washing, peptide-resin was treated in the same manner as in Example 21 to obtain a purified product, except that 4.3 g of Bop was dissolved in 100 ml of 1-methyl-2-pyrrolidone and 3 ml of DIEA was added to the solution, and the mixture was reacted for 24 hours.

The results of the amino acid analysis of the obtained purified product are shown below. Each parenthesized value is a theoretical value.

Asp; 1.94 (2), Thr; 2.77 (3), Ser; 1.71 (2),

Glu; 4.13 (4), Pro; 2.05 (2), Gly; 3.02 (3),

Ala; 2.01 (2), Val; 1.01 (1), Met; 1.03 (1),

Ile; 1.07 (1), Leu; 5.19 (5), Tyr; 0.98 (1),

Lys; 2.91 (3), His; 1.03 (1)

The above-results of the amino acid analysis support the conclusion that the purified product obtained by the above-mentioned process is peptide No. 23 having the amino acid composition shown in Table 1.

EXAMPLE 24

A purified product was obtained by subjecting 12 g of the peptide-resin obtained at procedure (1) of Example 20 to the operations as in Example 23 except that instead of coupling methionine at step 25 of Example 23, the coupling of leucine was carried out, as shown in Table 39.

TABLE 39

| | | Coupling Conditions | | | |
|---|---|---|---|---|---|
| Step | Protected Amino Acid | Amount used (g) | Solvent | Time (hours) | Coupling agent |
| 25 | Boc-Leu.$H_2O$ | 2.4 | DMF | 3.5 | BOP + DIEA |

The results of the amino acid analysis of the obtained purified product are shown below. Each parenthesized value is a theoretical value.

Asp; 1.94 (2), Thr; 2.80 (3), Ser; 1.70 (2),

Glu; 4.08 (4), Pro; 2.06 (2), Gly; 3.06 (3),

Ala; 2.01 (2), Val; 1.19 (1), Ile; 0.98 (1),

Leu; 6.09 (6), Tyr; 0.97 (1), Lys; 2.91 (3),

His; 1.17 (1)

The above-results of the amino acid analysis support the conclusion that the purified product obtained by the above-mentioned process is peptide No. 24 having the amino acid composition shown in Table 1.

EXAMPLE 25

By using 12 g of the peptide-resin obtained at procedure (1) of Example 20, protected amino acids shown in Table 40 were coupled in sequence.

TABLE 40

| | | Coupling Conditions | | | |
|---|---|---|---|---|---|
| Step | Protected Amino Acid | Amount used (g) | Solvent | Time (hours) | Couling agent |
| 22 | Boc-Lys(Cl—Z) | 2.7 | DMF | 14.0 | BOP + DIEA |
| 23 | Boc-Gly | 1.5 | DMF | 14.0 | BOP + DIEA |
| 24 | Boc-Leu.$H_2O$ | 2.2 | DMF | 4.5 | BOP + DIEA |
| 25 | Boc-Leu.$H_2O$ | 2.2 | DMF | 14.0 | BOP + DIEA |
| 26 | Boc-Lys($\epsilon$-Fmoc) | 4.1 | DMF | 15.0 | BOP + DIEA |
| 27 | Boc-Thr(Bzl) | 1.3 | DMF | 16.0 | BOP + DIEA |
| 28 | Boc-Ser(Bzl) | 3.5 | DMF | 15.0 | BOP + DIEA |
| 29 | Boc-Leu.$H_2O$ | 2.2 | DMF | 4.5 | BOP + DIEA |
| 30 | Boc-Asn | 3.3 | DMF | 60.0 | DCC + HOBt |
| 31 | Boc-Asp(O$^\beta$-Fmoc) | 3.6 | DMF | 18.0 | BOP + DIEA |

After coupling aspartic acid at step 31 and washing, the peptide-resin was stirred in the following solvents in sequence and filtered.

100 ml of DMF (2 minutes, two times)

125 ml of 20% piperidine/DMF (20 minutes)

Methylene chloride, ethanol and methylene chloride (100 ml each, 2 minutes, two times)

125 ml of 7.8 g Bop/1-methyl-2-pyrrolidone +5 ml of DIEA +2.4 g of HOBt (15 hours)

Methylene chloride, ethanol and methylene chloride (100 ml each, 2 minutes, two times)

100 ml of 3.5 g Bop/1-methyl-2-pyrrolidone +3 ml of DIEA +1.2 g of HOBt (43 hours)

Methylene chloride, ethanol and chloroform (100 ml each, 2 minutes, two times)

25 ml of 10% TEA/100 ml of chloroform (5 minutes) +1.7 ml of acetic anhydride (60 minutes)

Methylene chloride, ethanol and methylene chloride (100 ml each, 2 minutes, two times)

125 ml of 50% TFA/methylene chloride (5 minutes and 30 minutes)

Methylene chloride, ethanol and chloroform (100 ml each, 2 minutes, two times)

25 ml of 10% TEA +100 ml of chloroform (5 minutes and 15 minutes)

Methylene chloride, ethanol and chloroform (100 ml each, 2 minutes, two times)

25 ml of 10% TEA/100 ml of chloroform (5 minutes) +1.7 ml of acetic anhydride (60 minutes)

Methylene chloride, ethanol and methylene chloride (100 ml each, 2 minutes, two times)

After washing, the peptide-resin was taken out from the reaction vessel and dried, and treated in the same manner as in Example 14 to obtain a purified product.

The results of the amino acid analysis of the obtained purified product are shown below. Each parenthesized value is a theoretical value.

Asp; 1.88 (2), Thr; 2.81 (3), Ser; 1.97 (2),

Glu; 4.16 (4), Pro; 1.93 (2), Gly; 3.10 (3),

Ala; 1.97 (2), Val; 1.12 (1), Ile; 1.04 (1),

Leu; 6.44 (6), Tyr; 0.96 (1), Lys; 2.96 (3),

His; 1.01 (1)

The above-results of the amino acid analysis support the conclusion that the purified product obtained by the above-mentioned process is peptide No. 25 having the amino acid composition shown in Table 1.

EXAMPLE 26

By using 12 g of the peptide-resin obtained at procedure (1) of Example 20, protected amino acids shown in table 41 were coupled in sequence.

TABLE 41

| | | Coupling Conditions | | | |
|---|---|---|---|---|---|
| Step | Protected Amino Acid | Amount used (g) | Solvent | Time (hours) | Coupling agent |
| 22 | Boc-Lys(Cl—Z) | 2.7 | DMF | 14.0 | BOP + DIEA |
| 23 | Boc-Gly | 1.5 | DMF | 14.0 | BOP + DIEA |
| 24 | Boc-Leu.H$_2$O | 2.2 | DMF | 4.5 | BOP + DIEA |
| 25 | Boc-Leu.H$_2$O | 2.2 | DMF | 14.0 | BOP + DIEA |
| 26 | Boc-Lys($\epsilon$-Fmoc) | 4.1 | DMF | 15.0 | BOP + DIEA |
| 27 | Boc-Thr(Bzl) | 1.3 | DMF | 16.0 | BOP + DIEA |
| 28 | Boc-Ser(Bzl) | 3.5 | DMF | 15.0 | BOP + DIEA |
| 29 | Boc-Leu.H$_2$O | 2.2 | DMF | 4.5 | BOP + DIEA |
| 30 | Boc-Asn | 3.3 | DMF | 60.0 | DCC + HOBt |
| 31 | Succinic Anhydride | 1.5 | CHCl$_3$ | 4.0 | — |

After coupling succinic anhydride at step 31 and washing, the peptide-resin was stirred in the following solvents in sequence and filtered.

100 ml of DMF (2 minutes, two times)

125 ml of 20% piperidine/DMF (20 minutes)

Methylene chloride, ethanol and methylene chloride (100 ml each, 2 minutes, two times)

125 ml of 7.8 g Bop/1-methyl-2-pyrrolidone +5 ml of DIEA +2.4 g of HOBt (15 hours)

Methylene chloride, ethanol and methylene chloride (100 ml each, 2 minutes, two times)

125 ml of 2.6 g Bop/1-methyl-2-pyrrolidone +1.7 ml of DIEA +0.8 g of HOBt (15 hours, two times)

After washing, the peptide-resin was taken out from the reaction vessel and dried, and treated in the same manner as in Example 14 to obtain a purified product.

The results of the amino acid analysis of the obtained purified product are shown below. Each parenthesized value is a theoretical value.

Asp; 1.00 (1), Thr; 2.67 (3), Ser; 1.90 (2),

Glu; 4.08 (4), Pro; 1.81 (2), Gly; 2.98 (3),

Ala; 1.94 (2), Val; 1.03 (1), Ile; 1.01 (1),

Leu; 6.29 (6), Tyr; 0.97 (1), Lys; 2.99 (3),

His; 1.04 (1)

The above-results of the amino acid analysis support the conclusion that the purified product obtained by the above-mentioned process is peptide No. 26 having the amino acid composition shown in Table 1.

EXAMPLE 27

A purified product was obtained by subjecting 12 g of the peptide-resin at procedure (1) of Example 20 to the operations as in Example 23 except that instead of coupling lysine at step 26, the coupling of aspartic acid was carried out as shown in Table 42, and the coupling of threonine and the second coupling of asparagine were not carried out.

TABLE 42

| | | Coupling Conditions | | | |
|---|---|---|---|---|---|
| Step | Protected Amino Acid | Amount used (g) | Solvent | Time (hours) | Coupling agent |
| 26 | Fmoc-Asp(OBu$^t$) | 3.9 | DMF | 16.0 | BOP + DIEA |
| 31 | Fmoc-Lys(Boc) | 4.5 | DMF | 16.0 | BOP + DIEA |

The results of the amino acid analysis of the obtained purified product are shown below. Each parenthesized value is a theoretical value.

Asp; 1.98 (2), Thr; 2.78 (3), Ser; 1.71 (2),

Glu; 4.13 (4), Pro; 2.04 (2), Gly; 2.98 (3),

Ala; 1.99 (2), Val; 1.09 (1), Met; 1.10 (1),

Ile; 1.16 (1), Leu; 5.25 (5), Tyr; 1.04 (1),

Lys; 2.92 (3), His; 1.13 (1)

The above-results of the amino acid analysis support the conclusion that the purified product obtained by the above-mentioned process is peptide No. 27 having the amino acid composition shown in Table 1.

EXAMPLE 28

A purified product was obtained by subjecting 12 g of the peptide-resin at procedure (1) of Example 20 to the operations as in Example 23 except that instead of coupling methionine at step 25 at operation (1) of Example 23, the coupling of leucine was carried out, instead of coupling lysine at step 26, the coupling of aspartic acid was carried out, and instead of coupling aspartic acid at step 31, the coupling of lysine was carried out, as shown in Table 43. The coupling of threonine and the second coupling of asparagine were not carried out.

TABLE 43

| Step | Protected Amino Acid | Coupling Conditions | | | |
|---|---|---|---|---|---|
| | | Amount used (g) | Solvent | Time (hours) | Coupling agent |
| 25 | Boc-Leu.H$_2$O | 2.4 | DMF | 3.5 | BOP + DIEA |
| 26 | Fmoc-Asp(OBu$^t$) | 3.9 | DMF | 16.0 | BOP + DIEA |
| 31 | Fmoc-Lys(Boc) | 4.5 | DMF | 16.0 | BOP + DIEA |

The results of the amino acid analysis of the obtained purified product are shown below. Each parenthesized value is a theoretical value.

Asp; 1.94 (2), Thr; 2.77 (3), Ser; 1.73 (2),
Glu; 4.09 (4), Pro; 1.99 (2), Gly; 2.96 (3),
Ala; 2.14 (2), Val; 1.01 (1), Ile; 0.99 (1),
Leu; 6.07 (6), Tyr; 0.95 (1), Lys; 2.87 (3),
His; 1.09 (1)

The above-results of the amino acid analysis support the conclusion that the purified product obtained by the above-mentioned process is peptide No. 28 having the amino acid composition shown in Table 1.

EXAMPLE 29

By using 13 g of the peptide-resin obtained at procedure (1) of Example 9, protected amino acids shown in Table 44 were coupled in sequence.

In Table 44, Orn represents ornithine.

TABLE 44

| Step | Protected Amino Acid | Coupling Conditions | | | |
|---|---|---|---|---|---|
| | | Amount used (g) | Solvent | Time (hours) | Coupling agent |
| 25 | Boc-Leu.H$_2$O | 2.0 | DMF | 12.0 | BOP + DIEA |
| 26 | Boc-Orn(Fmoc) | 3.7 | DMF | 16.0 | BOP + DIEA |
| 27 | Boc-Thr(Bzl) | 2.5 | DMF | 20.0 | BOP + DIEA |
| | | 1.5 | DMF | 20.0 | BOP + DIEA |
| 28 | Boc-Ser(Bzl) | 3.2 | DMF | 20.0 | BOP + DIEA |
| 29 | Boc-Leu.H$_2$O | 2.7 | DMF | 4.0 | BOP + DIEA |
| 30 | Boc-Asn | 8.0 | DMF | 40.0 | DCC + HOBt |
| 31 | Boc-Glu(O$^\beta$-Fmoc) | 4.6 | DMF | 20.0 | BOP + DIEA |

After coupling glutamic acid at step 31 and washing, the peptide-resin was treated in the manner as in Example 26.

The results of the amino acid analysis of the obtained purified product are shown below. Each parenthesized value is a theoretical value.

Asp; 0.99 (1), Thr; 2.75 (3), Ser; 1.88 (2),
Glu; 5.16 (5), Pro; 1.92 (2), Gly; 3.01 (3),
Ala; 2.00 (2), Val; 1.05 (1), Ile; 0.99 (1),
Leu; 6.33 (6), Tyr; 0.97 (1), Lys; 1.91 (2),
His; 1.02 (1), Ornithine; 1.22 (1)

The above-results of the amino acid analysis support the conclusion that the purified product obtained by the above-mentioned process is peptide No. 29 having the amino acid composition shown in Table 1.

EXAMPLE 30

A purified product was obtained by subjecting 13 g of the peptide-resin at procedure (1) of Example 9 to the operations as in Example 29 except that instead of coupling ornithine at step 26, the coupling of glutamic acid was carried out, and instead of coupling glutamic acid at step 31, the coupling of ornithine was carried out, as shown in Table 45.

TABLE 45

| Step | Protected Amino Acid | Coupling Conditions | | | |
|---|---|---|---|---|---|
| | | Amount used (g) | Solvent | Time (hours) | Coupling agent |
| 26 | Boc-Glu(O$^\beta$-Fmoc) | 3.4 | DMF | 16.0 | BOP + DIEA |
| 31 | Boc-Orn(Fmoc) | 4.9 | DMF | 20.0 | BOP + DIEA |

The results of the amino acid analysis of the obtained purified product are shown below. Each parenthesized value is a theoretical value.

Asp; 0.97 (1), Thr; 2.64 (3), Ser; 1.73 (2),
Glu; 5.15 (5), Pro; 1.92 (2), Gly; 3.05 (3),
Ala; 2.01 (2), Val; 1.04 (1), Ile; 1.09 (1),
Leu; 6.42 (6), Tyr; 0.94 (1), Lys; 1.89 (2),
His; 1.02 (1), Ornithine; 1.21 (1)

The above-results of the amino acid analysis support the conclusion that the purified product obtained by the above-mentioned process is peptide No. 30 having the amino acid composition shown in Table 1.

EXAMPLE 31

(1) By using 20 g of the peptide-resin obtained at procedure (4) of Example 1, protected amino acids shown in Table 46 were coupled in sequence.

TABLE 46

| Step | Protected Amino Acid | Coupling Conditions | | | |
|---|---|---|---|---|---|
| | | Amount used (g) | Solvent | Time (hours) | Coupling agent |
| 12 | Boc-Thr(Bzl) | 6.7 | DMF | 13.0 | BOP + DIEA |
| 13 | Boc-His(Tos) | 8.8 | DMF | 5.5 | BOP + DIEA |
| 14 | Boc-Phe | 5.7 | DMF | 4.0 | BOP + DIEA |
| 15 | Boc-Lys(Cl—Z) | 6.8 | DMF | 16.0 | BOP + DIEA |
| 16 | Boc-Asn | 6.7 | CH$_2$Cl$_2$ | 46.0 | DCC – HOBt |
| 17 | Boc-Leu.H$_2$O | 5.4 | DMF | 5.5 | BOP + DIEA |
| 18 | Boc-Asp(OBzl) | 7.0 | DMF | 14.0 | BOP + DIEA |
| 19 | Boc-Gln | 5.3 | DMF | 5.0 | BOP + DIEA |
| 20 | Boc-Ser(Bzl) | 6.4 | DMF | 14.0 | BOP + DIEA |
| 21 | Boc-Leu.H$_2$O | 5.4 | DMF | 5.0 | BOP + DIEA |
| 22 | Boc-Lys(Cl—Z) | 6.8 | DMF | 14.0 | BOP + DIEA |
| 23 | Boc-Gly | 5.0 | DMF | 5.0 | BOP + DIEA |
| 24 | Boc-Leu.H$_2$O | 5.4 | DMF | 13.0 | BOP + DIEA |

After coupling leucine at step 24 and washing, the peptide-resin was taken out from the reaction vessel and dried.

(2) By using 15 g of the peptide-resin obtained at procedure (1), protected amino acids shown in Table 47 were coupled in sequence, and the peptide-resin was treated in the manner as in Example 26 to obtain a purified product.

TABLE 47

| Step | Protected Amino Acid | Amount used (g) | Solvent | Time (hours) | Coupling agent |
|---|---|---|---|---|---|
| 25 | Boc-Leu.H₂O | 2.4 | DMF | 4.5 | BOP + DIEA |
| 26 | Boc-Lys(ε-Fmoc) | 4.5 | DMF | 16.0 | BOP + DIEA |
| 27 | Boc-Thr(Bzl) | 3.0 | DMF | 16.0 | BOP + DIEA |
|  |  |  | DMF | 4.0 | BOP + DIEA |
| 28 | Boc-Ser(Bzl) | 3.6 | DMF | 16.0 | BOP + DIEA |
| 29 | Boc-Leu.H₂O | 2.4 | DMF | 4.5 | BOP − DIEA |
| 30 | Boc-Asn | 3.7 | CH₂Cl₂ | 60.0 | DCC + HOBt |
| 31 | Boc-Asp(Oᵝ-Fmoc) | 3.9 | DMF | 18.0 | BOP + DIEA |

The results of the amino acid analysis of the obtained purified product are shown below. Each parenthesized value is a theoretical value.

Asp; 3.85 (4), Thr; 2.67 (3), Ser; 1.94 (2),
Glu; 2.07 (2), Pro; 2.00 (2), Gly; 3.03 (3),
Ala; 1.99 (2), Val; 1.10 (1), Ile; 1.02 (1),
Leu; 5.36 (5), Tyr; 0.99 (1), Phe; 1.06 (1),
Lys; 3.05 (3), His; 1.03 (1)

The above-results of the amino acid analysis support the conclusion that the purified product obtained by the above-mentioned process is peptide No. 31 having the amino acid composition shown in Table 1.

EXAMPLE 32

By using 15 g of the peptide-resin obtained at procedure (1) of Example 31, protected amino acids shown in Table 48 were coupled in sequence, and the peptide-resin was treated in the manner as in Example 26 to obtain a purified product.

TABLE 48

| Step | Protected Amino Acid | Amount used (g) | Solvent | Time (hours) | Coupling agent |
|---|---|---|---|---|---|
| 25 | Boc-Leu.H₂O | 1.9 | DMF | 6.0 | BOP + DIEA |
| 26 | Boc-Lys(ε-Fmoc) | 3.6 | DMF | 17.0 | BOP + DIEA |
| 27 | Boc-Thr(Bzl) | 2.4 | DMF | 18.0 | BOP + DIEA |
| 28 | Boc-Ser(Bzl) | 2.3 | DMF | 17.0 | BOP + DIEA |
| 29 | Boc-Leu.H₂O | 1.9 | DMF | 3.0 | BOP + DIEA |
| 30 | Boc-Asn | 3.9 | DMF | 44.0 | DCC + HOBt |
| 31 | Succinic Anhydride | 1.5 | DMF | 4.0 | — |

The results of the amino acid analysis of the obtained purified product are shown below. Each parenthesized value is a theoretical value.

Asp; 3.01 (3), Thr; 2.87 (3), Ser; 1.78 (2),
Glu; 2.01 (2), Pro; 1.97 (2), Gly; 3.02 (3),
Ala; 1.99 (2), Val; 1.06 (1), Ile; 1.01 (1),
Leu; 5.19 (5), Tyr; 1.01 (1), Phe; 1.02 (1),
Lys; 3.00 (3), His; 1.12 (1)

The above-results of the amino acid analysis support the conclusion that the purified product obtained by the above-mentioned process is peptide No. 32 having the amino acid composition shown in Table 1.

EXAMPLE 33

By using 16 g of the peptide-resin obtained at procedure (4) of Example 1, protected amino acids shown in Table 49 were coupled in sequence.

TABLE 49

| Step | Protected Amino Acid | Amount used (g) | Solvent | Time (hours) | Coupling agent |
|---|---|---|---|---|---|
| 12 | Boc-Thr(Bzl) | 5.2 | DMF | 17.0 | BOP + DIEA |
| 13 | Boc-His(Tos) | 6.9 | DMF | 6.0 | BOP + DIEA |
| 14 | Boc-Phe | 4.5 | DMF | 15.0 | BOP + DIEA |
| 15 | Boc-Lys(Cl—Z) | 5.3 | DMF | 4.0 | BOP + DIEA |
| 16 | Boc-Asn | 5.2 | CH₂Cl₂ | 13.0 | DCC + HOBt |
| 17 | Boc-Leu.H₂O | 4.2 | DMF | 4.0 | BOP + DIEA |
| 18 | Boc-Asp(OBzl) | 5.5 | DMF | 4.5 | BOP + DIEA |
| 19 | Boc-Gln | 4.2 | DMF | 8.0 | BOP + DIEA |
| 20 | Boc-Thr(Bzl) | 5.2 | DMF | 5.5 | BOP + DIEA |
| 21 | Boc-Leu.H₂O | 4.2 | DMF | 6.0 | BOP + DIEA |
| 22 | Boc-Lys(Cl—Z) | 5.3 | DMF | 9.0 | BOP + DIEA |
| 23 | Boc-Gly | 3.0 | DMF | 9.0 | BOP + DIEA |
| 24 | Boc-Leu.H₂O | 4.2 | DMF | 10.0 | BOP + DIEA |
| 25 | Boc-Leu.H₂O | 4.2 | DMF | 26.0 | BOP + DIEA |
| 26 | Boc-Lys(ε-Fmoc) | 7.9 | DMF. | 17.0 | BOP + DIEA |
| 27 | Boc-Thr(Bzl) | 5.2 | DMF | 22.0 | BOP + DIEA |
| 28 | Boc-Ser(Bzl) | 5.0 | DMF | 16.0 | BOP + DIEA |
| 29 | Boc-Leu.H₂O | 4.2 | DMF | 4.0 | BOP + DIEA |
| 30 | Boc-Asn | 3.9 | DMF | 17.0 | BOP + DIEA |
|  |  | 2.0 | DMF | 7.0 | BOP + DIEA |
| 31 | Succinic Anhydride | 1.7 | DMF | 2.0 | — |

After coupling succinic anhydride at step 31 and washing, the peptide-resin was treated in the manner as in Example 26.

The results of the amino acid analysis of the obtained purified product are shown below. Each parenthesized value is a theoretical value, Asp; 2.97 (3), Thr; 3.62 (4), Ser; 0.89 (1),
Glu; 2.00 (2), Pro; 2.08 (2), Gly; 3.07 (3),
Ala; 1.98 (2), Val; 1.05 (1), Ile; 0.99 (1),
Leu; 5.14 (5), Tyr; 1.14 (1), Phe; 1.00 (1),
Lys; 2.59 (3), His; 0.98 (1)

The above-results of the amino acid analysis support the conclusion that the purified product obtained by the above-mentioned process is peptide No. 33 having the amino acid composition shown in Table 1.

EXAMPLE 34

(1) Activation of Resin 50 g of the BHA resin as described in Example 1 was activated in the same manner as at procedure (1) of Example 1 except that the amount of the solvent was adjusted to ⅓ of the amount used in Example 1.

(2) Steps 1–24

By using all of the resin obtained at procedure (1), protected amino acids shown in Table 50 were coupled in sequence. DMF was used as the coupling solvent and BOP and DIEA were used as the coupling agent.

TABLE 50

| Step | Protected Amino Acid | Amount used (g) | Time (hours) |
|---|---|---|---|
| 1 | Boc-Pro | 21.5 | 2.8 |
| 2 | Boc-Ala | 19.0 | 2.5 |
| 3 | Boc-Gly | 17.5 | 2.0 |
| 4 | Boc-Val | 21.8 | 2.0 |

TABLE 50-continued

| | | Coupling Conditions | |
|---|---|---|---|
| Step | Protected Amino Acid | Amount used (g) | Time (hours) |
| 5 | Boc-Gly | 17.5 | 3.0 |
| 6 | Boc-Ile.½H$_2$O | 24.0 | 2.5 |
| 7 | Boc-Ala | 19.0 | 2.0 |
| 8 | Boc-Thr(Bzl) | 31.0 | 2.0 |
| 9 | Boc-Gln | 24.5 | 2.5 |
| 10 | Boc-Pro | 21.5 | 4.0 |
| | | 5.4 | 2.0 |
| 11 | Boc-Phe | 31.9 | 19.0 |
| | | 15.9 | 16.0 |
| 12 | Boc-Thr(Bzl) | 37.1 | 19.0 |
| 13 | Boc-His(Tos) | 49.1 | 23.0 |
| 14 | Boc-Phe | 31.9 | 4.0 |
| 15 | Boc-Lys (Cl—Z) | 50.0 | 16.0 |
| 16 | Boc-Asn | 27.9 | 4.0 |
| | | 13.9 | 15.0 |
| 17 | Boc-Phe | 31.9 | 4.0 |
| 18 | Boc-Asp (OBzl) | 38.8 | 17.0 |
| 19 | Boc-Gln | 30.0 | 4.0 |
| 20 | Boc-Thr(Bzl) | 37.1 | 16.0 |
| | | 18.6 | 4.0 |
| 21 | Boc-Tyr(Br—Z) | 59.5 | 15.0 |
| 22 | Boc-Thr-(Bzl) | 37.1 | 4.0 |
| 23 | Boc-Gly | 21.0 | 16.0 |
| 24 | Boc-Leu.H$_2$O | 29.9 | 20.0 |

After coupling leucine at step 24 and washing, the peptide-resin was taken out from the reaction vessel and dried.

Steps 25–31

By using 15 g of the peptide-resin obtained at procedure (2), protected amino acids shown in Table 51 were coupled in sequence. The same coupling solvent and coupling agent were used except that DCC and HOBt were used as the coupling agent for the third coupling at step 30 and, at step 31, a 10% solution of TEA in chloroform was used as the coupling solvent and no coupling agent was used.

TABLE 51

| | | Coupling Conditions | |
|---|---|---|---|
| Step | Protected Amino Acid | Amount used (g) | Time (hours) |
| 25 | Boc-Met | 2.5 | 4.0 |
| 26 | Boc-Lys(ε-Fmoc) | 4.6 | 18.5 |
| 27 | Boc-Thr(Bzl) | 3.0 | 19.0 |
| 28 | Boc-Ser(Bzl) | 2.9 | 24.0 |
| | | 2.9 | 48.0 |
| 29 | Boc-Leu.H$_2$O | 2.5 | 4.0 |
| 30 | Boc-Asn | 3.1 | 17.0 |
| | | 2.3 | 20.0 |
| | | 2.3 | 20.0 |
| 31 | Succinic Anhydrate | 1.7 | 4.0 |

After coupling succinic anhydride at step 31 and washing, the peptide-resin was treated in the manner as described in Example 26 to obtain a purified product.

The results of the amino acid analysis of the obtained purified product are shown below. Each parenthesized value is a theoretical value.

Asp; 2.99 (3), Thr; 4.75 (5), Ser; 0.90 (1),
Glu; 2.04 (2), Pro; 1.95 (2), Gly; 2.97 (3),
Ala; 1.96 (2), Val; 1.00 (1), Met; 1.08 (1),
Ile; 1.02 (1), Leu; 2.02 (2), Tyr; 1.11 (1),
Phe; 3.11 (3), Lys; 2.02 (2), His; 1.03 (1)

The above-results of the amino acid analysis support the conclusion that the purified product obtained by the above-mentioned process is peptide No. 34 having the amino acid composition shown in Table 1.

EXAMPLE 35

A purified product was obtained by subjecting 15 g of the peptide-resin at procedure (2) of Example 34 to the operations at procedure (3) of Example 34 except that instead of coupling methionine at step 25, the coupling of valine was carried out, as shown in Table 52.

TABLE 52

| | | Coupling Conditions | |
|---|---|---|---|
| Step | Protected Amino Acid | Amount used (g) | Time (hours) |
| 25 | Boc-Val | 2.2 | 4.0 |

The results of the amino acid analysis of the obtained purified product are shown below. Each parenthesized value is a theoretical value.

Asp; 2.96 (3), Thr; 4.65 (5), Ser; 0.93 (1),
Glu; 2.02 (2), Pro; 2.01 (2), Gly; 2.99 (3),
Ala; 2.02 (2), Val; 2.10 (2), Ile; 1.01 (1),
Leu; 2.06 (3), Tyr; 0.90 (1), Phe; 2.85 (3),
Lys; 2.03 (2), His; 0.99 (1)

The above-results of the amino acid analysis support the conclusion that the purified product obtained by the above-mentioned process is peptide No. 35 having the amino acid composition shown in Table 1.

EXAMPLE 36

A purified product was obtained by subjecting 15 g of the peptide-resin at procedure (2) of Example 34 to the operations at procedure (3) of Example 34 except that instead of coupling methionine at step 25, the coupling of leucine was carried out, as shown in Table 53.

TABLE 53

| | | Coupling Conditions | |
|---|---|---|---|
| Step | Protected Amino Acid | Amount used (g) | Time (hours) |
| 25 | Boc-Leu.H$_2$O | 2.5 | 4.0 |

The results of the amino acid analysis of the obtained purified product are shown below. Each parenthesized value is a theoretical value.

Asp; 2.91 (3), Thr; 4.52 (5), Ser; 0.84 (1),
Glu; 2.06 (2), Pro; 2.02 (2), Gly; 3.02 (3),
Ala; 2.01 (2), Val; 1.01 (1), Ile; 1.03 (1),
Leu; 3.15 (3), Tyr; 0.98 (1), Phe; 2.99 (3),
Lys; 1.98 (2), His; 1.07 (1)

The above-results of the amino acid analysis support the conclusion that the purified product obtained by the above-mentioned process is peptide No. 36 having the amino acid composition shown in Table 1.

EXAMPLE 37

By using 15 g of the peptide-resin obtained at procedure (2) of Example 34, protected amino acids shown in Table 54 were coupled in sequence, and the peptide-resin was treated in the manner as in Example 34 to obtain a purified product.

TABLE 54

| Step | Protected Amino Acid | Coupling Conditions | |
|---|---|---|---|
| | | Amount used (g) | Time (hours) |
| 25 | Boc-Met | 2.5 | 4.0 |
| 26 | Boc-Lys(ε-Fmoc) | 4.6 | 18.5 |
| 27 | Boc-Thr(Bzl) | 3.0 | 19.0 |
| 28 | Boc-Ser(Bzl) | 2.9 | 24.0 |
| | | 2.9 | 48.0 |
| 29 | Boc-Leu.H$_2$O | 2.5 | 4.0 |
| 30 | Boc-Asu | 3.1 | 17.0 |
| | | 2.3 | 20.0 |
| | | 2.3 | 20.0 |
| 31 | Boc-Gly | 1.8 | 4.0 |
| 32 | Succinic Anhydrate | 1.7 | 4.0 |

The results of the amino acid analysis of the obtained purified product are shown below. Each parethesized value is a theoretical value.

Asp; 3.02 (3), Thr; 4.58 (5), Ser; 0.88 (1),
Glu; 2.04 (2), Pro; 2.09 (2), Gly; 3.99 (4),
Ala; 2.00 (2), Val; 1.08 (1), Met; 1.00 (1),
Ile; 1.08 (1), Leu; 2.10 (2), Tyr; 0.86 (1),
Phe; 3.08 (3), Lys; 1.97 (2), His; 1.09 (1)

The above-results of the amino acid analysis support the conclusion that the purified product obtained by the above-mentioned process is peptide No. 37 having the amino acid composition shown in Table 1.

EXAMPLE 38

A purified product was obtained by subjecting 15 g of the peptide-resin at procedure (2) of Example 34 to the operations as in Example 37 except that instead of coupling methionine at step 25, the coupling of valine was carried out, as shown in Table 55.

TABLE 55

| Step | Protected Amino Acid | Coupling Conditions | |
|---|---|---|---|
| | | Amount used (g) | Time (hours) |
| 25 | Boc-Val | 2.2 | 4.0 |

The results of the amino acid analysis of the obtained purified product are shown below. Each parenthesized value is a theoretical value.

Asp; 3.01 (3), Thr; 4.66 (5), Ser; 0.86 (1),
Glu; 2.03 (2), Pro; 2.06 (2), Gly; 3.90 (4),
Ala; 2.06 (2), Val; 2.08 (2), Ile; 0.96 (1),
Leu; 2.08 (2), Tyr; 1.01 (1), Phe; 3.12 (3),
Lys; 2.00 (2), His; 0.99 (1)

The above-results of the amino acid analysis support the conclusion that the purified product obtained by the above-mentioned process is peptide No. 38 having the amino acid composition shown in Table 1.

EXAMPLE 39

A purified product was obtained by subjecting 15 g of the peptide-resin at procedure (2) of Example 34 to the operations as in Example 37 except that instead of coupling methionine at step 25, the coupling of leucine was carried out, as shown in Table 56.

TABLE 56

| Step | Protected Amino Acid | Coupling Conditions | |
|---|---|---|---|
| | | Amount used (g) | Time (hours) |
| 25 | Boc-Leu.H$_2$O | 2.5 | 4.0 |

The results of the amino acid analysis of the obtained purified product are shown below. Each parenthesized value is a theoretical value.

Asp; 2.98 (3), Thr; 4.72 (5), Ser; 0.92 (1),
Glu; 2.06 (2), Pro; 2.00 (2), Gly; 3.95 (4),
Ala; 1.99 (2), Val; 1.09 (1), Ile; 0.99 (1),
Leu; 3.08 (3), Tyr; 1.12 (1), Phe; 3.01 (3),
Lys; 2.01 (2), His; 1.04 (1)

The above-results of the amino acid analysis support the conclusion that the purified product obtained by the above-mentioned process is peptide No. 39 having the amino acid composition shown in Table 1.

EXAMPLE 40

By using 15 g of the peptide-resin obtained at procedure (2) of Example 34, protected amino acids shown in Table 57 were coupled in sequence, and the peptide-resin was treated in the manner as in Example 26 to obtain a purified product.

TABLE 57

| Step | Protected Amino Acid | Coupling Conditions | |
|---|---|---|---|
| | | Amount used (g) | Time (hours) |
| 25 | Boc-Met | 2.5 | 4.0 |
| 26 | Boc-Glu(O$^\beta$-Fmoc) | 3.4 | 16.0 |
| 27 | Boc-Thr(Bzl) | 3.0 | 19.0 |
| 28 | Boc-Ser(Bzl) | 2.9 | 24.0 |
| | | 2.9 | 48.0 |
| 29 | Boc-Leu.H$_2$O | 2.5 | 4.0 |
| 30 | Boc-Asn | 3.1 | 17.0 |
| | | 2.3 | 20.0 |
| | | 2.3 | 20.0 |
| 31 | Boc-Gly | 1.8 | 4.0 |
| 32 | Fmoc-Gly | 3.1 | 4.0 |

The results of the amino acid analysis of the obtained purified product are shown below. Each parenthesized value is a theoretical value.

Asp; 3.02 (3), Thr; 4.64 (5), Ser; 0.87 (1),
Glu; 3.10 (3), Pro; 1.92 (2), Gly; 4.85 (5),
Ala; 2.03 (2), Val; 1.10 (1), Met; 1.03 (1),
Ile; 1.00 (1), Leu; 2.12 (2), Tyr; 1.05 (1),
Phe; 2.89 (3), Lys; 1.00 (1), His; 1.06 (1)

The above-results of the amino acid analysis support the conclusion that the purified product obtained by the above-mentioned process is peptide No, 40 having the amino acid composition shown in Table 1.

EXAMPLE 41

A purified product was obtained by subjecting 15 g peptide-resin at procedure (2) of Example 34 to the operations as in Example 40 except that instead of coupling methionine at step 25, the coupling of valine was carried out, as shown in Table 58.

TABLE 58

| Step | Protected Amino Acid | Coupling Conditions | |
|---|---|---|---|
| | | Amount used (g) | Time (hours) |
| 25 | Boc-Val | 2.5 | 4.0 |

The results of the amino acid analysis of the obtained purified product are shown below. Each parenthesized value is a theoretical value.

Asp; 2.94 (3), Thr; 4.65 (5), Ser; 0.89 (1),
Glu; 3.07 (3), Pro; 1.99 (2), Gly; 4.93 (5),
Ala; 2.04 (2), Val; 2.12 (2), Ile; 1.07 (1),
Leu; 2.07 (2), Tyr; 1.01 (1), Phe; 2.95 (3),
Lys; 0.99 (1), His; 1.07 (1)

The above-results of the amino acid analysis support the conclusion that the purified product obtained by the above-mentioned process is peptide No. 41 having the amino acid composition shown in Table 1.

EXAMPLE 42

A purified product was obtained by subjecting 15 g of the peptide-resin at procedure (2) of Example 34 to the operations as in Example 40 except that instead of coupling methionine at step 25, the coupling of leucine was carried out, as shown in Table 59.

TABLE 59

| Step | Protected Amino Acid | Coupling Conditions | |
|---|---|---|---|
| | | Amount used (g) | Time (hours) |
| 25 | Boc-Leu.H$_2$O | 2.5 | 4.0 |

The results of the amino acid analysis of the obtained purified product are shown below. Each parenthesized value is a theoretical value.

Asp; 2.96 (3), Thr; 4.56 (5), Ser; 0.89 (1),
Glu; 3.01 (3), Pro; 2.01 (2), Gly; 4.96 (5),
Ala; 2.01 (2), Val; 1.04 (1), Ile; 1.06 (1),
Leu; 3.17 (3), Tyr; 0.95 (1), Phe; 2.99 (3),
Lys; 0.98 (1), His; 1.05 (1)

The above-results of the amino acid analysis support the conclusion that the purified product obtained by the above-mentioned process is peptide No. 42 having the amino acid composition shown in Table 1.

EXAMPLE 43

(1) Activation of Resin 50 g of the BHA resin as described in Example 1 was activated in the same manner as at procedure (1) of Example 1 except that the amount of the solvent was adjusted to ⅓ of the amount used in Example 1.

(2) Steps 1–13

By using all of the resin obtained at procedure (1), protected amino acids shown in Table 60 were coupled in sequence. DMF was used as the coupling solvent and BOP and DIEA were used as the coupling agent.

TABLE 60

| Step | Protected Amino Acid | Coupling Conditions | |
|---|---|---|---|
| | | Amount used (g) | Time (hours) |
| 1 | Boc-Pro | 21.5 | 2.8 |
| 2 | Boc-Thr(Bzl) | 31.0 | 2.0 |
| 3 | Boc-Gly | 17.5 | 2.0 |
| 4 | Boc-Ser(Bzl) | 29.6 | 2.0 |
| 5 | Boc-Gly | 17.5 | 3.0 |
| 6 | Boc-Thr(Bzl) | 31.0 | 2.0 |
| 7 | Boc-Asn | 27.9 | 4.0 |
| | | 13.9 | 15.0 |
| 8 | Boc-Thr(Bzl) | 31.0 | 2.0 |
| 9 | Boc-Arg(Tos) | 43.0 | 20.0 |
| 10 | Boc-Pro | 21.5 | 4.0 |
| | | 5.4 | 2.0 |
| 11 | Boc-Tyr(Br—Z) | 59.5 | 15.0 |
| 12 | Boc-Thr(Bzl) | 37.1 | 19.0 |
| 13 | Boc-Gln | 24.5 | 2.5 |

After coupling leucine at step 13 and washing, the peptide-resin was taken out from the reaction vessel and dried.

(3) Steps 14–25

By using 30 g of the peptide-resin obtained at procedure (2), protected amino acids shown in Table 61 were coupled in sequence.

TABLE 61

| Step | Protected Amino Acid | Coupling Conditions | |
|---|---|---|---|
| | | Amount used (g) | Time (hours) |
| 14 | Boc-Leu.H$_2$O | 10.0 | 20.0 |
| 15 | Boc-Lys(Cl—Z) | 17.0 | 16.0 |
| 16 | Boc-His(Tos) | 17.0 | 23.0 |
| 17 | Boc-Leu.H$_2$O | 10.0 | 20.0 |
| 18 | Boc-Glu(OBzl) | 13.5 | 17.0 |
| lg | Boc-Gln | 10.0 | 4.0 |
| 20 | Boc-Ser(Bzl) | 9.9 | 2.0 |
| 21 | Boc-Leu.H$_2$O | 10.0 | 20.0 |
| 22 | Boc-Lys(Cl—Z) | 17.0 | 16.0 |
| 23 | Boc-Gly | 7.0 | 16.0 |
| 24 | Boc-Leu.H$_2$O | 10.0 | 20.0 |
| 25 | Boc-Val | 8.7 | 4.0 |

After coupling valine at step 25 and washing, the peptide-resin was taken out from the reaction vessel and dried.

(4) Steps 26–31

By using 15 g of the peptide-resin obtained at procedure (3), the peptide-resin was treated in the same manner as at step 26 at procedure (3) of Example 34 and subsequent steps to obtain a purified product.

The results of the amino acid analysis of the obtained purified product are shown below. Each parethesized value is a theoretical value.

Asp; 1.94 (2), Thr; 4.62 (5), Ser; 2.67 (3),
Glu; 3.00 (3), Pro; 2.05 (2), Gly; 3.02 (3), Val;
  1.05 (1), Leu; 5.00 (5), Tyr; 0.99 (1), Lys; 2.93 (3). His;
  1.00 (1), Arg; 1.01 (1)

The above-results of the amino acid analysis support the conclusion that the purified product obtained by the above-mentioned process is peptide No. 43 having the amino acid composition shown in Table 1.

EXAMPLE 44

A purified product was obtained by subjecting 30 g of the peptide-resin at procedure (2) of Example 43 to the operations at procedures (3) and (4) of Example 43 except that the coupling of leucine at step 14 at procedure (3) of Example 43 was not carried out.

The results of the amino acid analysis of the obtained purified product are shown below. Each parenthesized value is a theoretical value.

Asp; 1.94 (2), Thr; 4.54 (5), Ser; 2.74 (3),

Glu; 3.05 (3), Pro; 2.06 (2), Gly; 2.98 (3),

Val; 1.02 (1), Leu; 4.05 (4), Tyr; 0.93 (1),

Lys; 2.90 (3). His; 1.09 (1), Arg; 0.94 (1)

The above-results of the amino acid analysis support the conclusion that the purified product obtained by the above-mentioned process is peptide No. 44 having the amino acid composition shown in Table 1.

EXAMPLE 45

A purified product was obtained by subjecting 15 g of the peptide-resin at procedure (3) of Example 43 to the same operation as at step 26 of Example 40 and subsequent steps except that instead of coupling glycine at step 31, the coupling of serine was carried out, as shown in Table 62.

TABLE 62

| | | Coupling Conditions | |
|---|---|---|---|
| Step | Protected Amino Acid | Amount used (g) | Time (hours) |
| 31 | Boc-Ser(Bzl) | 2.9 | 24.0 |
| | | 2.9 | 48.0 |

The results of the amino acid analysis of the obtained purified product are shown below. Each parenthesized value is a theoretical value.

Asp; 1.98 (2), Thr; 4.70 (5), Ser; 3.64 (4),

Glu; 4.08 (4), Pro; 2.00 (2), Gly; 3.01 (3),

Val; 1.01 (1), Leu; 5.20 (5), Tyr; 1.04 (1),

Lys; 2.01 (2). His; 1.09 (1), Arg; 1.05 (1)

The above-results of the amino acid analysis support the conclusion that the purified product obtained by the above-mentioned process is peptide No. 45 having the amino acid composition shown in Table 1.

EXAMPLE 46

15 g of the peptide-resin obtained at step 25 of Example 44 was treated in the manner as in Example 45 to obtain a purified product.

The results of the amino acid analysis of the obtained purified product are shown below. Each parenthesized value is a theoretical value.

Asp; 1.90 (2), Thr; 4.66 (5), Ser; 3.58 (4),

Glu; 4.06 (4), Pro; 1.97 (2), Gly; 3.07 (3),

Val; 1.09 (1), Leu; 4.02 (4), Tyr; 0.89 (1),

Lys; 1.98 (2). His; 1.02 (1), Arg; 1.02 (1)

The above-results of the amino acid analysis support the conclusion that the purified product obtained by the above-mentioned process is peptide No. 46 having the amino acid composition shown in Table 1.

EXAMPLE 47

(1) Activation of Resin 50 g of the BHA resin as described in Example 1 was activated in the same manner as at procedure (1) of Example 1 except that the amount of the solvent was adjusted to ⅓ of the amount used in Example 1.

(2) Steps 1–25

By using all of the resin obtained at procedure (1), protected amino acids shown in Table 63 were coupled in sequence. DMF was used as the coupling solvent and BOP and DIEA were used as the coupling agent.

TABLE 63

| | | Coupling Conditions | |
|---|---|---|---|
| Step | Protected Amino Acid | Amount used (g) | Time (hours) |
| 1 | Boc-Pro | 21.5 | 2.8 |
| 2 | Boc-Thr(Bzl) | 31.0 | 2.0 |
| 3 | Boc-Gly | 17.5 | 2.0 |
| 4 | Boc-Ala | 19.0 | 2.5 |
| 5 | Boc-Gly | 17.5 | 3.0 |
| 6 | Boc-Val | 21.8 | 2.0 |
| 7 | Boc-Asp(OBzl) | 38.8 | 17.0 |
| 8 | Boc-Thr(Bzl) | 31.0 | 2.0 |
| 9 | Boc-Arg(Tos) | 43.0 | 20.0 |
| 10 | Boc-Pro | 21.5 | 4.0 |
| | | 5.4 | 2.0 |
| 11 | Boc-Tyr(Br—Z) | 59.5 | 15.0 |
| 12 | Boc-Thr(Bzl) | 37.1 | 19.0 |
| 13 | Boc-Gln | 24.5 | 2.5 |
| 14 | Boc-Leu.H₂O | 29.9 | 20.0 |
| 15 | Boc-Lys(Cl—Z) | 50.0 | 16.0 |
| 16 | Boc-His(Tos) | 50.0 | 23.0 |
| 17 | Boc-Leu.H₂O | 29.9 | 20.0 |
| 18 | Boc-Glu(OBzl) | 40.5 | 17.0 |
| 19 | Boc-Gln | 30.0 | 4.0 |
| 20 | Boc-Ser(Bzl) | 29.7 | 2.0 |
| 21 | Boc-Leu.H₂O | 29.9 | 20.0 |
| 22 | Boc-Lys(Cl—Z) | 50.0 | 16.0 |
| 23 | Boc-Gly | 21.0 | 16.0 |
| 24 | Boc-Leu.H₂O | 29.9 | 20.0 |
| 25 | Boc-Val | 26.1 | 4.0 |

After coupling valine at step 25 and washing, the peptide-resin was taken out from the reaction vessel and dried.

(3) Steps 26–31

15 g of the peptide-resin obtained at procedure (2) was treated in the same manner as at step 26 at procedure (3) of Example 34 and subsequent steps to obtain a purified product.

The results of the amino acid analysis of the obtained purified product are shown below. Each parenthesized value is a theoretical value.

Asp; 1.92 (2), Thr; 3.56 (4), Ser; 1.76 (2),

Glu; 3.06 (3), Pro; 2.02 (2), Gly; 3.05 (3),

Ala; 0.98 (1), Val; 2.18 (2), Leu; 5.25 (5),

Tyr; 1.07 (1), Lys; 2.95 (3). His; 1.03 (1),

Arg; 0.99 (1)

The above-results of the amino acid analysis support the conclusion that the purified product obtained by the above-mentioned process is peptide No. 47 having the amino acid composition shown in Table 1.

EXAMPLE 48

15 g of the peptide-resin obtained at procedure (2) of Example 47 was treated in the manner as in Example 45 to obtain a purified product.

The results of the amino acid analysis of the obtained purified product are shown below. Each parenthesized value is a theoretical value.

Asp; 1.94 (2), Thr; 3.60 (4), Ser; 2.72 (3),
Glu; 4.11 (4), Pro; 2.02 (2), Gly; 3.93 (4),
Ala; 1.01 (1), Val; 2.02 (2), Leu; 5.16 (5),
Tyr; 1.05 (1), Lys; 1.95 (2). His; 0.99 (1),
Arg; 0.98 (1)

The above-results of the amino acid analysis support the conclusion that the purified product obtained by the above-mentioned process is peptide No. 48 having the amino acid composition shown in Table 1.

EXAMPLE 49

A purified product was obtained by subjecting 15 g of the peptide-resin at procedure (2) of Example 47 to the same operation as at step 26 at procedure (3) of Example 34 and subsequent steps except that instead of coupling asparagine at step 30, the coupling of serine was carried out, as shown in Table 64.

TABLE 64

| | | Coupling Conditions | |
|---|---|---|---|
| Step | Protected Amino Acid | Amount used (g) | Time (hours) |
| 30 | Boc-Ser(Bzl) | 2.9 | 24.0 |
| | | 2.9 | 48.0 |

The results of the amino acid analysis of the obtained purified product are shown below. Each parenthesized value is a theoretical value.

Asp; 1.00 (1), Thr; 3.64 (4), Ser; 2.58 (3),
Glu; 3.05 (3), Pro; 1.93 (2), Gly; 2.99 (3),
Ala; 1.00 (1), Val; 2.04 (2), Leu; 5.28 (5),
Tyr; 0.99 (1), Lys; 2.88 (3), His; 1.04 (1),
Arg; 1.03 (1)

The above-results of the amino acid analysis support the conclusion that the purified product obtained by the above-mentioned process is peptide No. 49 having the amino acid composition shown in Table 1.

EXAMPLE 50

A purified product was obtained by subjecting 15 g of the peptide-resin at procedure (2) of Example 47 to the same operation as at step 26 of Example 40 and subsequent steps except that instead of coupling asparagine at step 30, the coupling of serine was carried out, and instead of coupling glycine at step 31, the coupling of alanine was carried out, as shown in Table 65.

TABLE 65

| | | Coupling Conditions | |
|---|---|---|---|
| Step | Protected Amino Acid | Amount used (g) | Time (hours) |
| 30 | Boc-Ser(Bzl) | 2.9 | 24.0 |
| | | 2.9 | 48.0 |
| 31 | Boc-Ala | 1.9 | 4.0 |

The results of the amino acid analysis of the obtained purified product are shown below. Each parenthesized value is a theoretical value.

Asp; 1.01 (1), Thr; 3.62 (4), Ser; 2.64 (3),
Glu; 4.09 (4), Pro; 1.99 (2), Gly; 3.97 (4),
Ala; 2.01 (2), Val; 2.14 (2), Leu; 5.08 (5),
Tyr; 0.94 (1), Lys; 2.00 (2), His; 1.05 (1),
Arg; 1.00 (1)

The above-results of the amino acid analysis support the conclusion that the purified product obtained by the above-mentioned process is peptide No. 50 having the amino acid composition shown in Table 1.

EXAMPLE 51

A purified product was obtained by subjecting 15 g of the peptide-resin at procedure (2) of Example 47 to the same operation as at step 26 of Example 40 and subsequent steps except that instead of coupling asparagine at step 30, the coupling of serine was carried out, and instead of coupling glycine at step 31, the coupling of asparagine was carried out, as shown in Table 66.

TABLE 66

| | | Coupling Conditions | |
|---|---|---|---|
| Step | Protected Amino Acid | Amount used (g) | Time (hours) |
| 30 | Boc-Ser(Bzl) | 2.9 | 24.0 |
| | | 2.9 | 48.0 |
| 31 | Boc-Asn | 3.1 | 17.0 |
| | | 2.3 | 20.0 |
| | | 2.3 | 20.0 |

The results of the amino acid analysis of the obtained purified product are shown below. Each parenthesized value is a theoretical value.

Asp; 1.94 (2), Thr; 3.54 (4), Ser; 2.70 (3),
Glu; 4.06 (4), Pro; 2.01 (2), Gly; 3.91 (4),
Ala; 0.99 (1), Val; 2.09 (2), Leu; 5.19 (5),
Tyr; 1.00 (1), Lys; 2.03 (2). His; 1.07 (1),
Arg; 1.02 (1)

The above-results of the amino acid analysis support the conclusion that the purified product obtained by the above-mentioned process is peptide No. 51 having the amino acid composition shown in Table 1.

EXAMPLE 52

(1) Activation of Resin 50 g of the BHA resin as described in Example 1 was activated in the same manner as at procedure (1) of Example 1 except that the amount of the solvent was adjusted to ⅓ of the amount used in Example 1.

(2) Steps 1–25

By using all of the resin obtained at procedure (1), protected amino acids shown in Table 67 were coupled in sequence. DMF was used as the coupling solvent and BOP and DIEA were used as the coupling agent.

TABLE 67

| | | Coupling Conditions | |
|---|---|---|---|
| Step | Protected Amino Acid | Amount used (g) | Time (hours) |
| 1 | Boc-Pro | 21.5 | 2.8 |
| 2 | Boc-Thr(Bzl) | 31.0 | 2.0 |
| 3 | Boc-Glu(OBzl) | 33.9 | 2.0 |

TABLE 67-continued

| | | Coupling Conditions | |
|---|---|---|---|
| Step | Protected Amino Acid | Amount used (g) | Time (hours) |
| 4 | Boc-Pro | 21.5 | 4.0 |
| 5 | Boc-Gly | 17.5 | 3.0 |
| 6 | Boc-Phe | 31.9 | 19.0 |
| | | 15.9 | 16.0 |
| 7 | Boc-Gly | 17.5 | 3.0 |
| 8 | Boc-Met | 25.0 | 4.0 |
| 9 | Boc-Gly | 17.5 | 3.0 |
| 10 | Boc-Ser(Bzl) | 29.7 | 2.0 |
| 11 | Boc-Phe | 31.9 | 4.0 |
| 12 | Boc-Arg(Tos) | 43.0 | 20.0 |
| 13 | Boc-His(Tos) | 50.0 | 23.0 |
| 14 | Boc-Phe | 31.9 | 4.0 |
| 15 | Boc-Asn | 27.9 | 4.0 |
| | | 13.9 | 15.0 |
| 16 | Boc-Asn | 27.9 | 4.0 |
| | | 13.9 | 15.0 |
| 17 | Boc-Leu.H$_2$O | 29.9 | 20.0 |
| 18 | Boc-Asn | 27.9 | 4.0 |
| | | 13.9 | 15.0 |
| 19 | Boc-Arg(Tos) | 43.0 | 20.0 |
| 20 | Boc-Trp | 30.5 | 15.0 |
| 21 | Boc-Tyr(Br—Z) | 59.5 | 15.0 |
| 2Z | Boc-Ala | 19.0 | 2.5 |
| 23 | Boc-Ser(Bzl) | 29.7 | 2.0 |
| 24 | Boc-Leu.H$_2$O | 29.9 | 20.0 |
| 25 | Boc-Val | 26.1 | 4.0 |

After coupling valine at step 25 and washing, the peptide-resin was taken out from the reaction vessel and dried.
(3) Steps 26–31

15 g of the peptide-resin obtained at procedure (2) was treated in the same manner as at step 26 at procedure (3) of Example 34 and subsequent steps to obtain a purified product.

The results of the amino acid analysis of the obtained purified product are shown below. Each parenthesized value is a theoretical value.

Asp; 3.96 (4), Thr; 1.87 (2), Ser; 2.68 (3),

Glu; 1.02 (1), Pro; 2.03 (2), Gly; 3.03 (3),

Ala; 1.00 (1), Val; 1.05 (1), Met; 0.96 (1),

Leu; 3.09 (3), Tyr; 1.02 (1), Phe; 2.99 (3),

Lys; 1.02 (1), His; 0.99 (1), Arg; 1.99 (2),

Trp; 0.85 (1)

The above-results of the amino acid analysis support the conclusion that the purified product obtained by the above-mentioned process is peptide No. 52 having the amino acid composition shown in Table 1.

EXAMPLE 53

15 g of the peptide-resin obtained at procedure (2) of Example 52 was treated in the manner as in Example 45 to obtain a purified product.

The results of the amino acid analysis of the obtained purified product are shown below. Each parenthesized value is a theoretical value.

Asp; 4.01 (4), Thr; 1.85 (2), Ser; 3.70 (4),

Glu; 2.03 (2), Pro; 1.99 (2), Gly; 3.92 (4),

Ala; 0.99 (1), Val; 1.0.7 (1), Met; 1.09 (1),

Leu; 3.02 (3), Tyr; 1.04 (1), Phe; 3.01 (3),

His; 1.04 (1), Arg; 2.05 (2), Trp; 0.88 (1)

The above-results of the amino acid analysis support the conclusion that the purified product obtained by the above-mentioned process is peptide No. 53 having the amino acid composition shown in Table 1.

EXAMPLE 54

An injection was prepared from the peptide obtained in Example 1, distilled water for injection, sodium chloride, and gelatin by a customary injection-preparing process.

EXAMPLE 55

An injection was prepared from the peptide obtained in Example 2, distilled water for injection, sodium chloride, sodium acetate, benzyl alcohol and gelatin, by a customary injection-preparing process.

EXAMPLE 56

An injection was prepared from the peptide obtained in Example 3, distilled water for injection, sodium chloride, sodium acetate, gelatin, and phenol, by a customary injection-preparing process.

EXAMPLE 57

An injection was prepared from the peptide, distilled water for injection, sodium chloride, sodium acetate, methyl p-hydroxybenzoate, ethyl p-hydroxybenzoate, propyl p-hydroxybenzoate, and butyl p-hydroxybenzoate, by a customary injection-preparing process.

EXAMPLE 58

An injection was prepared from the peptide obtained in Example 5, sodium chloride, sodium acetate, hydrochloric acid, methyl p-hydroxybenzoate, ethyl p-hydroxybenzoate, propyl p-hydroxybenzoate, and butyl p-hydroxybenzoate, by a customary injection-preparing process.

EXAMPLE 59

An aqueous solution containing the peptide obtained in Example 6 and mannitol was freeze-dried. At the time of administration, the dry product was dissolved in an aqueous solution containing gelatin and phenol, to prepare an injection.

EXAMPLE 60

An aqueous solution containing the peptide obtained in Example 7, sodium acetate, and human albumin was freeze-dried. At the time of administration, the dry product was dissolved in distilled water for injection, to prepare an injection.

EXAMPLE 61

A suppository was prepared from the peptide obtained in Example 8 and cacao fat or whitep sol, by a customary suppository-preparing process.

EXAMPLE 62

An aqueous solution containing the peptide obtained in Example 1, glacial acetic acid, sodium acetate and benzalkonium chloride was sprayed as a nasal mucosa medicine into the nasal cavity.

EXAMPLE 63

An aqueous solution containing the peptide obtained in Example 2, glacial acetic acid, sodium acetate and a bile acid salt was sprayed as a nasal mucosa medicine into the nasal cavity.

What is claimed is:

1. A peptide having the following amino acid sequence (SEQ ID NO: 25):

```
              CH₂--CO--NH--CH₂--CH₂-CH₂-CH₂
              |                            |
CH₃CO-NH-CH-CO-Asn-Leu-Ser-Thr-NH-CH-CO-Leu-Leu-
        1     2   3   4   5       6   7   8
Gly-Lys-Leu-Ser-Gln-Glu-Leu-His-Lys-Leu-Gln-Thr-
 9   10  11  12  13  14  15  16  17  18  19  20
Tyr-Pro-Gln-Thr-Ala-Ile-Gly-Val-Gly-Ala-Pro-NH₂
 21  22  23  24  25  26  27  28  29  30  31.
```

2. A peptide having the following amino acid sequence (SEQ ID NO: 26):

```
CH₂—CO—NH—CH₂-CH₂—CH₂—CH₂
|                        |
CH₂-CO-Asn-Leu-Ser-Thr-NH-CH-CO-Leu-Leu-Gly-Lys-
1    2   3   4   5       6   7   8   9   10
Leu-Ser-Gln-Glu-Leu-His-Lys-Leu-Gln-Thr-Tyr-Pro-
 11  12  13  14  15  16  17  18  19  20  21  22
Gln-Thr-Ala-Ile-Gly-Val-Gly-Ala-Pro-NH₂
 23  24  25  26  27  28  29  30  31.
```

3. A pharmaceutical composition to decrease the serum level of calcium, said composition comprising an effective amount of the peptide having the following amino acid sequence (SEQ ID NO: 25):

```
              CH₂—CO—NH—CH₂-CH₂—CH₂—CH₂
              |                        |
CH₃CO—NH—CH—CO-Asn-Leu-Ser-Thr-NH—CH—CO-Leu-Leu-
        1     2   3   4   5       6   7   8
Gly-Lys-Leu-Ser-Gln-Glu-Leu-His-Lys-Leu-Gln-Thr-
 9   10  11  12  13  14  15  16  17  18  19  20
Tyr-Pro-Gln-Thr-Ala-Ile-Gly-Val-Gly-Ala-Pro-NH₂
 21  22  23  24  25  26  27  28  29  30  31
``` to decrease the serum level of calcium and a pharmaceutically acceptable carrier therefor.

4. A pharmaceutical composition to decrease the serum level of calcium, said composition comprising an effective amount of the peptide having the following amino acid sequence (SEQ ID NO: 26):

```
CH₂—CO—NH—CH₂-CH₂—CH₂—CH₂
|                        |
CH₂-CO-Asn-Leu-Ser-Thr-NH—CH—CO-Leu-Leu-Gly-Lys-
1    2   3   4   5       6   7   8   9   10
Leu-Ser-Gln-Glu-Leu-His-Lys-Leu-Gln-Thr-Tyr-Pro-
 11  12  13  14  15  16  17  18  19  20  21  22
Gln-Thr-Ala-Ile-Gly-Val-Gly-Ala-Pro-NH₂
 23  24  25  26  27  28  29  30  31
``` to decrease the serum level of calcium, and a pharmaceutically acceptable carrier therefor.

* * * * *

UNITED STATES PATENT AND TRADEMARK OFFICE
CERTIFICATE OF CORRECTION

PATENT NO. : 6,127,519
DATED : October 3, 2000
INVENTOR(S) : Ronald C. Orlowski et al.

It is certified that error appears in the above-identified patent and that said Letters Patent is hereby corrected as shown below:

In section [63] change "07/431,350" to --07/437,350--

Signed and Sealed this

Twenty-second Day of May, 2001

Attest:

NICHOLAS P. GODICI

Attesting Officer     Acting Director of the United States Patent and Trademark Office